US009421113B2

(12) United States Patent
Fabian

(10) Patent No.: US 9,421,113 B2
(45) Date of Patent: *Aug. 23, 2016

(54) SPINE SURGERY METHOD AND INSERTER

(71) Applicant: Henry F. Fabian, Steamboat Springs, CO (US)

(72) Inventor: Henry F. Fabian, Steamboat Springs, CO (US)

(*) Notice: Subject to any disclaimer, the term of this patent is extended or adjusted under 35 U.S.C. 154(b) by 152 days.

This patent is subject to a terminal disclaimer.

(21) Appl. No.: 14/077,784

(22) Filed: Nov. 12, 2013

(65) Prior Publication Data

US 2015/0134062 A1 May 14, 2015

Related U.S. Application Data

(60) Continuation of application No. 13/448,877, filed on Apr. 17, 2012, now Pat. No. 8,579,977, which is a division of application No. 12/108,625, filed on Apr. 24, 2008.

(51) Int. Cl.
*A61F 2/46* (2006.01)
*A61F 2/44* (2006.01)
*A61F 2/30* (2006.01)

(52) U.S. Cl.
CPC .............. *A61F 2/4611* (2013.01); *A61F 2/442* (2013.01); *A61F 2/4425* (2013.01); *A61F 2/4455* (2013.01); *A61F 2002/30179* (2013.01); *A61F 2002/30462* (2013.01); *A61F 2002/30471* (2013.01); *A61F 2002/30579* (2013.01); *A61F 2002/4415* (2013.01); *A61F 2002/4622* (2013.01); *A61F 2002/4624* (2013.01); *A61F 2002/4628* (2013.01); *A61F 2002/4679* (2013.01); *A61F 2220/0075* (2013.01); *A61F 2220/0091* (2013.01);

(Continued)

(58) Field of Classification Search
CPC ..................................................... A61F 2/4611
See application file for complete search history.

(56) References Cited

U.S. PATENT DOCUMENTS 2,417,114 A 3/1947 Killham
2,907,189 A 10/1959 Fleig
(Continued)

FOREIGN PATENT DOCUMENTS

| EP | 0 773 008 | 5/1997 |
| EP | 1 506 753 B1 | 2/2005 |
| FR | 2717068 | 9/1995 |
| WO | WO 98 14142 A | 4/1998 |
| WO | WO 01/01895 A1 | 1/2001 |
| WO | WO 02/05733 A1 | 1/2002 |

OTHER PUBLICATIONS

PCT, International Preliminary Report on Patentability, Dec. 13, 2007.

(Continued)

*Primary Examiner* — Nicholas Woodall
(74) *Attorney, Agent, or Firm* — Timothy D. Bennett; Emerson, Thomson, Bennett

(57) ABSTRACT

A surgical inserter for use in inserting an implant into a vertebral space may include: (a) a handle; (b) a gripper having one end attached to the handle and a second end having a pair of arms; and (c) a grip activator having an opening that threadingly receives the gripper. The grip activator can be rotated in a first direction with respect to the gripper to cause the arms to move toward each other to grip the inserter and in a second direction with respect to the gripper to cause the arms to move away from each other to release the inserter. In one embodiment a compression force activator is used to deploy the implant and in another embodiment a tension force activator is used to deploy the implant.

20 Claims, 53 Drawing Sheets

(52) U.S. Cl.
CPC ............... *A61F 2230/0058* (2013.01); *A61F 2310/00017* (2013.01); *A61F 2310/00023* (2013.01); *A61F 2310/00029* (2013.01); *A61F 2310/00161* (2013.01); *A61F 2310/00179* (2013.01)

(56) References Cited

U.S. PATENT DOCUMENTS

| | | |
|---|---|---|
| 3,867,728 A | 2/1975 | Stubstad et al. |
| 4,309,777 A | 1/1982 | Patil |
| 4,349,921 A | 9/1982 | Kuntz |
| 4,401,112 A | 8/1983 | Rezaian |
| 4,501,269 A | 2/1985 | Bagby |
| 4,553,273 A | 11/1985 | Wu |
| 4,643,178 A | 2/1987 | Nastari et al. |
| 4,714,469 A | 12/1987 | Kenna |
| 4,743,256 A | 5/1988 | Brantigan |
| 4,759,769 A | 7/1988 | Hedman et al. |
| 4,772,287 A | 9/1988 | Ray et al. |
| 4,820,305 A | 4/1989 | Harms et al. |
| 4,834,757 A | 5/1989 | Brantigan |
| 4,863,477 A | 9/1989 | Monson |
| 4,878,915 A | 11/1989 | Brantigan |
| 4,932,969 A | 6/1990 | Frey et al. |
| 4,932,975 A | 6/1990 | Main et al. |
| 4,946,378 A | 8/1990 | Hirayama et al. |
| 4,961,740 A | 10/1990 | Ray et al. |
| 5,002,576 A | 3/1991 | Fuhrmann et al. |
| 5,015,247 A | 5/1991 | Michelson |
| 5,055,104 A | 10/1991 | Ray |
| 5,071,437 A | 12/1991 | Steffee |
| 5,123,926 A | 6/1992 | Pisharodi |
| 5,156,839 A | 10/1992 | Pennell et al. |
| 5,192,327 A | 3/1993 | Brantigan |
| 5,246,458 A | 9/1993 | Graham |
| 5,314,477 A | 5/1994 | Marnay |
| 5,368,600 A | 11/1994 | Failla et al. |
| 5,397,364 A | 3/1995 | Kozak et al. |
| 5,439,464 A | 8/1995 | Shapiro |
| 5,484,437 A | 1/1996 | Michelson |
| 5,505,732 A | 4/1996 | Michelson |
| 5,571,192 A | 11/1996 | Schonhoffer |
| 5,665,122 A | 9/1997 | Kambin |
| 5,772,661 A | 6/1998 | Michelson |
| 5,782,919 A | 7/1998 | Zdeblick et al. |
| 5,785,647 A | 7/1998 | Tompkins et al. |
| 5,976,187 A | 11/1999 | Richelsoph |
| 6,080,155 A | 6/2000 | Michelson |
| 6,093,205 A | 7/2000 | McLeod et al. |
| 6,093,207 A | 7/2000 | Pisharodi |
| 6,159,211 A | 12/2000 | Boriani et al. |
| 6,159,214 A | 12/2000 | Michelson |
| 6,193,757 B1 | 2/2001 | Foley et al. |
| 6,200,348 B1 | 3/2001 | Biedermann et al. |
| 6,206,922 B1 | 3/2001 | Zdeblick et al. |
| 6,228,022 B1 | 5/2001 | Friesem et al. |
| 6,264,657 B1 | 7/2001 | Urbahns et al. |
| 6,283,966 B1 | 9/2001 | Houfburg |
| 6,332,887 B1 | 12/2001 | Knox |
| 6,395,031 B1 | 5/2002 | Foley et al. |
| 6,395,034 B1 | 5/2002 | Suddaby |
| 6,402,785 B1 | 6/2002 | Zdeblick et al. |
| 6,409,766 B1 | 6/2002 | Brett |
| 6,471,724 B2 | 10/2002 | Zdeblick et al. |
| 6,488,710 B2 | 12/2002 | Besselink |
| 6,514,260 B1 | 2/2003 | Zdeblick et al. |
| 6,524,318 B1 | 2/2003 | Longhini et al. |
| 6,554,836 B2 | 4/2003 | Michelson |
| 6,565,574 B2 | 5/2003 | Michelson |
| 6,575,981 B1 | 6/2003 | Boyd et al. |
| 6,599,292 B1 | 7/2003 | Ray |
| 6,626,943 B2 | 9/2003 | Eberlein et al. |
| 6,648,895 B2 | 11/2003 | Burkus et al. |
| 6,652,533 B2 | 11/2003 | O'Neil |
| 6,695,851 B2 | 2/2004 | Zdeblick et al. |
| 6,695,857 B2 | 2/2004 | Gifford, III et al. |
| 6,706,068 B2 | 3/2004 | Ferree |
| 6,709,458 B2 | 3/2004 | Michelson |
| 6,712,818 B1 | 3/2004 | Michelson |
| 6,712,819 B2 | 3/2004 | Zucherman et al. |
| 6,712,825 B2 | 3/2004 | Aebi et al. |
| 6,716,247 B2 | 4/2004 | Michelson |
| 6,719,794 B2 | 4/2004 | Gerber et al. |
| 6,723,096 B1 | 4/2004 | Dorchak et al. |
| 6,723,109 B2 | 4/2004 | Solingen |
| 6,730,127 B2 | 5/2004 | Michelson |
| 6,733,535 B2 | 5/2004 | Michelson |
| 6,740,087 B2 | 5/2004 | Knox |
| 6,743,234 B2 | 6/2004 | Burkus et al. |
| 6,746,484 B1 | 6/2004 | Liu et al. |
| 6,749,636 B2 | 6/2004 | Michelson |
| 6,755,841 B2 | 6/2004 | Fraser et al. |
| 6,758,849 B1 | 7/2004 | Michelson |
| 6,761,723 B2 | 7/2004 | Buttermann et al. |
| 6,767,367 B1 | 7/2004 | Michelson |
| 6,770,074 B2 | 8/2004 | Michelson |
| 6,773,460 B2 | 8/2004 | Jackson |
| 6,793,679 B2 | 9/2004 | Michelson |
| 6,808,537 B2 | 10/2004 | Michelson |
| 6,814,737 B2 | 11/2004 | Cauthen |
| 6,814,756 B1 | 11/2004 | Michelson |
| 6,824,565 B2 | 11/2004 | Muhanna et al. |
| 6,827,740 B1 | 12/2004 | Michelson |
| 6,830,570 B1 | 12/2004 | Frey et al. |
| 6,830,574 B2 | 12/2004 | Heckele et al. |
| 6,833,006 B2 | 12/2004 | Foley et al. |
| 6,835,208 B2 | 12/2004 | Marchosky |
| 6,849,093 B2 | 2/2005 | Michelson |
| 6,863,673 B2 | 3/2005 | Gerbec et al. |
| 6,893,465 B2 | 5/2005 | Huang |
| 6,902,566 B2 | 6/2005 | Zucherman et al. |
| 6,902,579 B2 | 6/2005 | Harms et al. |
| 6,908,485 B2 | 6/2005 | Crozet et al. |
| 6,923,814 B1 | 8/2005 | Hildebrand et al. |
| 6,932,844 B2 | 8/2005 | Ralph et al. |
| 6,942,698 B1 | 9/2005 | Jackson |
| 7,048,766 B2 | 5/2006 | Ferree |
| 7,060,073 B2 | 6/2006 | Frey et al. |
| 7,066,960 B1 | 6/2006 | Dickman |
| 7,070,598 B2 | 7/2006 | Lim et al. |
| 7,081,120 B2 | 7/2006 | Li et al. |
| 7,083,650 B2 | 8/2006 | Moskowitz et al. |
| 7,084,766 B2 | 8/2006 | Sayegh et al. |
| 7,087,055 B2 | 8/2006 | Lim et al. |
| 7,090,680 B2 | 8/2006 | Bonati et al. |
| 7,128,760 B2 | 10/2006 | Michelson |
| 7,156,849 B2 | 1/2007 | Dunbar |
| 7,163,561 B2 | 1/2007 | Michelson |
| 7,179,294 B2 | 2/2007 | Eisermann et al. |
| 7,195,643 B2 | 3/2007 | Jackson |
| 7,195,645 B2 | 3/2007 | Disilvestro et al. |
| 7,204,853 B2 | 4/2007 | Gordon et al. |
| 7,208,014 B2 | 4/2007 | Ralph et al. |
| 7,316,714 B2 | 1/2008 | Gordon et al. |
| 7,318,839 B2 | 1/2008 | Malberg et al. |
| 7,326,251 B2 | 2/2008 | McCombe et al. |
| 8,579,977 B2 * | 11/2013 | Fabian ................ 623/17.11 |
| 2002/0045904 A1 | 4/2002 | Fuss et al. |
| 2002/0045944 A1 | 4/2002 | Muhanna et al. |
| 2002/0055745 A1 | 5/2002 | McKinley et al. |
| 2003/0114860 A1 | 6/2003 | Cavagna et al. |
| 2004/0153089 A1 | 8/2004 | Zdeblick et al. |
| 2004/0210313 A1 | 10/2004 | Michelson |
| 2004/0230100 A1 | 11/2004 | Shluzas |
| 2004/0230309 A1 | 11/2004 | DiMauro et al. |
| 2004/0236331 A1 | 11/2004 | Michelson |
| 2004/0249388 A1 | 12/2004 | Michelson |
| 2005/0209698 A1 | 9/2005 | Gordon et al. |
| 2006/0030860 A1 | 2/2006 | Peterman |
| 2006/0096275 A1 | 5/2006 | Robel et al. |
| 2007/0073398 A1 * | 3/2007 | Fabian et al. .......... 623/17.11 |
| 2008/0109005 A1 | 5/2008 | Trudeau et al. |
| 2008/0243255 A1 | 10/2008 | Butler et al. |
| 2008/0300601 A1 * | 12/2008 | Fabian et al. ............ 606/90 |

(56) References Cited

U.S. PATENT DOCUMENTS

2009/0048676 A1    2/2009    Fabian, Jr.
2009/0138055 A1    5/2009    Altarac et al.
2009/0270873 A1*  10/2009  Fabian ............................ 606/99
2012/0029645 A1*  2/2012   Fabian et al. ............... 623/17.16
2013/0310939 A1*  11/2013  Fabian et al. ............... 623/17.16

OTHER PUBLICATIONS

PCT, International Search Report, Nov. 7, 2006.
PCT, Written Opinion of the International Searching Authority, Nov. 7, 2006.
PCT, Invitation to Pay Additional Fees, Nov. 7, 2006.

* cited by examiner

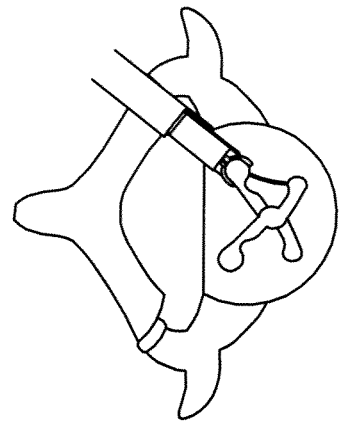
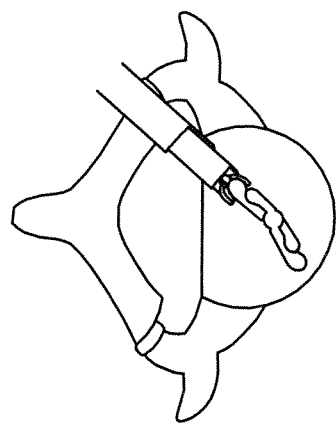
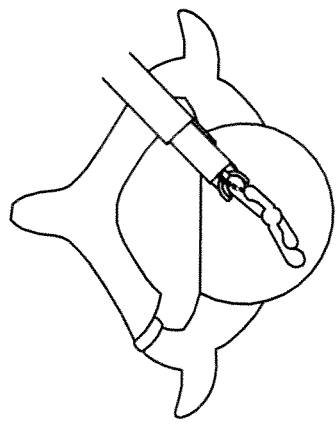
FIG. 48

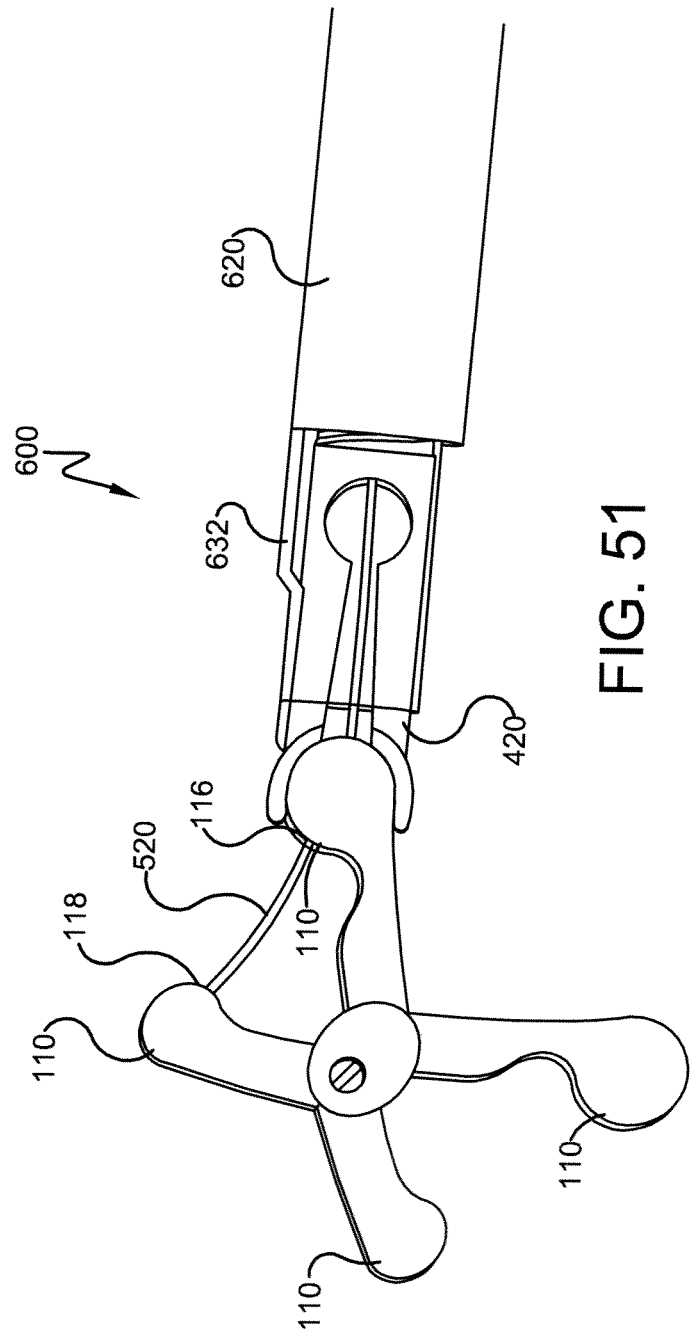

SPINE SURGERY METHOD AND INSERTER

CROSS-REFERENCE TO RELATED APPLICATIONS

This application is a continuation of U.S. patent application Ser. No. 13/448,877, which will issue as U.S. Pat. No. 8,579,977, filed on Apr. 17, 2012, which is a divisional of U.S. patent application Ser. No. 12/108,625 filed on Apr. 24, 2008, now abandoned, both of which are incorporated herein by reference.

I. BACKGROUND OF THE INVENTION

A. Field of Invention

This invention pertains to the art of methods and apparatuses regarding spine surgery and more specifically relates to surgical procedures and an inserter used to position an implant, and perhaps to deploy the implant, within a vertebral space.

B. Description of the Related Art

The volume of spinal surgeries to treat degenerative disc and facet disease has steadily increased over the past decade, fueled by population demographics and advancements in diagnostic and instrumentation adjuncts. Improvements in intraoperative radiological imaging and surgical technique have generated a great deal of interest in applying minimally invasive surgical (MIS) techniques to spinal applications. As in other surgical subspecialties, it is hoped such minimally invasive techniques applied to spinal surgery will result in less soft tissue trauma, less operative blood loss, reduced operative time, faster recovery periods and lower costs.

Known spinal surgical techniques, though generally working well for their intended purposes, have been adopted from traditional open surgical (non-MIS) techniques. As a result, known spinal surgical methods, instrumentation and interbody implants have limitations. One limitation is that the physical components are relatively large and bulky. This reduces surgeon visualization of the surgical site. Another limitation of known spinal surgical methods is that known surgical tools and implants are cumbersome and difficult to maneuver within the limited surgical space available. The limitations of current instrumentation in MIS spine surgery are noted particularly with regards to interbody fusion surgery.

The present invention provides methods and apparatuses for overcoming these limitations by providing a surgical inserter that allows for minimally invasive spinal surgery and that provides for precise movement, placement and deployment of an implant into the vertebral space.

II. SUMMARY OF THE INVENTION

According to one embodiment of this invention, a surgical inserter for use in inserting an implant into a vertebral space comprises: (1) a handle having first and second ends for use by a surgeon; and, (2) an implant gripping mechanism comprising: a gripper having a first end attached to the second end of the handle and a second end having a pair of arms; and, a grip activator having an opening that threadingly receives the gripper. The grip activator can be rotated in a first direction with respect to the gripper to cause the arms to move toward each other to grip the inserter and can be rotated in a second direction with respect to the gripper to cause the arms to move away from each other to release the inserter.

According to another embodiment of this invention, the surgical inserter further comprises: a connector having a first end attached to the second end of the handle and a second end attached to the first end of the gripper.

According to another embodiment of this invention, the surgical inserter further comprises: an implant deployment mechanism for use in deploying the implant.

According to still another embodiment of this invention, the implant deployment mechanism comprises: (1) a compression force member; and, (2) a compression force activator that can apply a force to the compression force member to extend the compression force member into contact with the implant.

According to yet another embodiment of this invention, the implant deployment mechanism comprises: (1) a tension force member that is operatively connected to the implant; and, (2) a tension force activator that can apply a tension force to the tension force member to deploy the implant.

According to another embodiment of this invention, the surgical inserter further comprises: an implant anti-deployment mechanism for use in preventing the implant deployment mechanism from operating until the surgeon is ready to operate it.

According to another embodiment of this invention, the implant anti-deployment mechanism comprises: a tube member that can contact the implant; and, a securing device for use in securing the tube member in contact with the implant to prevent deployment of the implant.

According to still another embodiment of this invention, a method comprises the steps of: (A) providing an implant made to be placed into a vertebral space; (B) providing a surgical inserter comprising: a handle having first and second ends for use by a surgeon; a gripper having a first end attached to the second end of the handle and a second end having a pair of arms; and, a grip activator having an opening in that threadingly receives the gripper; (C) preparing the vertebral space to receive the implant; (D) rotating the grip activator with respect to the gripper to cause the arms to move toward each other to grip the inserter; (E) moving the surgical inserter to insert the implant within the vertebral space; (F) rotating the grip activator with respect to the gripper to cause the arms to move away from each other to release the inserter; and, (G) moving the surgical inserter away from the vertebral space.

According to another embodiment of this invention, the method may further comprise the step of: deploying the implant with the inserter.

According to another embodiment of this invention, the method may further comprise the step of: adjusting an anti-deployment mechanism to permit deployment of the implant.

One advantage of this invention is that the inventive surgical inserter permits an implant to be relatively easily placed into a vertebral space.

Another advantage of this invention is that the implant may be relatively easily and securely attached to the inserter and then detached from the inserter.

Another advantage of this invention is that the surgeon may make consistent and reproducible biplanar, midline placement of the interbody implant.

Another advantage of this invention is that, in one embodiment, the inserter can be used to deploy the implant.

Yet another advantage of this invention is that the surgical inserter allows for minimally invasive deployment via either an anterior, anterolateral, posterior or posterolateral approach, with the latter approach possible via either a transforaminal or extraforaminal approach.

Still other benefits and advantages of the invention will become apparent to those skilled in the art to which it pertains upon a reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof and wherein:

FIG. 48 shows various views of the insertion and deployment of the implant with a 45 degree insertion angle.

FIG. 51 is a close-up top view similar to that shown in FIG. 50 but with the implant shown in the open or deployed condition.

IV. DETAILED DESCRIPTION OF THE INVENTION

Figure 1A:
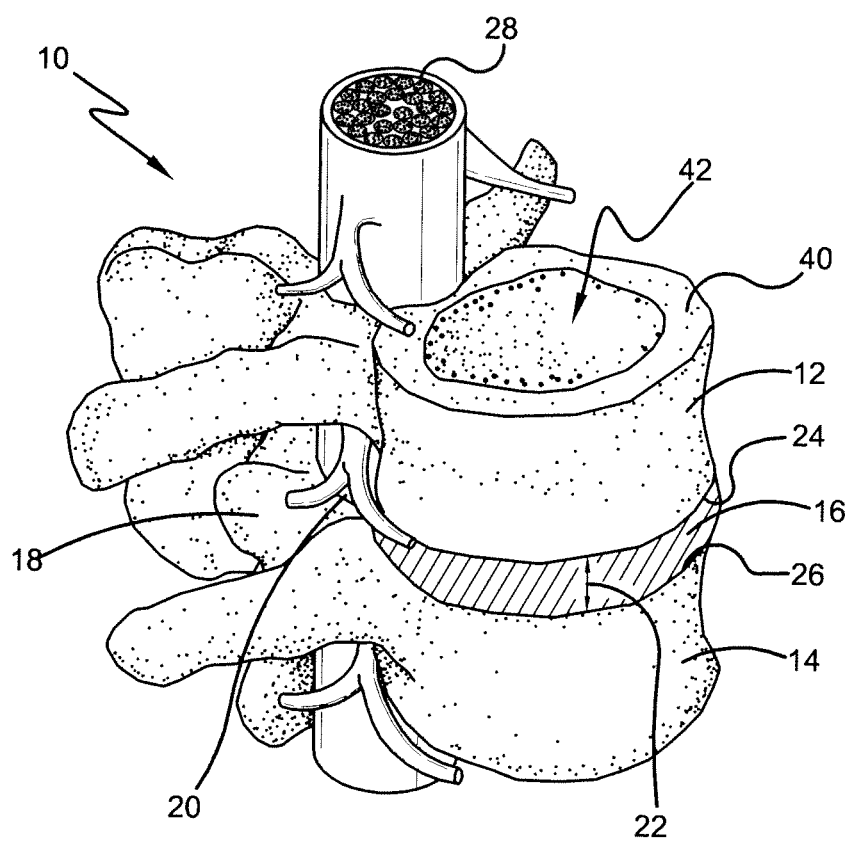
FIG. 1A is a side perspective view of a spinal segment showing a vertebral space defined by the intradiscal space usually occupied by a disc between two adjacent vertebral bodies.
Figure 1B:
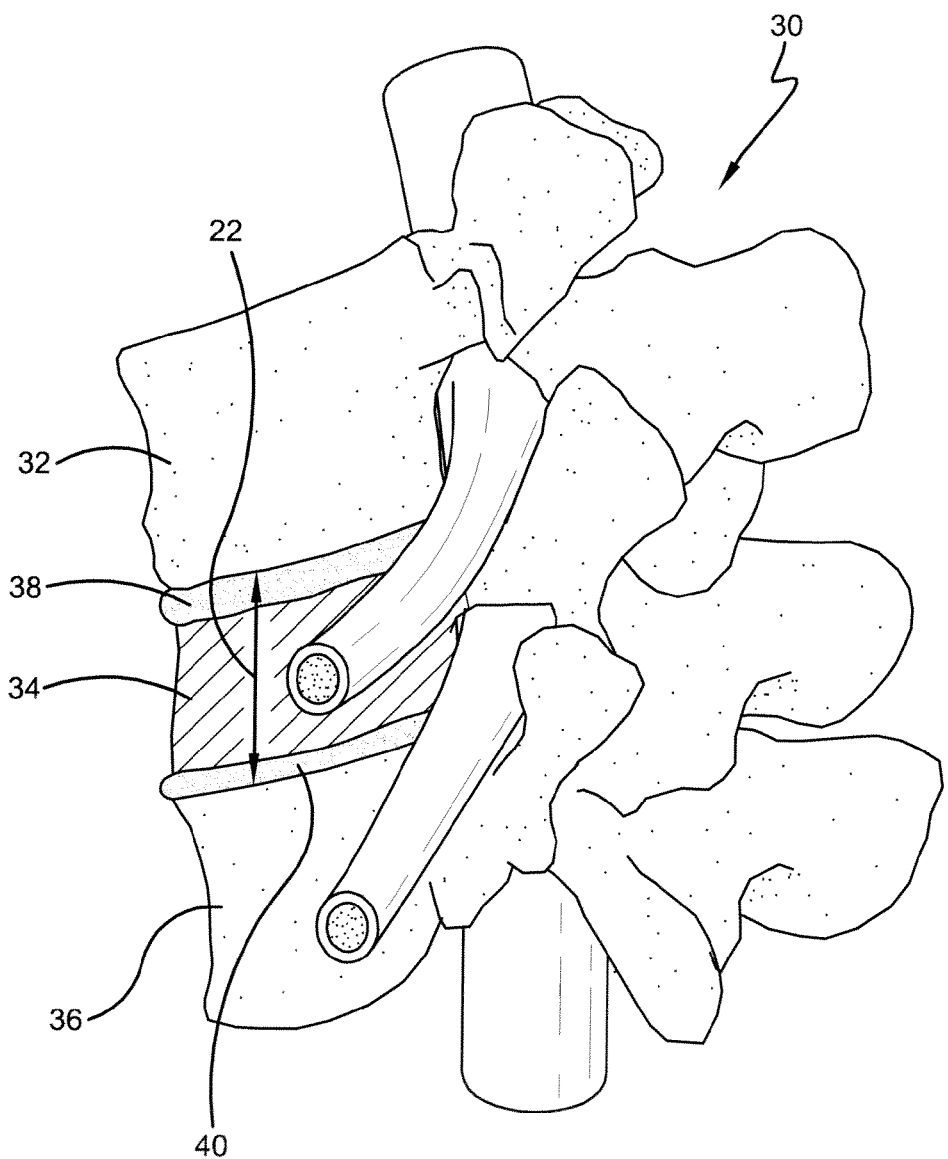
FIG. 1B is a side perspective view of a spinal segment showing a vertebral space defined by the space usually occupied by a vertebral body and its two adjacent discs.
Figure 30:
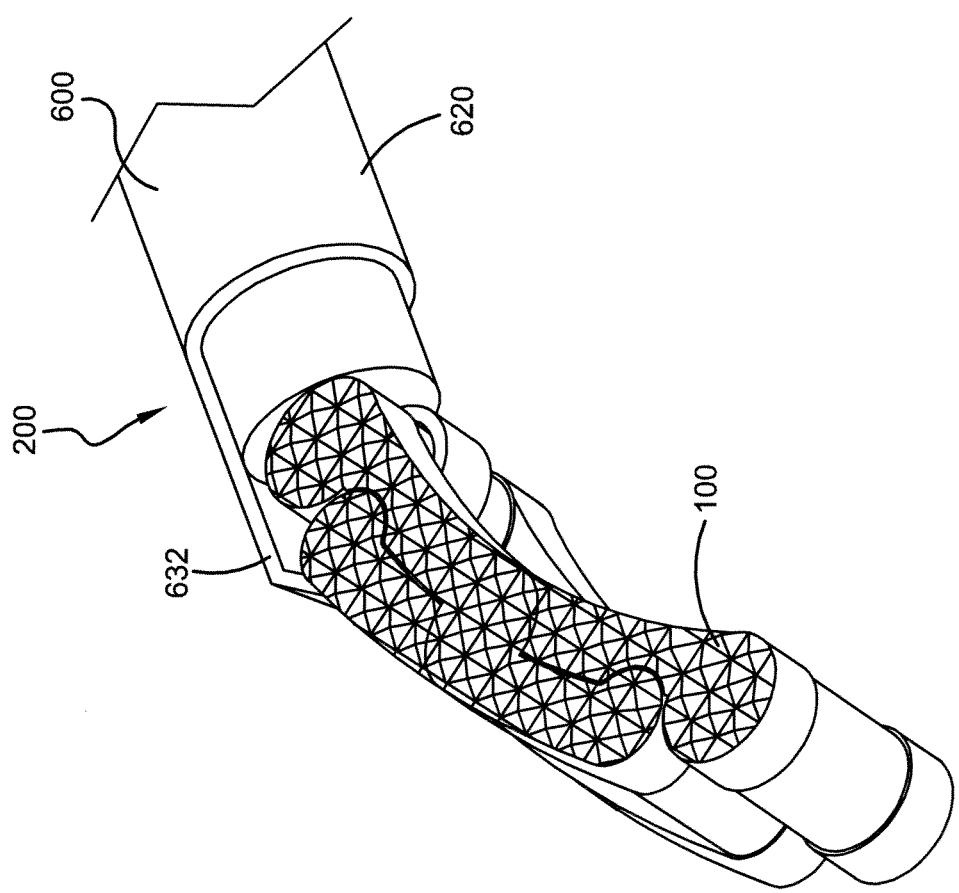
FIG. 30 is a close-up view of the distal end of the inserter showing an attached implant in a non-deployed condition.
Figure 31:
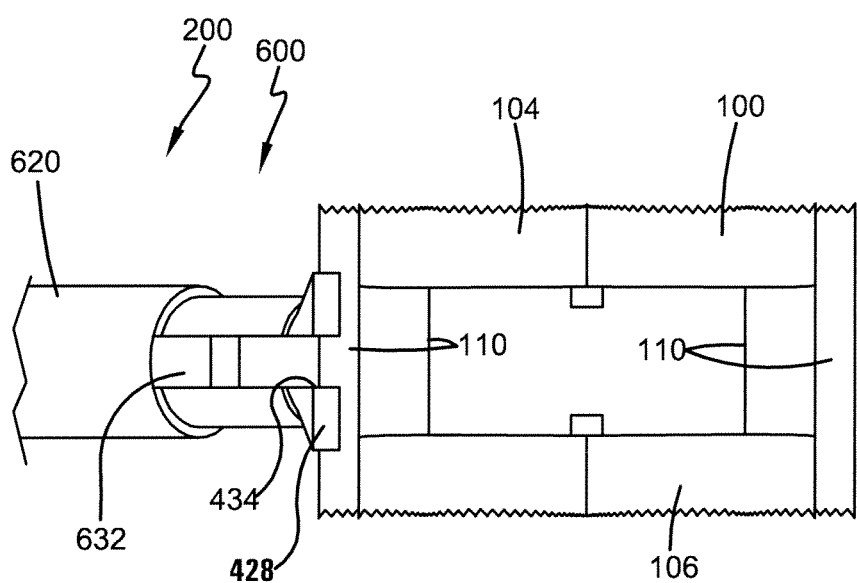
FIG. 31 is a perspective distal end view showing the inserter attached to a deployed implant.

Referring now to the drawings wherein the showings are for purposes of illustrating embodiments of the invention only and not for purposes of limiting the same, the surgical inserter 200 of this invention can be used to insert and, in some embodiments such as shown in FIGS. 30 and 31, deploy an implant 100 into a vertebral space 22. By vertebral space it is meant the space in a spinal column where the implant 100 will be placed. In one embodiment, shown in FIG. 1A, a spinal segment 10 is made up of two vertebrae 12, 14 attached together by ligaments with a disc 16 separating them. Facet joints 18 fit between the two vertebrae 12, 14 and allow for movement. The neural foramen 20 between the vertebrae 12, 14 allow space for the nerve roots to travel freely from the spinal cord 28 to the body. If it is required to remove the disc 16 and replaced it with an implant 100, the space occupied by the disc 16, the intradiscal space between the two adjacent vertebral bodies 12, 14, defines the vertebral space 22. In another embodiment, shown in FIG. 1B, a spinal segment 30 is made up of three vertebrae 32, 34, 36 attached together by ligaments. If it is required to remove the middle vertebra 34 (it is shown diseased) along with the adjacent discs 38, 40, such as may be required because of a corpectomy defect, and replaced them with an implant 100, the space between the two outer vertebral bodies 32, 36, defines the vertebral space 22. It should be understood that these are simply two non-limiting examples of the vertebral space 22 into which an implant 100 can be inserted according to this invention because any vertebral space chosen with the sound judgment of a person of skill in the art can be used. As the components and operation of a spinal column is well known to those of skill in the art, further detail will not be provided here.

Figure 2:
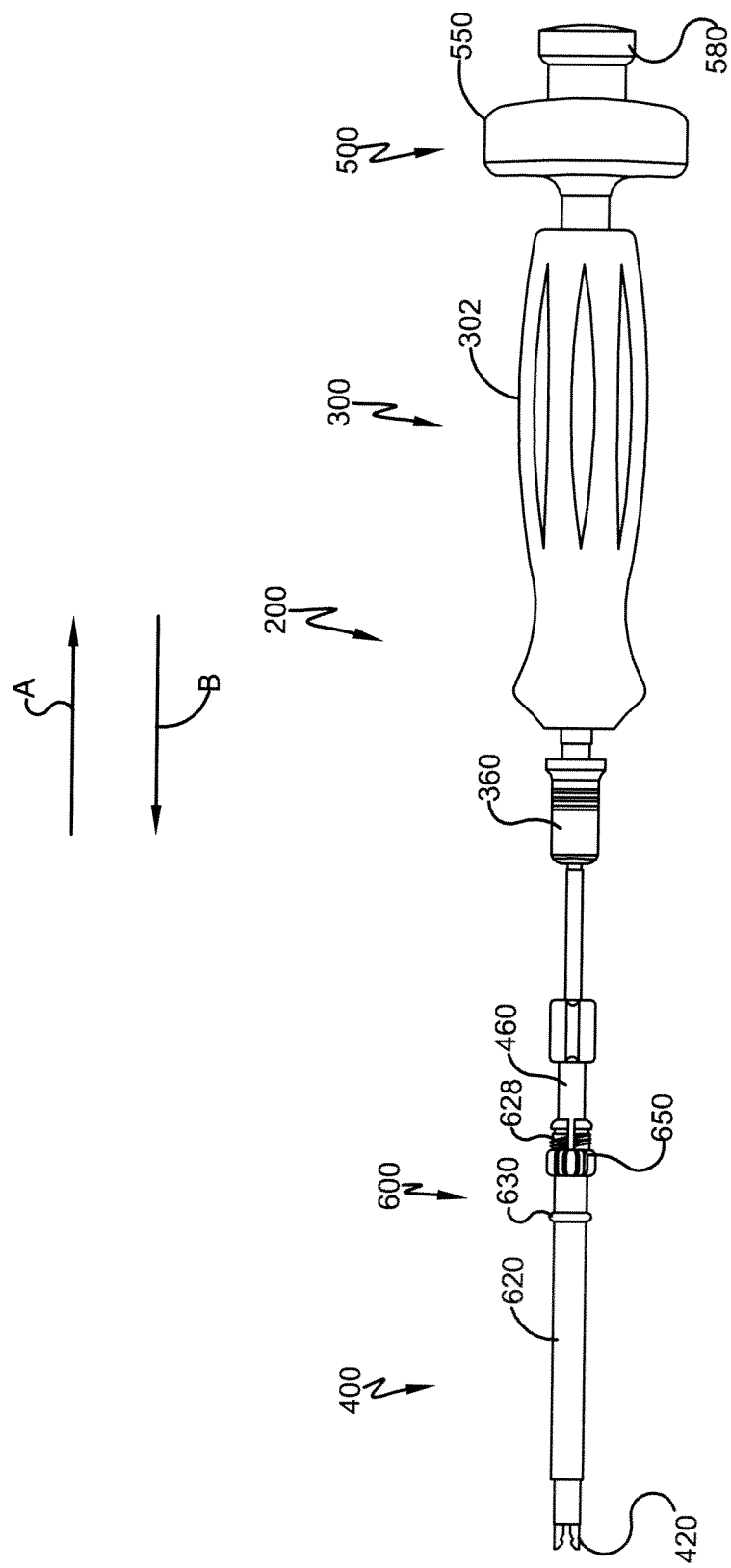
FIG. 2 is a side view of an inserter according to one embodiment of this invention.
Figure 3:
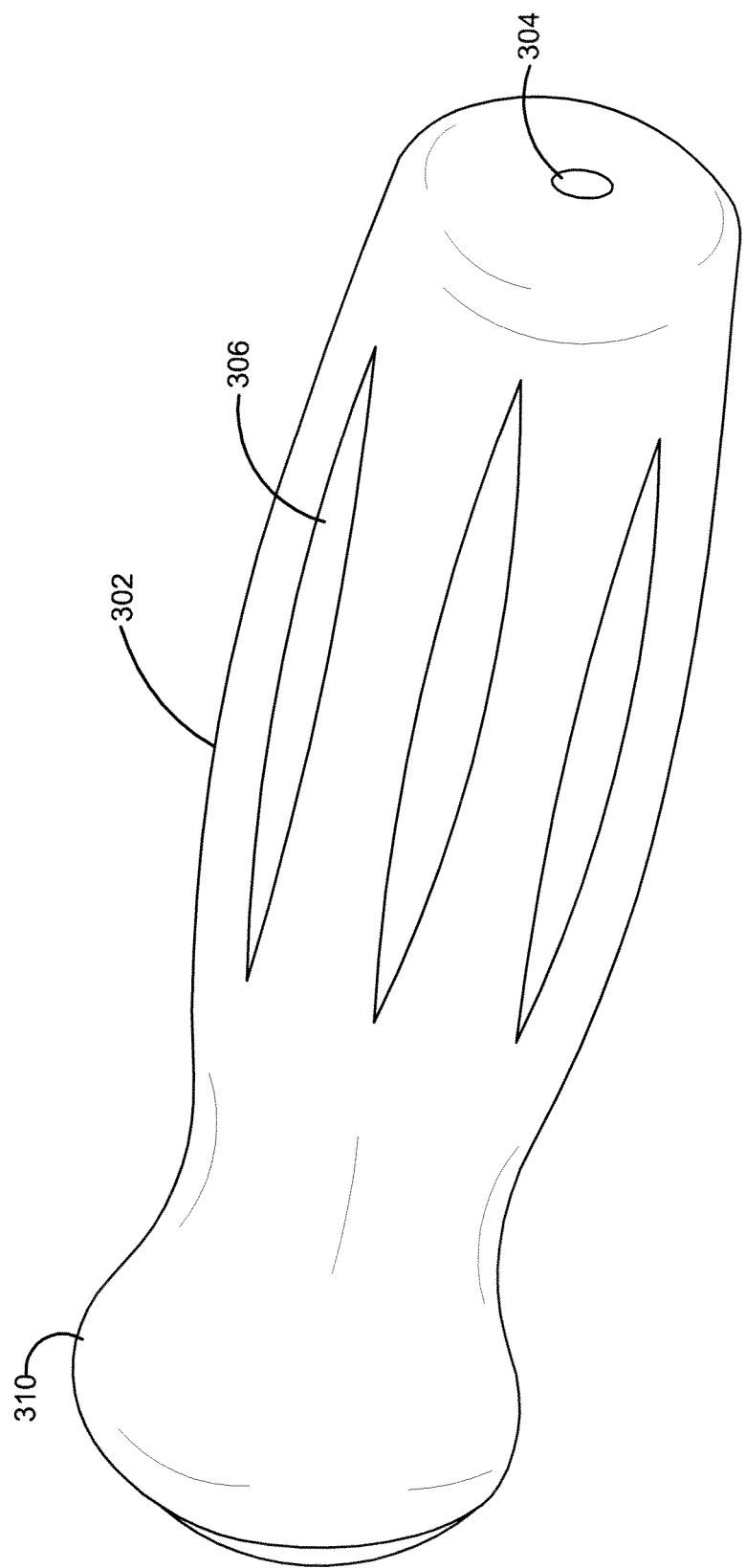
FIG. 3 is a perspective proximal end view of a handle according to one embodiment of this invention.
Figure 4:
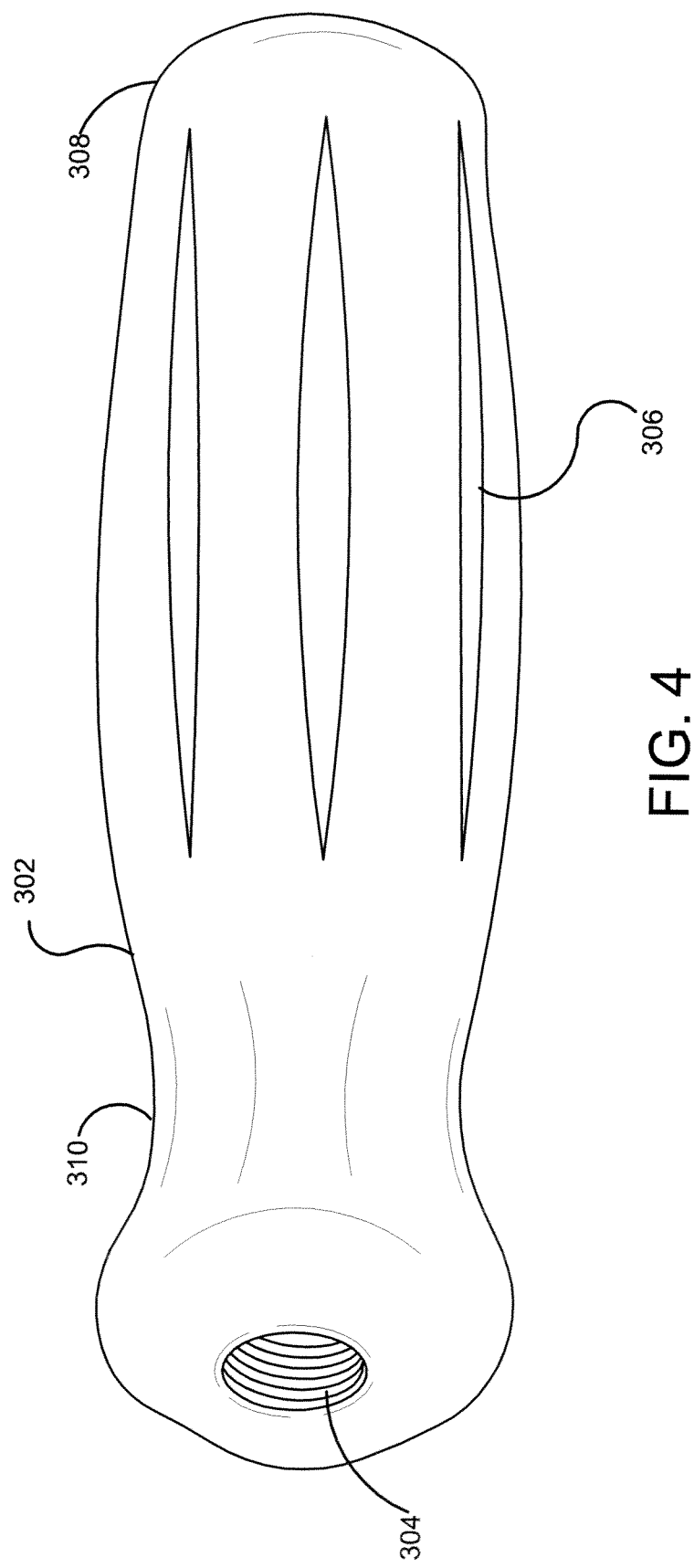
FIG. 4 is a perspective distal end view of the handle shown in FIG. 3.
Figure 5:
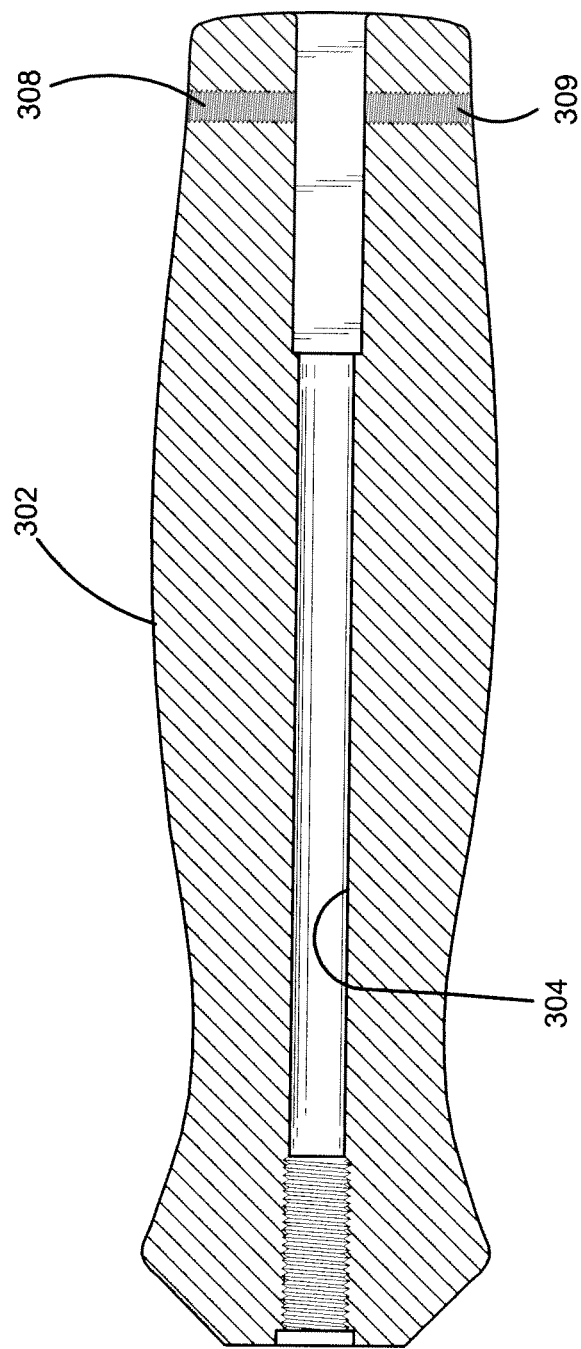
FIG. 5 is a side sectional view of the handle shown in FIG. 3.
Figure 6:
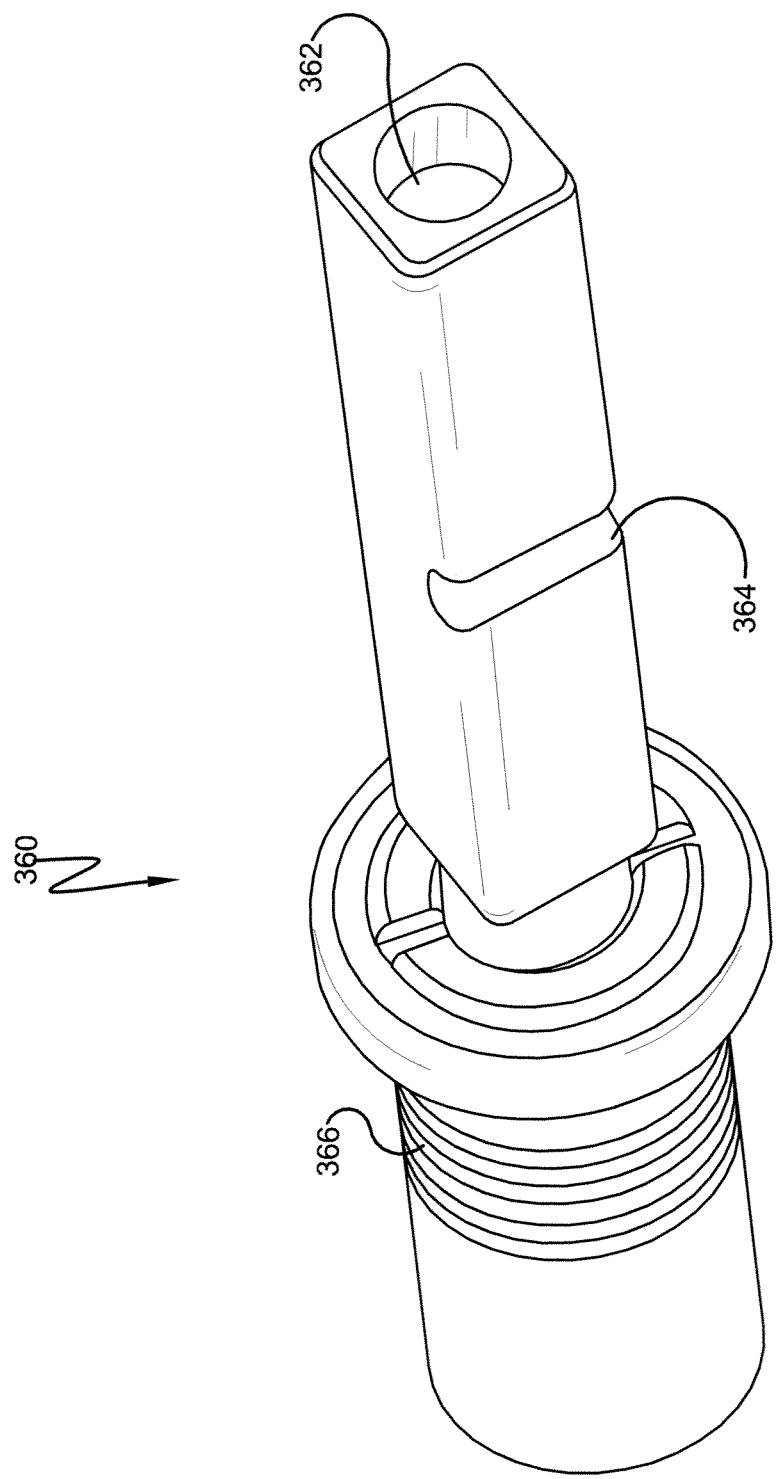
FIG. 6 is a perspective proximal end view of a connector according to one embodiment of this invention.
Figure 7:
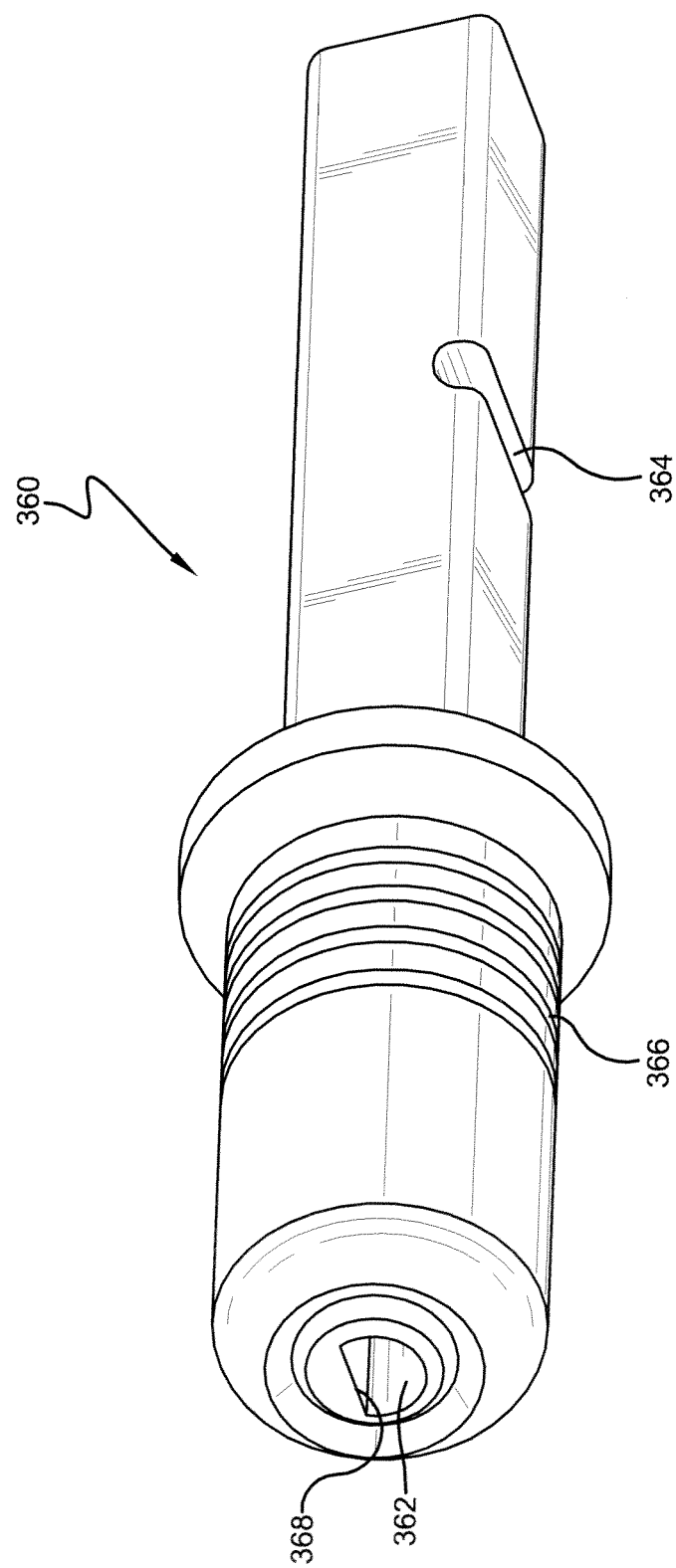
FIG. 7 is a perspective distal end view of the connector shown in FIG. 6.
Figure 8:
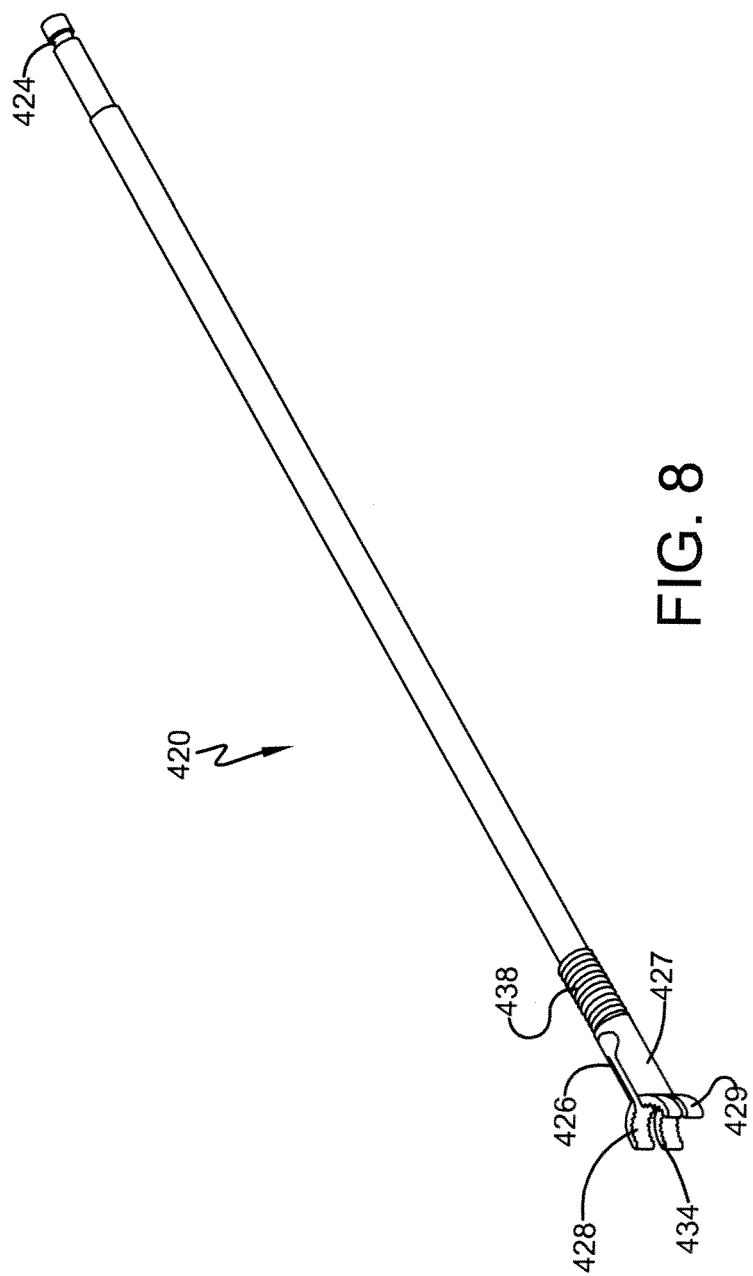
FIG. 8 is a perspective distal end view of a gripper according to one embodiment of this invention.
Figure 9:
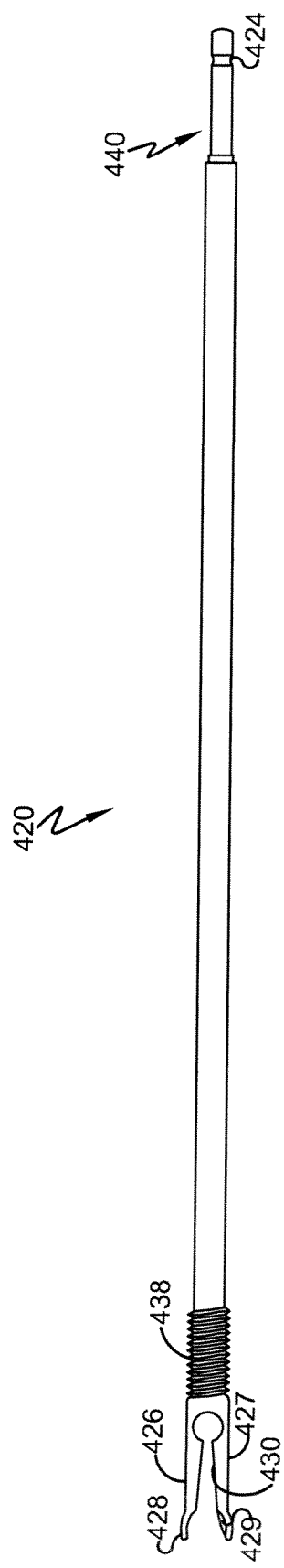
FIG. 9 is a side view of the gripper shown in FIG. 8.
Figure 10:
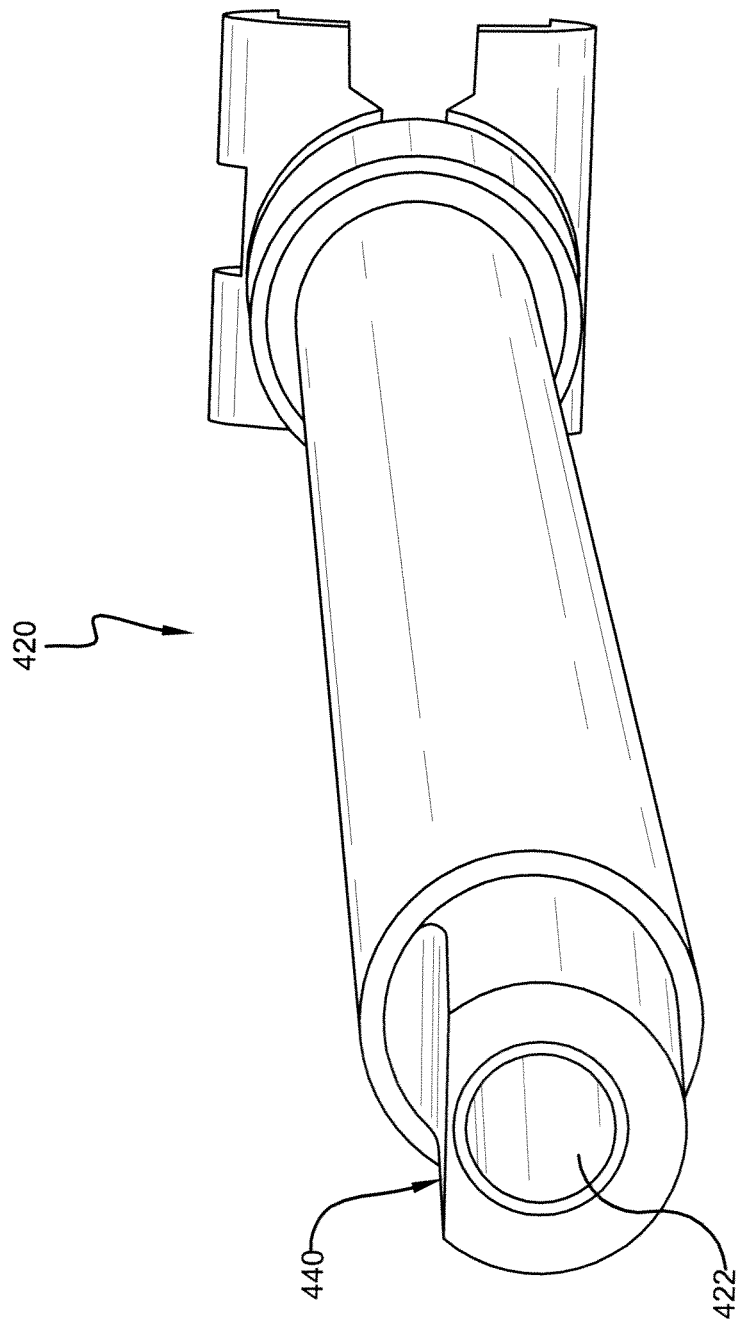
FIG. 10 is a perspective proximal end view of the gripper shown in FIG. 8.
Figure 11:
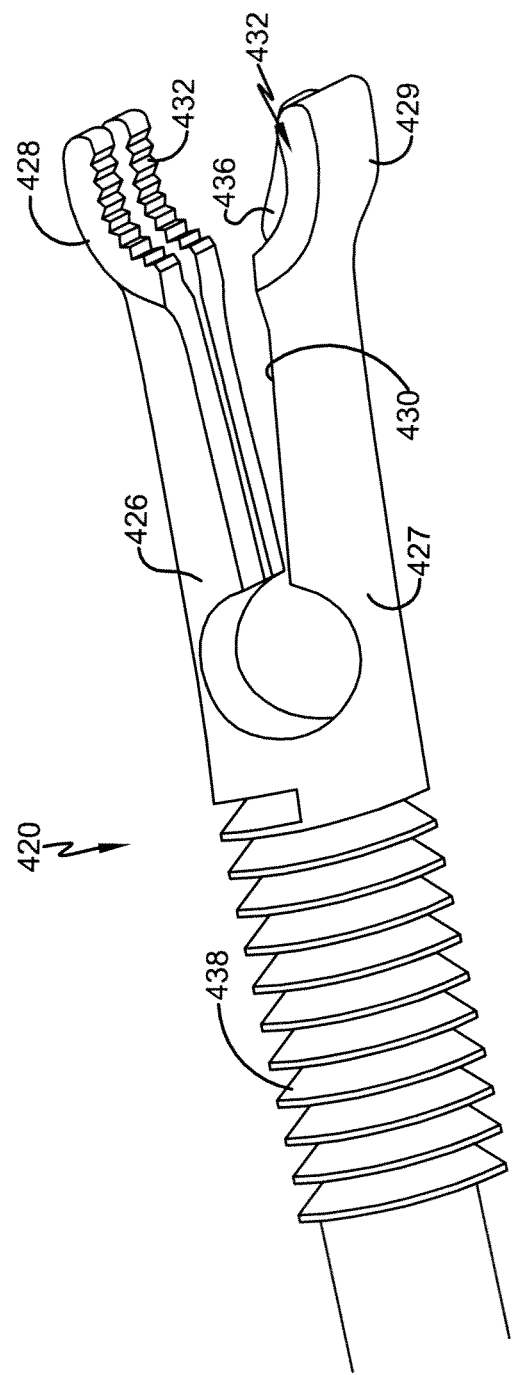
FIG. 11 is a close up perspective view of the distal end of the gripper shown in FIG. 8.
Figure 12:
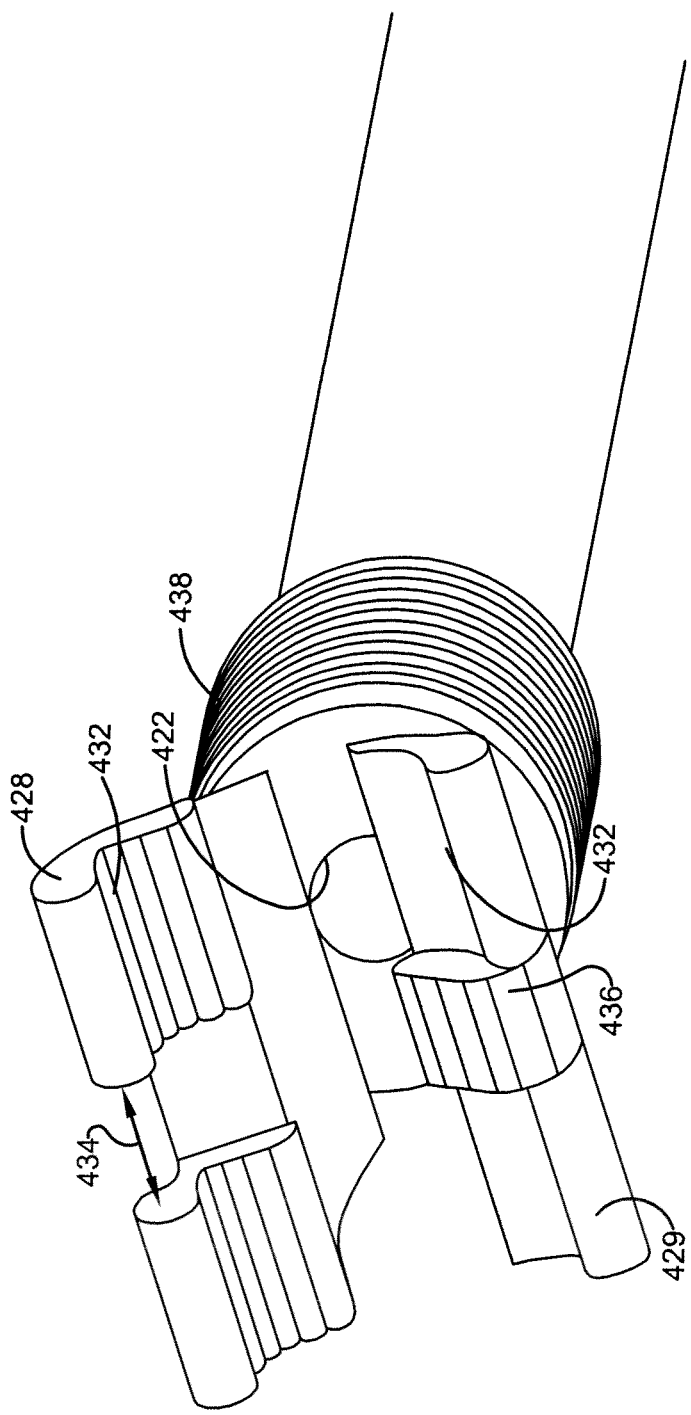
FIG. 12 is a close up perspective distal end view of the gripper shown in FIG. 8.
Figure 13:
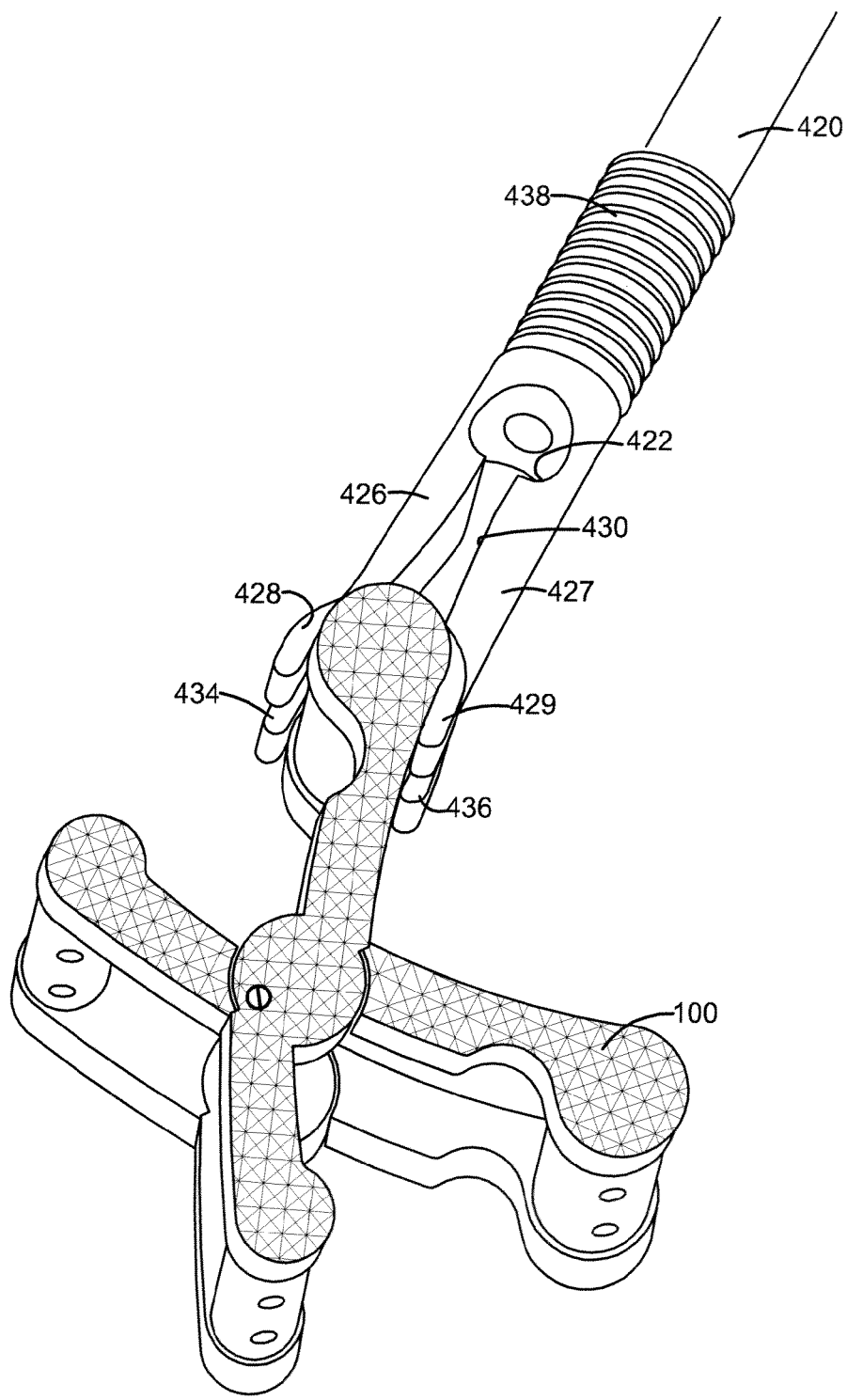
FIG. 13 is a perspective view of the proximal end of the gripper shown in FIG. 8 but showing a deployed implant gripped by the gripper.
Figure 14:
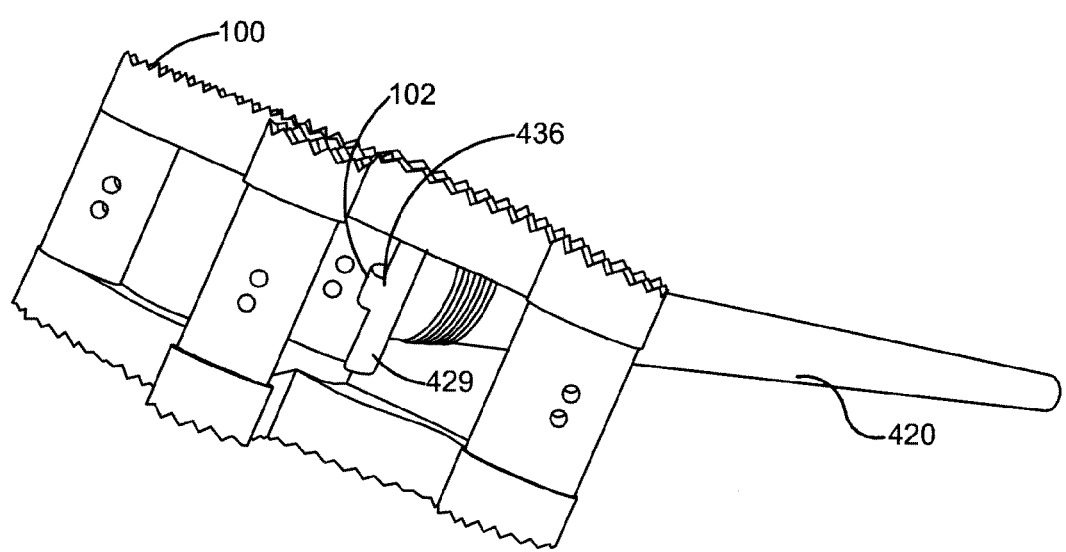
FIG. 14 is a perspective proximal end view of the gripper shown in FIG. 13.
Figure 15:
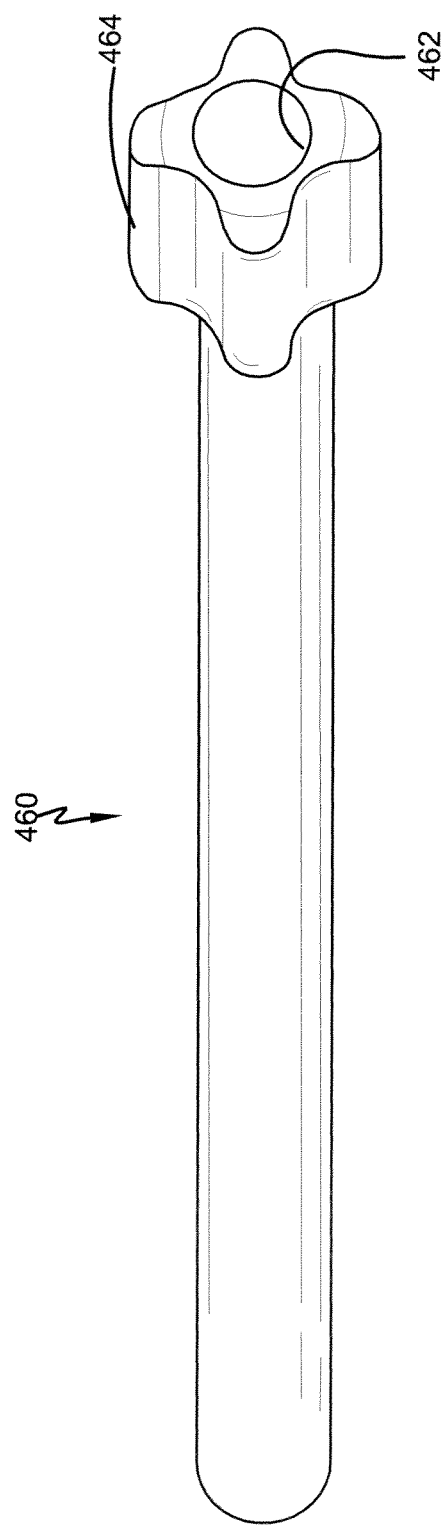
FIG. 15 is a perspective proximal end view of a grip activator according to one embodiment of this invention.
Figure 16A:
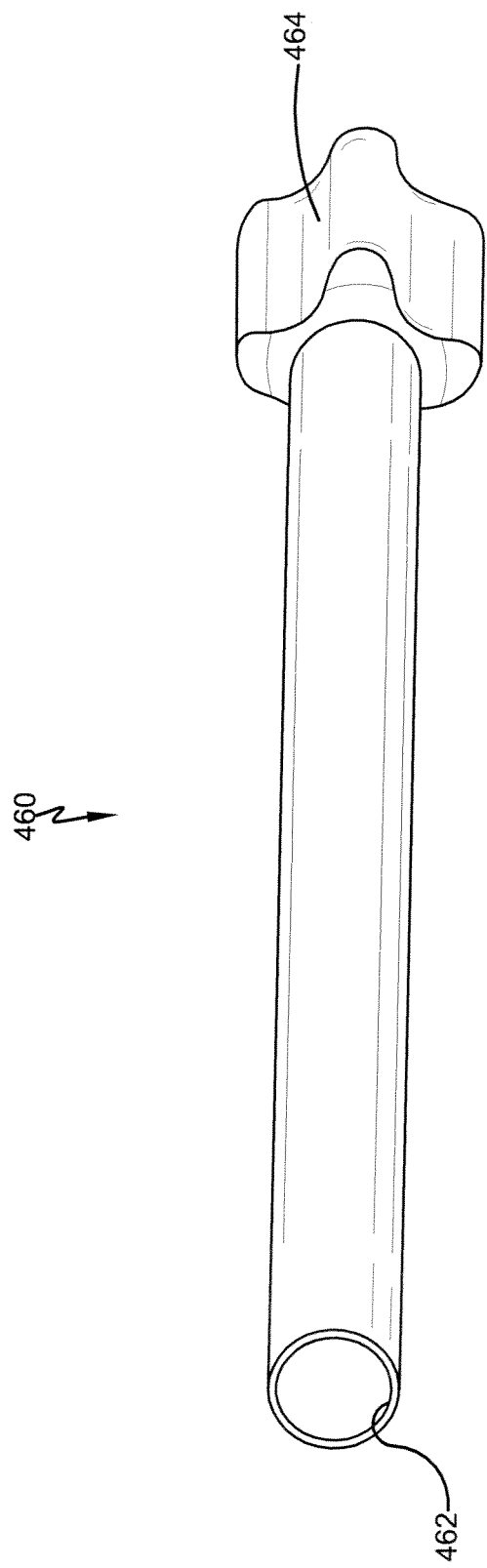
FIG. 16A is a perspective distal end view of the grip activator shown in FIG. 15.
Figure 16B:
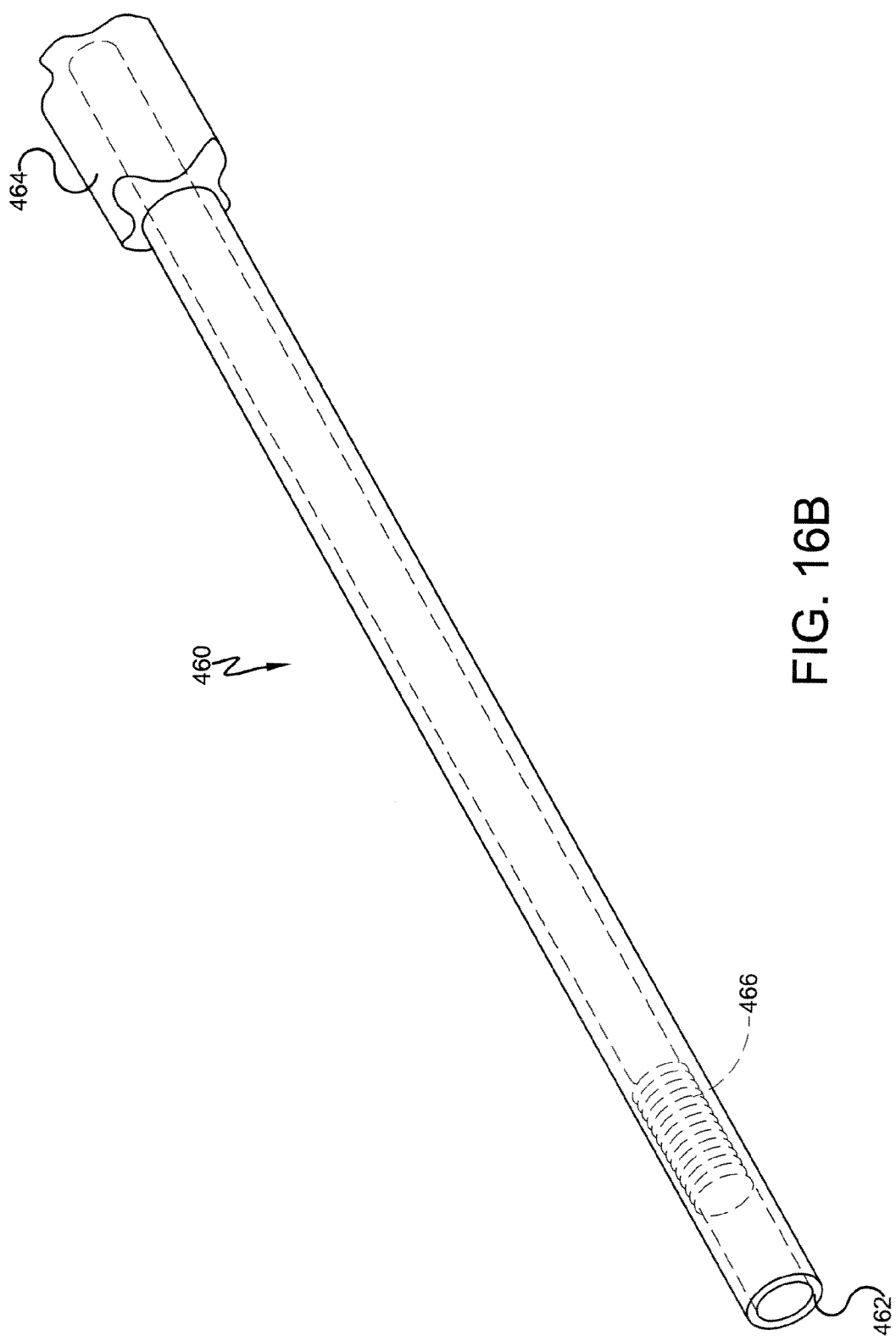
FIG. 16B is a perspective view of the grip activator similar to that shown in FIG. 15 but shown as if transparent so that the thread region can be seen.
Figure 17:
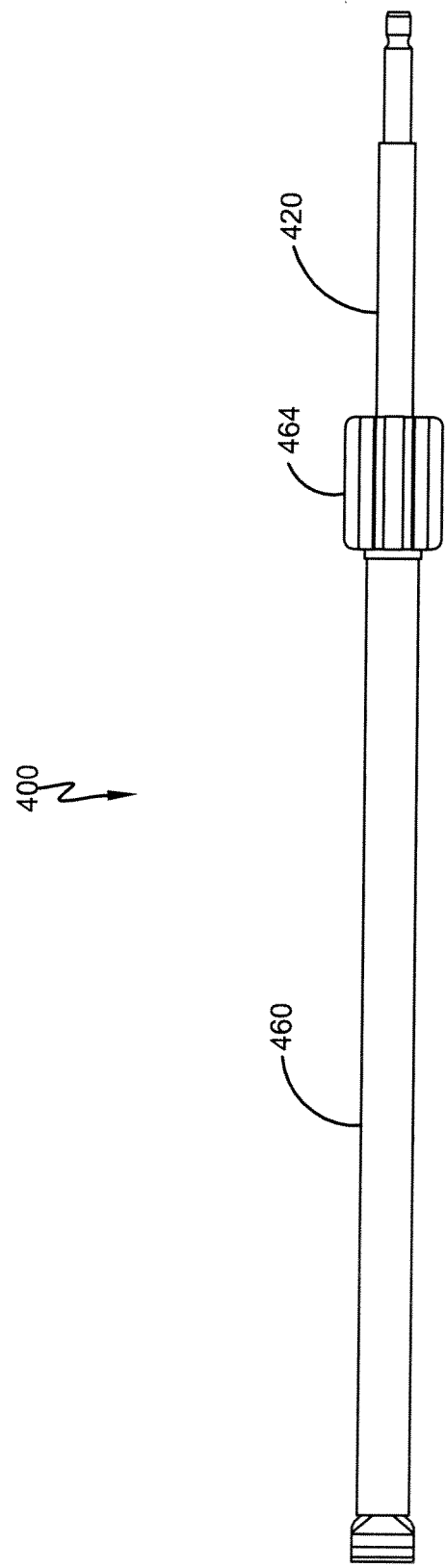
FIG. 17 is a side view of the gripper being received by the grip activator.

With reference now to FIG. 2, the inserter 200 of this invention in some embodiments may include a handle mechanism 300, an implant gripping mechanism 400, an implant deployment mechanism 500, and an implant anti-deployment mechanism 600. Each of these mechanisms will be described in more detail below. Note that throughout this patent the term "proximal" shall refer to direction A as shown in FIG. 2 (toward the handle end of the inserter) and the term "distal" shall refer to direction B as shown in FIG. 2 (toward the implant end of the inserter). These terms are not used to limit this invention in any way but only to provide a direction reference.

With reference now to FIGS. 2-5 the handle mechanism 300 includes a handle 302 that may be held by the surgeon and used to manipulate the inserter 200 during surgery. The handle 302 may be generally cylindrical and may have an opening 304 throughout its length. This opening 304 can be used for purposes described below and may be positioned substantially in the radial center of the handle 302. The outer surface of the handle 302 may be contoured along the handle length, as shown, and may have a textured region 306 to improve the grip for the surgeon. The proximal end of the handle 302 may be adapted to attach to the implant deployment mechanism 500 and may include a pair of proximal holes 308, 309 for this purpose. The distal end may be adapted to attach to the implant gripping mechanism 400 and may include a distal hole 310 for this purpose.

With reference now to FIGS. 2 and 4-7, while in one embodiment the implant gripping mechanism 400 attaches directly to the distal end of the handle 302, for the embodiment shown the handle mechanism 300 includes a connector 360. A connector provides for ease of assembly; namely a "quick connect" type attachment and may also make it easier to clean the inserter components. The connector 360 may have an opening 362 throughout its length for purposes described below and may be positioned substantially in the radial center of the connector 360. The proximal end of the connector 360 may have a generally rectangular cross-section and may be adapted to attach to the distal end of the handle 302. A groove 364 may be formed in the connector 360, as shown. While the groove 364 is shown on one side of the connector 360 it is to be understood that this groove could be positioned elsewhere and could, in another embodiment, be replaced with a hole extending through the connector 360. To attach the connector 360 to the handle 302, the proximal end of the connector 360 is inserted into the opening 304 at the distal end of the handle 302 until the connector groove 364 and the handle distal hole 310 are aligned. A dowel pin (not shown) may then be inserted through the distal hole 310 and groove 364 to secure the connector 360 to the handle 302. In one embodiment, shown, the substantially square cross-section of the proximal end of the connector 360, when received within the substantially circular cross-section of the opening 304 in the distal end of the handle 302, helps to prevent relative motion and thereby helps to maintain the inserter components in proper position as the inserter 200 is used.

With continuing reference to FIGS. 2 and 4-7, the distal end of the connector may be generally cylindrical and may have an outer surface that is contoured along the connector length and may have a textured region 366 to improve the grip for the surgeon. The distal end may be adapted to attach to the implant gripping mechanism 400 and the distal end of the opening 362 may have a specific shape for this purpose. The opening shape shown has a cross-section that is semi-circular with a flat edge 368 but it is to be understood that the opening shape can be any chosen with the sound judgment of a person of skill in the art in order to attach to the implant gripping mechanism 400.

With reference now to FIGS. 2 and 7-14, the implant gripping mechanism 400, which is used to grip and release the implant 100, will now be described. The implant gripping mechanism 400 includes a gripper 420 that may be generally cylindrical and may have an opening 422 throughout its length. This opening 422 can be used for purposes described below and may be positioned substantially in the radial center of the gripper 420. The proximal end of the gripper 420 may be adapted to attach to the distal end of the connector 360. More specifically, the proximal end of the gripper 420 may be shaped to fit into the distal end of the opening 362 formed in the connector 360. For the embodiment shown, the proximal end of the gripper 420 has a cross-section that is semi-circular with a flat edge 440 to match the opening 362. To further secure the proximal end of the gripper 420 to the distal end of the connector 360, the gripper 420 may have a circumferential groove 424 that is received in a mating extension (not shown) that extends from the opening 362 within the connector 360.

With continuing reference to FIGS. 2 and 7-14, the distal end of the gripper 420 may be used to both grip and release the implant 100. A pair of arms 426, 427, forming a V-shape, may extend outwardly and end with a pair of hands 428, 429, respectively, as shown. There is a space 430 between the arms 426, 427 which can be narrowed as will be described further below. Each hand 428, 429 has a contact surface 432 that is used to physically contact a surface of the implant 100. As shown, one hand 428 has a gap 434 between two hand portions for a purpose to be described below. However, other embodiments would also work well with this invention. Neither hand, for example, may have a gap. In another embodiment, three or more hand portions may be used. The contact surface of each hand portion may be textured, as shown, to improve the gripping characteristics of the hands 428, 429. The other hand 429 may have a continuous contact surface 432 and may include a tang 436 positioned substantially central to the hand, as shown. The tang 436 is also used to improve the gripping characteristics of the hands 428, 429. In one specific embodiment, the tang 436 is adapted to be received within a corresponding groove 102 (see FIG. 14) formed in the implant. In other embodiments, multiple tangs and/or multiple grooves may be used. It should be understood that the contact surfaces 432 described here are non-limiting examples because the contact surfaces 432 used can be any chosen with the sound judgment of a person of skill in the art. Positioned proximally from the arms 426, 427 the outer surface of the gripper 420 has a threaded region 438 for purposes to be described below.

With reference now to FIGS. 2 and 11-18, the implant gripping mechanism 400, may also include a grip activator 460 which can be used by the surgeon to activate the gripper 420 to grip or release the implant 100. The grip activator 460 may be generally cylindrical and may have an opening 462 throughout its length. This opening 462 may be positioned substantially in the radial center of the grip activator 460 and may be used to receive the gripper 420, as shown. The proximal end of the grip activator 460 may have an outer surface having a textured region 464 to improve the grip for the surgeon. The distal end of the grip activator 460 may be adapted to attach to and activate the gripper 420. In a specific embodiment, the opening 462 may be at least partially defined by a threaded region 466 (see FIGS. 16B and 18) that engages the threaded region 438 of the gripper 420, for purposes to be described below.

With reference now to FIGS. 2, 30 and 31, the implant deployment mechanism 500, which is used to deploy an implant will now be described. First, however, it should be noted that the term "deploy" as used in this patent refers to any adjustment of an implant after the implant has been initially placed into the vetebral space that involves relative motion of one portion of the implant with respect to another portion of the implant. Non-limiting examples of deployment include implants that have one portion that pivots or moves curvilinearly with respect to another portion and implants that have one portion that slides or moves linearly with respect to another portion. Implants that expand in any manner and in any direction fall under the definition of "deploy." Second it should be noted that not all implants may require deployment. If this is the case, it should be noted that the inserter 200 of this invention as described above will work well to insert such an implant. Third, it should be noted that the inventors contemplate multiple devices and methods for deploying an implant. While specific embodiments will be described, they should not be understood to be limiting but rather exemplary only.

With reference now to FIGS. 2, 13, 20A, 20B, 32-33 and 50-51, in one embodiment a compression force is used to deploy the implant 100. In this case, a compression force member may be used to "push" or "shove" the implant 100 for deployment. In one specific embodiment, the compression force member is a rigid rod or wire 520 that is positioned within the handle opening 304, the connector opening 362, and the gripper opening 422. To deploy the implant 100 it is only necessary to apply a compression force to the proximal end of the wire 520 causing the wire 520 to move in the distal direction B until the distal end of the wire 520 extends out of the distal end of the gripper 420 and contacts the implant 100 for deployment, as shown for example in FIGS. 32 and 50. This compression force can be activated by the surgeon using a compression force activator 700.

Figure 20A:
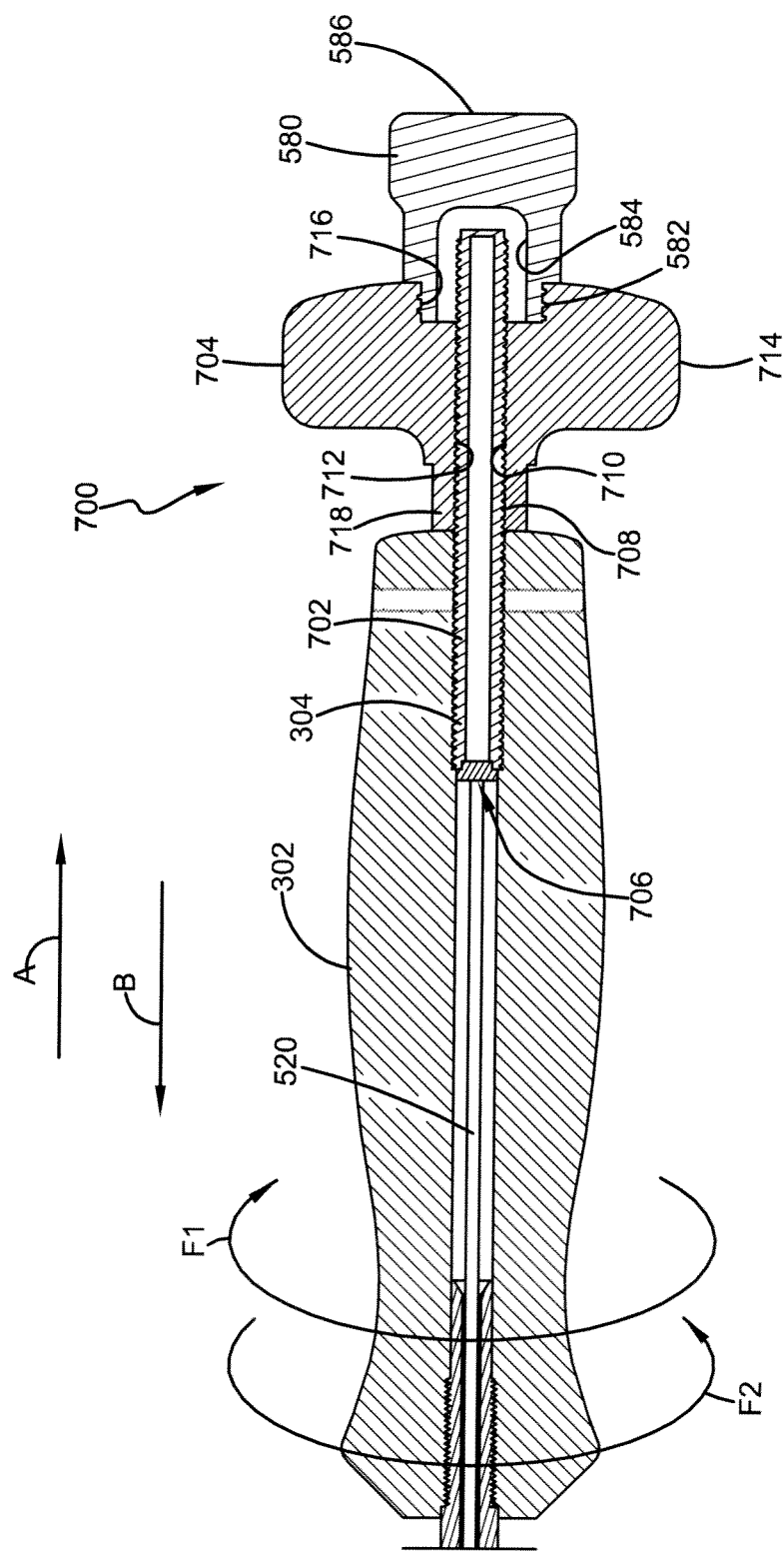
FIG. 20A is a side sectional view of the handle, the screw, a compression knob and a cap according to one embodiment of this invention.

With reference now to FIGS. 2, 13, 20A, 20B, 32 and 33, in one embodiment, shown in FIG. 20A, the compression force activator 700 includes a screw 702 and a compression knob 704. The screw 702 may be generally cylindrical and may have a contact surface 706 at its distal end that is used to contact and move the compression force member 520. The screw 702 may also have an opening 720 throughout its length substantially in the radial center of the screw 702 that receives the compression force member 520. The outer surface of the screw 702 may have a threaded region 708 to engage the compression knob 704 as will be described below. While the threaded region 708 is shown to substantially cover the entire outer surface of the screw 702, it is to be understood that the threaded region 708 need not be that big. It is only necessary for the threaded region 708 to be sufficient in size to accomplish the purpose of this invention as determined with the sound judgment of a person of skill in the art. The distal end of the screw 702 may be inserted into the handle opening 304 on the proximal end of the handle 302 and may, in a more specific embodiment, threadably engage threads formed on the inside diameter of the proximal end of the handle opening 304. In an alternate embodiment, the proximal end of the handle opening 304 does not include threads that engage the threaded region 708 of the screw 702.

With reference now to FIGS. 2, 19, 20A and 23, the compression knob 704 may be used by the surgeon to increase or decrease compression force on the compression force member 520 during surgery. The compression knob 704 may be generally cylindrical and may have an opening 710 throughout its length that may be positioned substantially in the radial center of the compression knob 704. The compression knob 704 may have a threaded region 712 defining at least a portion of the outer edge of the opening 710 to engage with the threaded region 708 of the screw 702. The outer surface of the compression knob 704 may be contoured along the compression knob length, as shown, and may have a textured region 714 to improve the grip for the surgeon. The proximal end of the compression knob 704 may be adapted to attach to a cap 580 as will be described further below. More specifically, the compression knob 704 may have a second threaded region 716 defining at least a portion of the outer edge of the opening 710 (which may have a greater diameter, as shown) to engage with a threaded region 582 of the cap 580. The distal end of the compression knob 704 may be adapted to engage the proximal end of the screw 702. More specifically, the distal end of the compression knob 704 may include a "nut-like" portion 718 having an outer surface that is substantially shaped as a typical nut used to receive a bolt. Rotation of the compression knob 704 in a first direction F1 causes the screw 702 to move in the distal direction B with respect to the handle 302 until the contact surface 706 of the screw 702 contacts the proximal end of the compression force member 520. Continued rotation of the compression knob 704 in the first direction F1 causes the screw 702 and the compression force member 520 to move in the distal direction B so that the distal end of the compression force member 520 can contact the implant 100. Rotation of the compression knob 704 in a second direction F2 causes the screw 702 to move in the proximal direction A and reduces the force on the compression force member 520. For this embodiment, the compression knob 704 does not move distally or proximally with respect to the handle 302 as it is rotated.

With reference now to FIGS. 2, 19, 20A and 23-25, in one embodiment the previously mention cap 580 may be used with the inserter 200 of this embodiment. The cap 580 may be generally cylindrical and may have an opening 584 extending partially through its length that may be positioned substantially in the radial center of the cap 580. The outer surface of the cap 580 may be contoured along the cap length, as shown. The proximal end of the cap 580 may have an outer surface 586 that is adapted to receive a direct force from a surgical mallet, slap hammer or the like for use in positioning the inserter 200. For this reason the cap 580 is preferably centered on the longitudinal axis of the inserter 200. It should be noted, however, that the cap 580 can be positioned anywhere chosen with the sound judgment of a person of skill in the art. The distal end of the cap 580 may be adapted to receive the proximal end of the screw 532 and to attach to the proximal end of the compression knob 704. In a specific embodiment, the distal end of the cap 580 may have an outer surface with a threaded region 582 that engages the second threaded region 716 of the compression knob 704. The opening 584 may receive the proximal end of the screw 702 as the compression knob 704 is rotated as explained above. It should also be noted that the cap 580 can be easily removed to access the screw 702 and the compression force member 520 for loading and removal of the compression force member 520 from the implant 200.

Figure 20B:
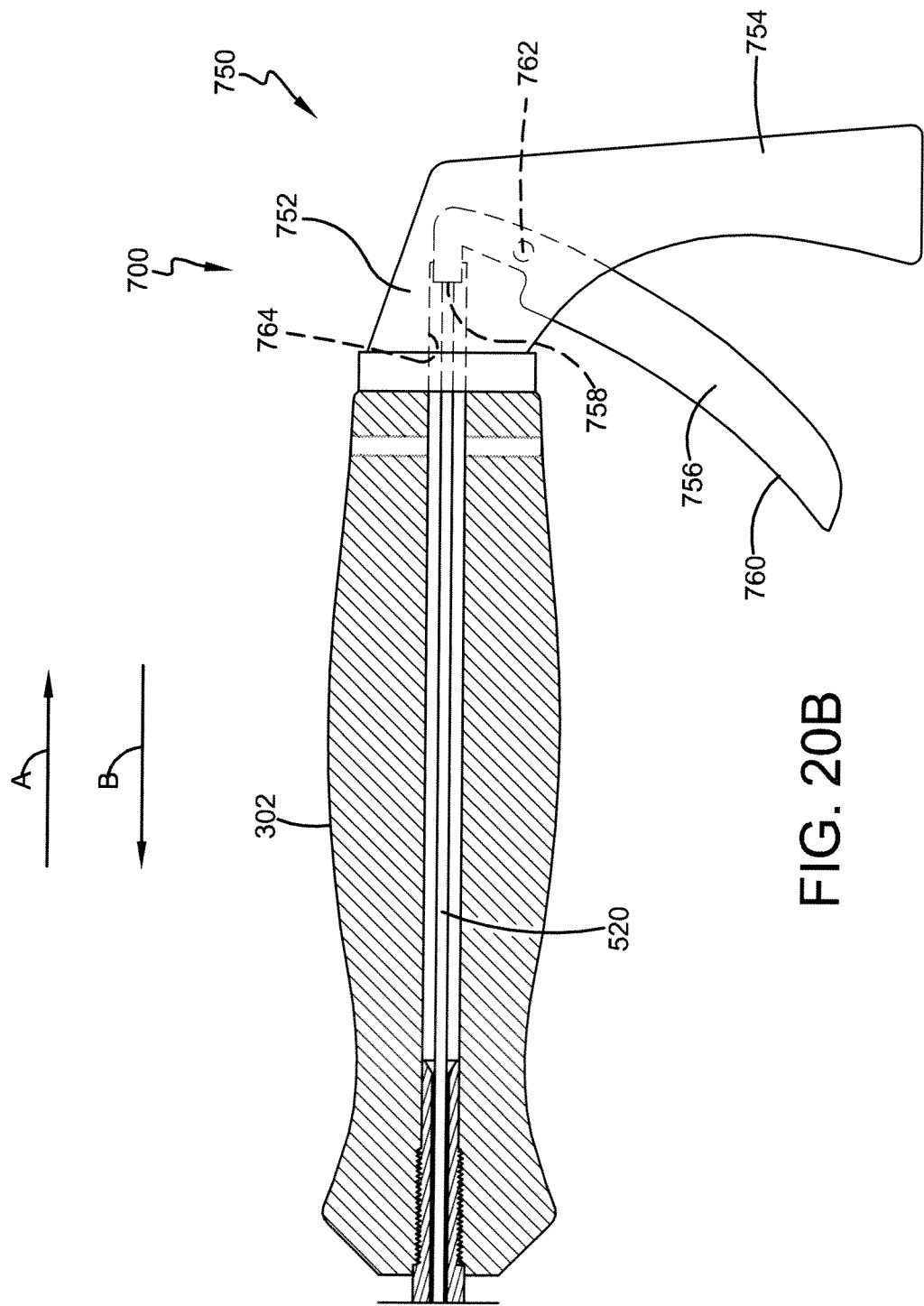
FIG. 20B is a side sectional view of the handle and a side view of a compression trigger mechanism according to one embodiment of this invention.

With reference now to FIGS. 20B, 32-33 and 50-51, in another embodiment shown in FIG. 20B, the compression force activator 700 is a compression trigger mechanism 750. The compression trigger mechanism 750 may include a body 752, a hold member 754 and a trigger 756. The trigger 756 may have a contact surface 758 at a first end that is used to contact and move the compression force member 520. At the second end, the trigger 756 may have a grip surface 760. Between its ends, the trigger 756 may be pivotally connected, such as with a pivot pin 762, to the body 752 or to the hold member 754. The distal end of the body 752 may be connected to the proximal end of the handle 302 in any manner chosen with the sound judgment of a person of skill in the art. The body 752 may have an opening 764 that is collinear with the opening 304 formed in the handle 302. To increase the compression force on the compression force member 520 during surgery, the surgeon simply places the hold member 754 in his/her palm, places his/her fingers on the grip surface 760 of the trigger 756 and squeezes. This squeezing causes the second end of the trigger 756 to move in proximal direction A and to thus pivot the trigger 756 about pivot pin 762. This motion in turn causes the contact surface 758 to move in distal direction B until the contact surface 758 contacts the proximal end of the compression force member 520. Continued squeezing of the trigger 756 causes the compression force member 520 to move in the distal direction B so that the distal end of the compression force member 520 can contact the implant 100.

With reference now to FIGS. 2, 13, 19, 20C and 34-46, in another embodiment a tension force is used to deploy the implant 100. In this case, a tension force member may be used to "pull" on some portion of the implant 100 for deployment. In one specific embodiment, the tension force member is a cable 560 that is positioned within the handle opening 304, the connector opening 362, and the gripper opening 422. To deploy the implant 100 it is only necessary to apply a force to the proximal end of the cable 560 causing the cable 560 to move in the proximal direction A until the desired motion occurs at the implant 100. This tension force can be activated by the surgeon using a tension force activator 530. In one embodiment, the tension force activator 530 includes a screw 532 and a tension knob 550. The screw 532, as seen best in FIGS. 19 and 20C, may be generally cylindrical and may have an opening 534 throughout its length substantially in the radial center of the screw 532 that receives the cable 560. The outer surface of the screw 532 may have a threaded region 536 to engage the tension knob 550 as will be described below. While the threaded region 536 is shown to substantially cover the entire outer surface of the screw 532, it is to be understood that the threaded region 536 need not be that big. It is only necessary for the threaded region 536 to be sufficient in size to accomplish the purpose of this invention as determined with the sound judgment of a person of skill in the art. The screw 532 may also have one or more spherical radii 538 (four used in the shown embodiment).

With reference now to FIGS. 2, 5, 19 and 20C, the distal end of the screw 532 may be inserted into the handle opening 304 on the proximal end of the handle 302. At least one ball plunger 540 (two used in the shown embodiment) may be inserted into the proximal holes 308, 309 formed in the proximal end of the handle 302. Each ball plunger 540 engages one of the spherical radii 538 to secure the screw 532 to the handle 302 in a manner known in the art. The proximal end of the screw 532 may extend out of the handle 302 and engage the tension knob 550 as will be described below.

With reference now to FIGS. 2, 19, 20C and 23, the tension knob 550 may be used by the surgeon to increase or decrease tension force on the cable 560 during surgery. The tension knob 550 may be generally cylindrical and may have an opening 552 throughout its length that may be positioned substantially in the radial center of the tension knob 550. The tension knob 550 may have a threaded region 554 defining at least a portion of the outer edge of the opening 552 to engage with the threaded region 536 of the screw 532. The outer surface of the tension knob 550 may be contoured along the tension knob length, as shown, and may have a textured region 556 to improve the grip for the surgeon. In one embodiment, the proximal end of the tension knob 550 may be adapted to attach to the cap 580. More specifically, the tension knob 550 may have a second threaded region 558 defining at least a portion of the outer edge of the opening 552 (which may have a greater diameter, as shown) to engage with a threaded region 582 of the cap 580. The cap 580 can be easily removed to access the tension force member 560. The distal end of the tension knob 550 may be adapted to engage the proximal end of the screw 532. More specifically, the distal end of the tension knob 550 may include a "nut-like" portion 559 having an outer surface that is substantially shaped as a typical nut used to receive a bolt.

With reference now to FIGS. 2, 19, 20C, 49A, 49B and 49C, the tension force member, which may be cable 560, may be attached to the implant deployment mechanism 500 in any manner chosen with the sound judgment of a person of skill in the art. In one embodiment, the cable 560 is attached to the screw 532. In one more specific embodiment shown in FIG. 49A, a set screw 800 may be received in a hole formed in the proximal end of the screw 532. The proximal end of the cable 560 can be wrapped around the set screw 800 and the set screw 800 can then be tightened to the screw 532 to secure the cable 560. For one embodiment using both cable 560 ends or in another embodiment where two cables 560 are used, a pair of set screws 800, 800 may be used to secure the cable(s) as shown. In another embodiment shown in FIG. 49B, one or more collars 802 may be attached to the screw 532. A cable end is then inserted through an opening 804 in the collar 802 and the collar 802 is rotated to tighten against the cable 560, to secure the cable 560, in a manner known in the art. In yet another embodiment shown in FIG. 49C, a reel device 806 may be attached to the screw 532. A cable end is then received on and rotated about the reel device 806 to secure the cable 560 in a manner known in the art. While the previous discussed concerned various embodiments for attaching the cable 560 to the screw 532, it should be understood that the same embodiments could also be used to attach the cable 560 to another portion of the inserter 200, such as to the tension knob 550. It should also be understood that while the set screw 800, collar 802 and reel device 806 where described as receiving one cable end, they each could receive multiple cable ends or non-end portions of the cable 560. In this case, only one set screw 800, collar 802 or reel device 806 is required even if multiple cables or cable portions are secured to the implant deployment mechanism 500.

Figure 19:
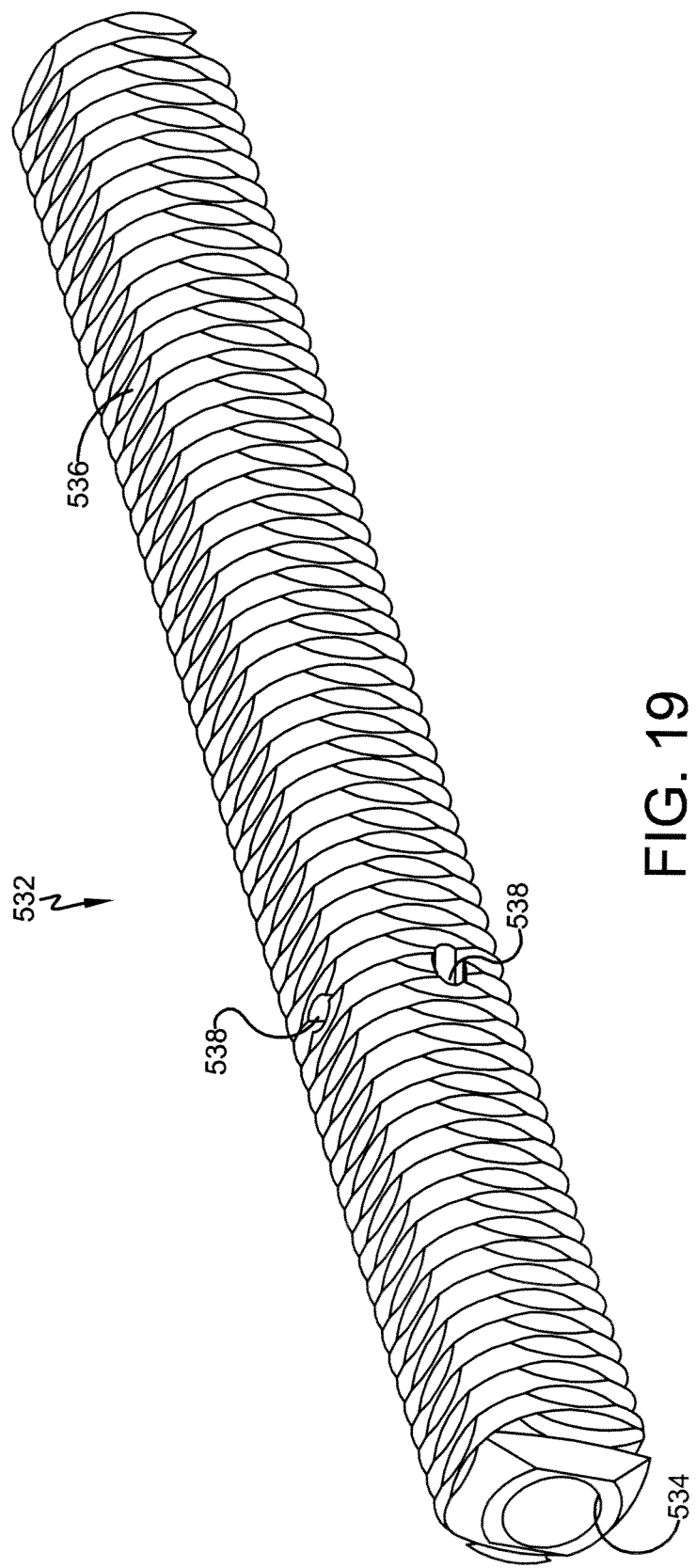
FIG. 19 is a perspective distal end view of a screw according to one embodiment of this invention.
Figure 20C:
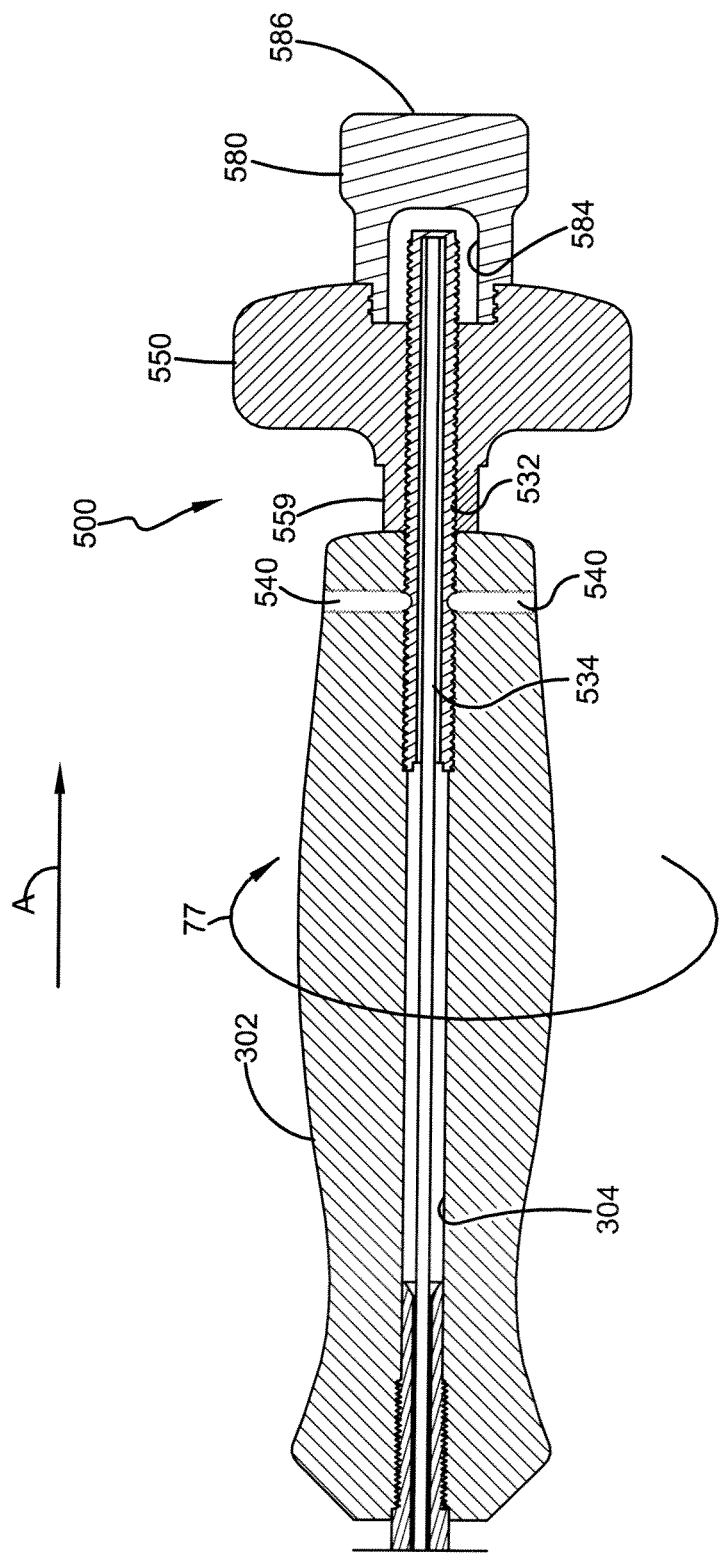
FIG. 20C is a side sectional view of the handle, the screw, a tension knob and a cap according to one embodiment of this invention.
Figure 20D:
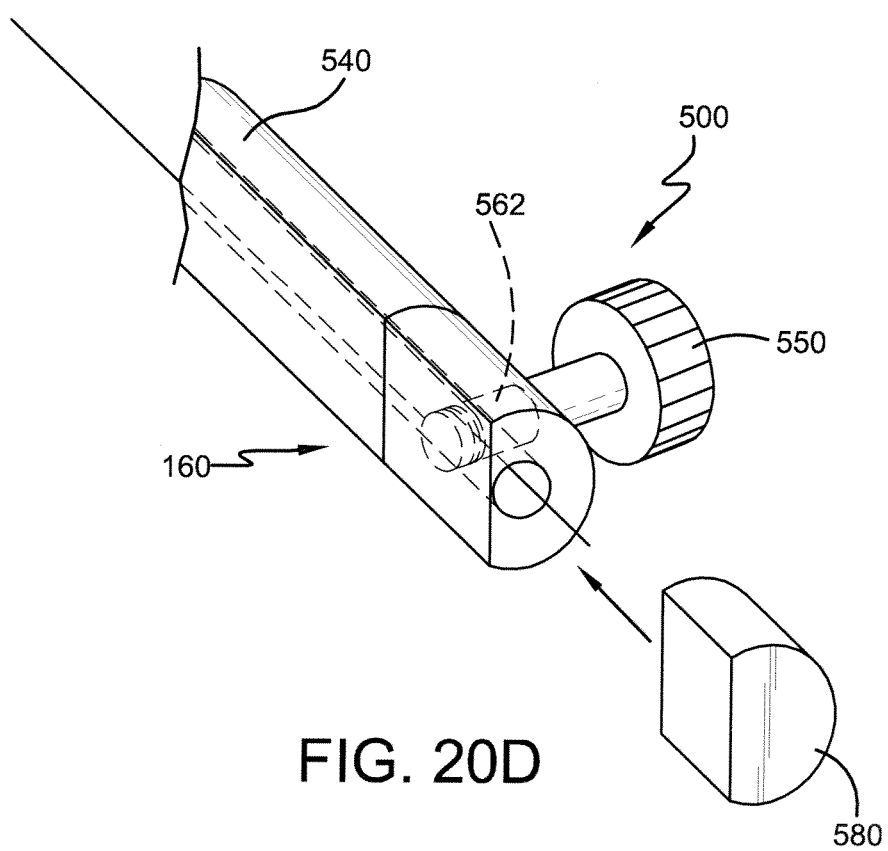
FIG. 20D is a perspective sectional view of the handle, a tension knob and a cap according to another embodiment of this invention.

With reference now to FIGS. 19 and 20D, in another embodiment the tension knob 550 may be used without the previously described screw 532. The tension knob 550 may be attached to a rotatable shaft 562 that can be rotated by the tension knob 550 and about which the cable 560 can be wound. The tension knob 550 may extend laterally from the inserter 200, as shown. The tension knob 550 may, in one embodiment, be ratcheted so that successive turns of the tension knob 550 increase the tension on the cable 560. In yet another embodiment, the implant deployment mechanism 500 may include an axle/cam mechanism (not shown). The surgeon may choose from a series of suture or cabling materials that have diameters allowing passage through the inserter 200 and cable receiving holes in the implant 100. Each of these materials has an intrinsic tensile strength with differing loads to failure. In one embodiment, the implant deployment mechanism 500 may be calibrated to match the various tensile strengths of the suture/cabling material. In a more specific embodiment, the tension knob 550 may be designed to provide audible sounds, "clicks" for example. As the tension knob 550 is rotated, it may provide a first audible sound that signifies that the implant 100 has been deployed. As the tension knob 550 is rotated further, it may provide a second audible sound that signifies that the cabling material is about to fail.

Figure 20E:
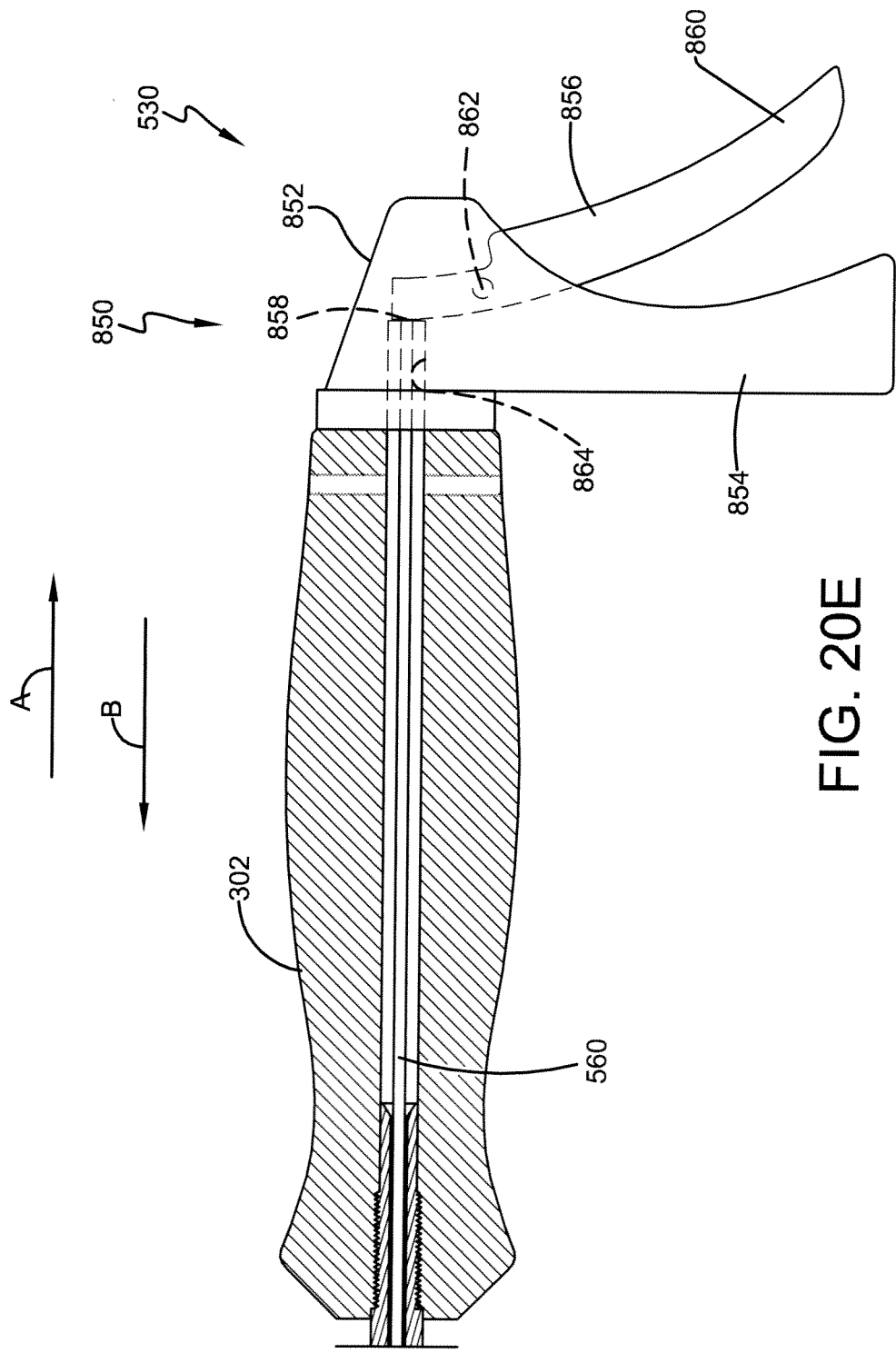
FIG. 20E is a side sectional view of the handle and a side view of a tension trigger mechanism according to one embodiment of this invention.
Figure 21:
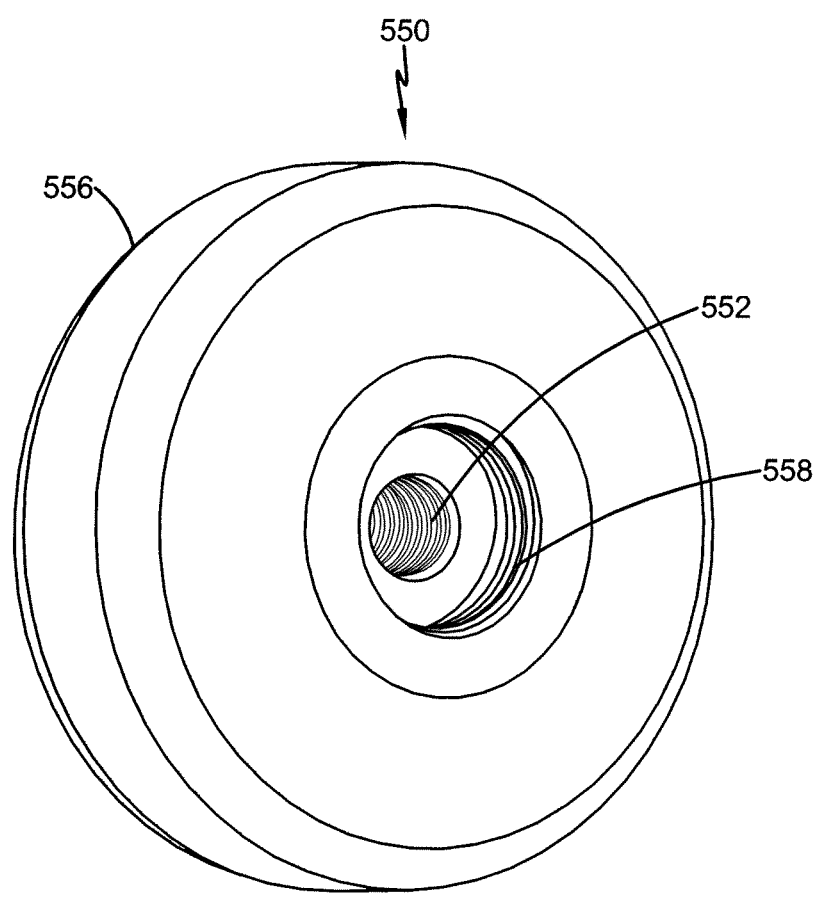
FIG. 21 is a perspective proximal end view of the tension knob according to one embodiment of this invention.
Figure 22:
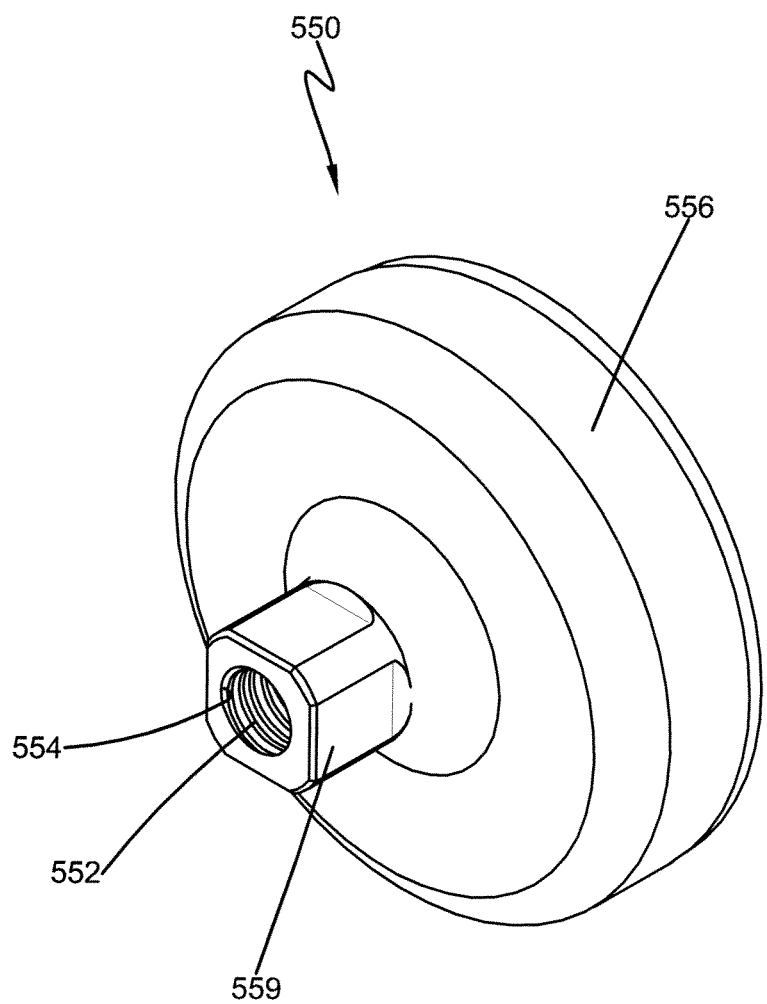
FIG. 22 is a perspective distal end view of the tension knob shown in FIG. 21.
Figure 23:
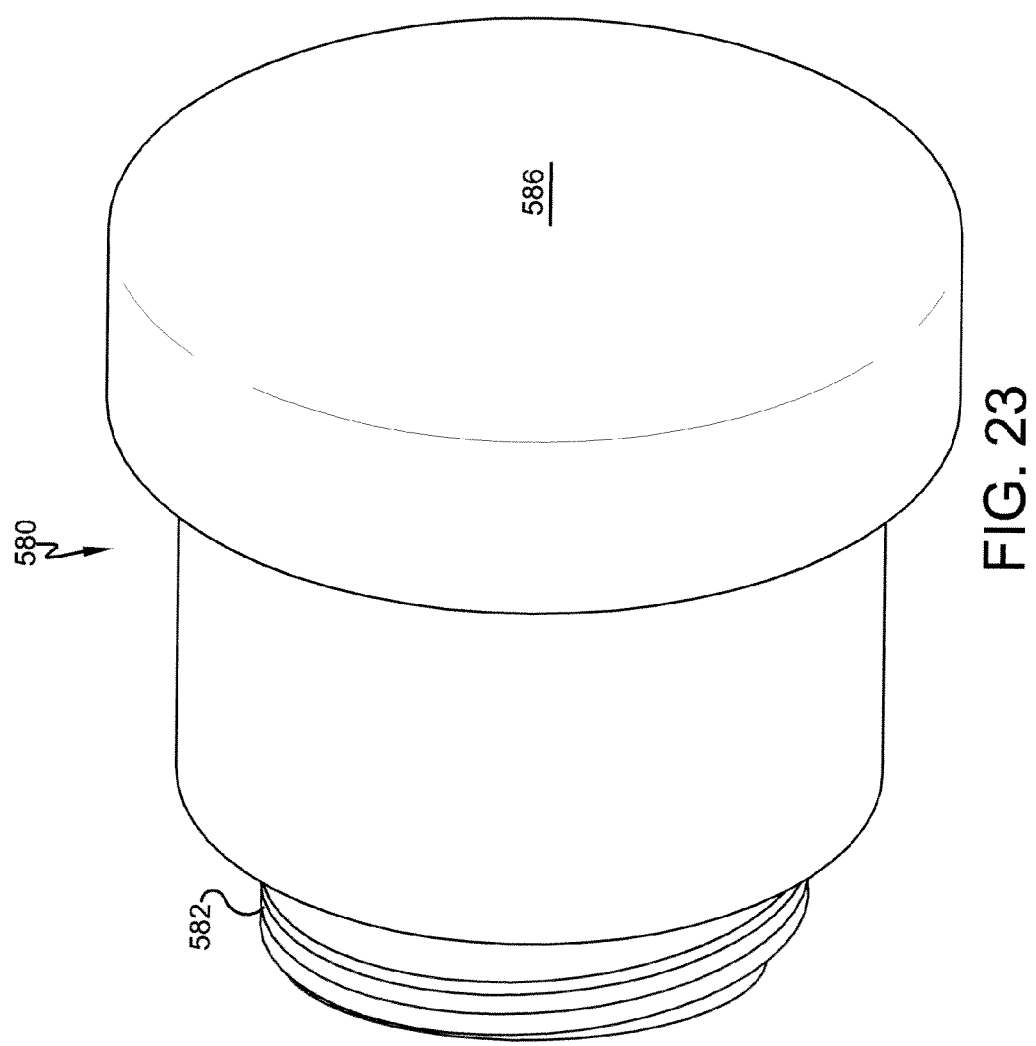
FIG. 23 is a perspective proximal end view of the cap according to one embodiment of this invention.
Figure 24:
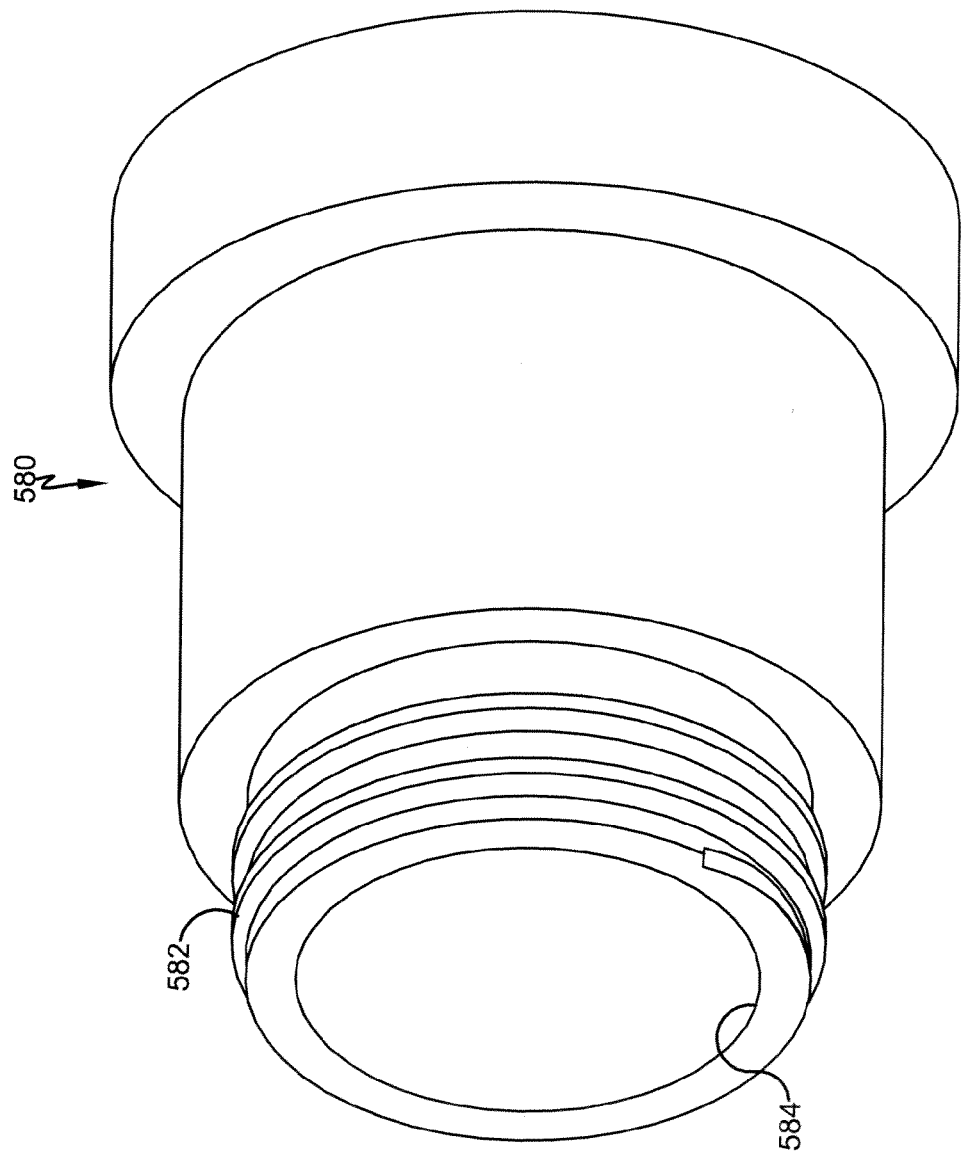
FIG. 24 is a perspective distal end view of the cap shown in FIG. 23.
Figure 25:
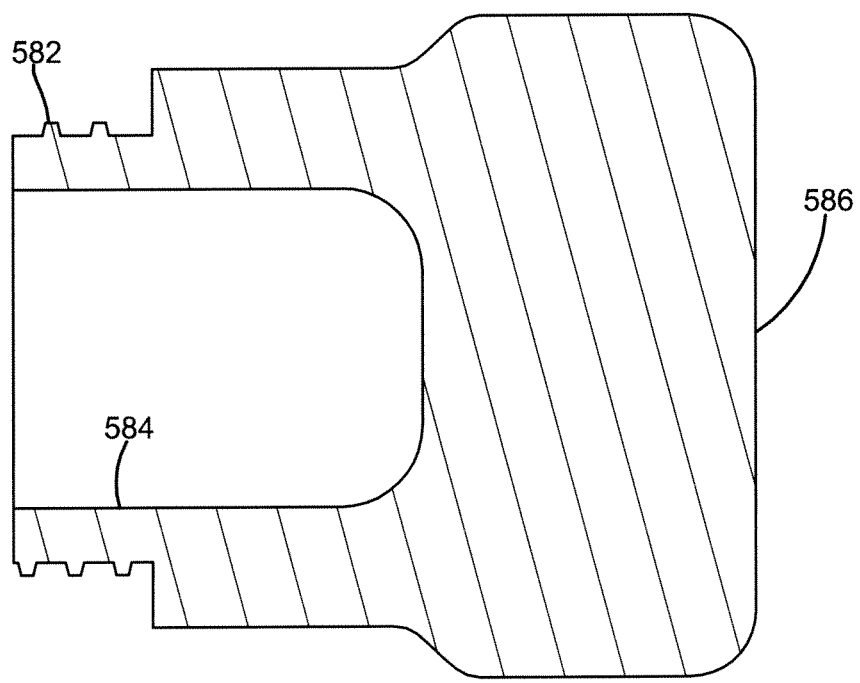
FIG. 25 is a side sectional view of the cap shown in FIG. 23.
Figure 26:
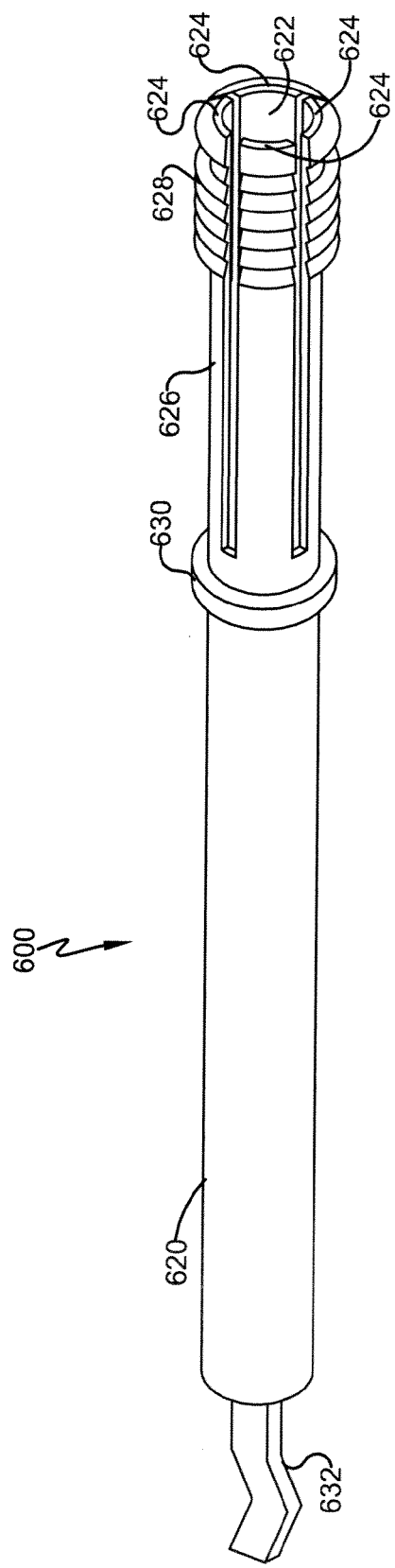
FIG. 26 is a perspective proximal end view of a tube member according to one embodiment of this invention.

With reference now to FIG. 20E, in another embodiment the tension force activator 530 includes a tension trigger mechanism 850. The tension trigger mechanism 850 may include a body 852, a hold member 854 and a trigger 856. The trigger 856 may have an attachment surface 858 at a first end that is used to attach to and move the cable 560. The cable 560 may be attached to the trigger 856 in any manner chosen with the sound judgment of a person of skill in the art. At the second end, the trigger 856 may have a grip surface 860. Between its ends, the trigger 856 may be pivotally connected, such as with a pivot pin 862, to the body 852 or to the hold member 854. The distal end of the body 852 may be connected to the proximal end of the handle 302 in any manner chosen with the sound judgment of a person of skill in the art. The body 852 may have an opening 864 that is collinear with the opening 304 formed in the handle 302. To increase the tension force on the cable 560 during surgery, the surgeon simply places the grip surface 860 of the trigger 856 in his/her palm, places his/her fingers on the hold member 854 and squeezes. This squeezing causes the second end of the trigger 856 to move in distal direction B and to thus pivot the trigger 856 about pivot pin 862. This motion in turn causes the attachment surface 858 to move in proximal direction A until the attachment surface 858 exerts a tension force on the cable 560. Continued squeezing of the trigger 856 causes the cable 560 to move in the proximal direction A so that the distal end of the cable 560 can exert a tension force on the implant 100.

Figure 27:
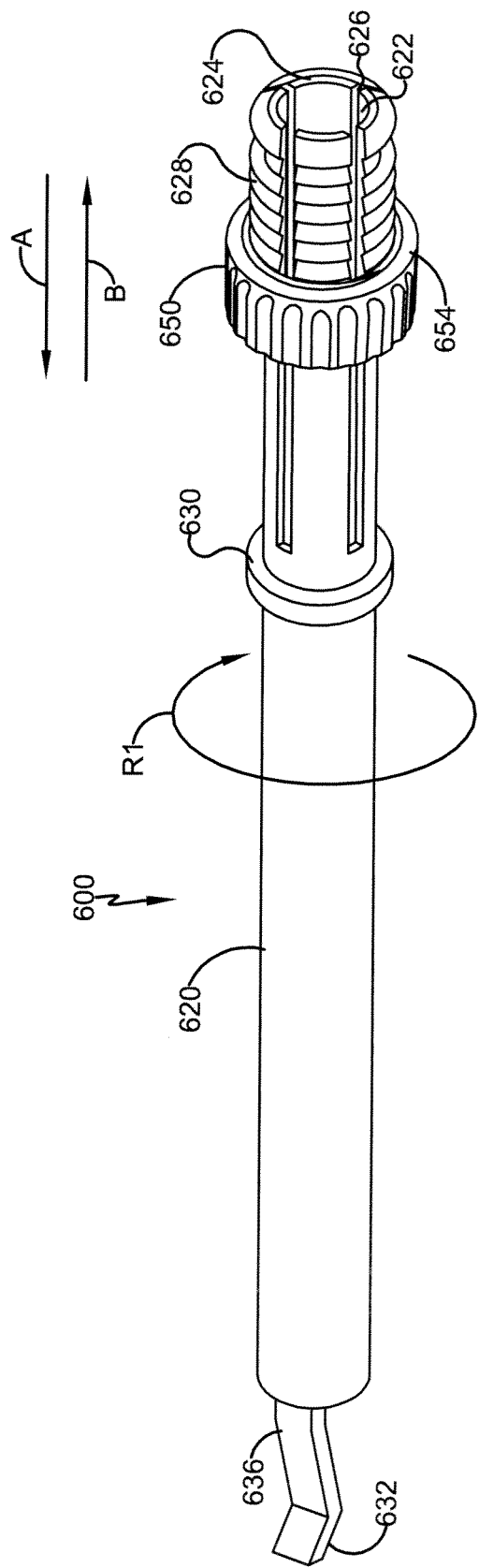
FIG. 27 is a view of the tube member similar to that shown in FIG. 26 but showing a nut attached to the tube member.
Figure 28:
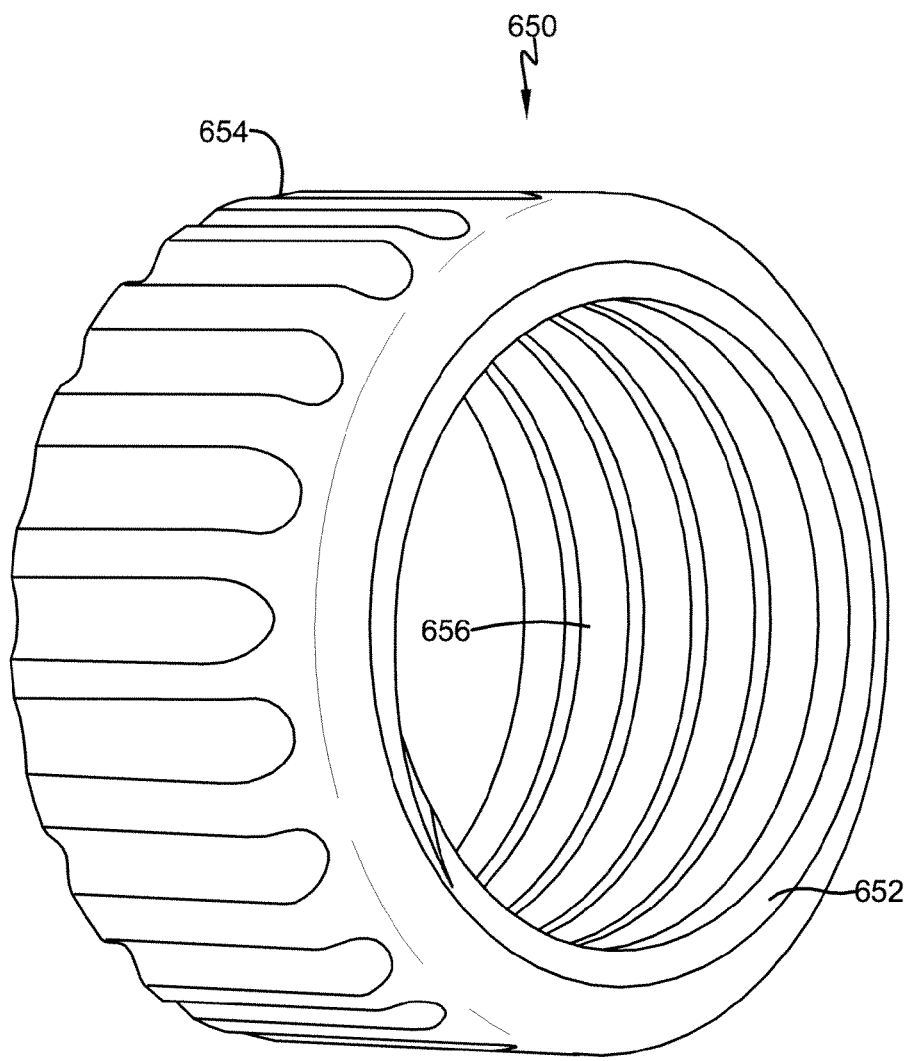
FIG. 28 is a perspective proximal end view of the nut.
Figure 29:
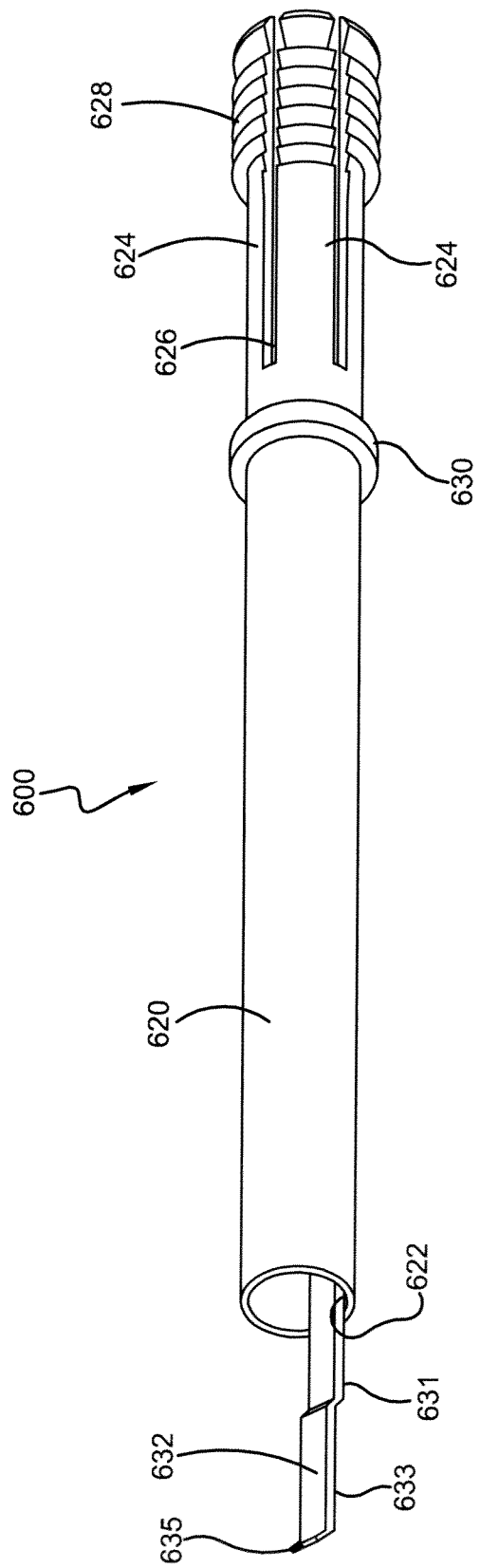
FIG. 29 is a perspective distal end view of the tube member shown in FIG. 26.

With reference now to FIGS. 2 and 26-33, the inserter 200 of this invention may also include an implant anti-deployment mechanism 600 that prevents the implant deployment mechanism 500 from operating until the surgeon is ready to operate it. In one embodiment, the implant anti-deployment mechanism 600 includes a tube member 620 that may be adjusted by the surgeon to permit operation of the implant deployment mechanism 500. The tube member 620 may be generally cylindrical and may have an opening 622 throughout its length. This opening 622 may be positioned substantially in the radial center of the tube member 620 and may receive the grip activator 460. The proximal end of the tube member 620 may have two or more arms 624, four shown, separated by a space 626 between the arms 624. A threaded region 628 may be formed on the outer surfaces of the arms 624 to receive a securing device, which in one embodiment includes a nut 650 as shown in FIGS. 2 and 27-28. The nut 650 may be generally cylindrical and may have an opening 652 throughout its length that may be positioned substantially in the radial center of the nut 650 and may be used to receive the tube member 620, as shown. The nut 650 may have an outer surface having a textured region 654 to improve the grip for the surgeon. The opening 652 may have a threaded region 656 that engages the threaded region 628 of the tube member.

With continuing reference to FIGS. 2 and 26-33, the tube member 620 may have a generally circumferential extending surface 630 distally positioned from the threaded region 628 that extends from the outer surface of the tube member 620. The extending surface 630 may serve two functions. First, it may act as a motion limiter to limit the movement of the nut in the distal direction B once the nut 650 has been disengaged from the threaded region 628 of the tube member 620. The second function of the extending surface 630 is to serve as a textured region to improve the grip for the surgeon when the surgeon is moving the tube member 620. The distal end of the tube member 620 may be adapted to prevent the implant deployment mechanism 500 from operating by interfering with the implant 100. In a specific embodiment, a clip 632 extends from the distal end of the tube member 620 and it contacts the implant 100, as shown in FIG. 30, preventing the implant 100 from being deployed. In yet a more specific embodiment, shown best in FIG. 31, the distal end of the clip 632 may be sized to be received within the gap 434 formed in the hand 428. This provides for a secure arrangement and minimizes the required length of the clip 632. The gap 434 also provides a resting place for the clip 632, also shown in FIG. 31, as the tip of the clip 632 rests on the hand 428 at the proximal end of the gap 434 after the tube member 620 has been adjusted to permit deployment of the implant 100. The clip 632 may have three sections along its length, a proximal section 631, a mid-section 633, and a distal section 635. The proximal section 631 is attached to the tube member 620 and is at the same radial position as the tube member 620. The mid-section 633 is relatively radially inward and has an inner surface 636 that contacts the outer surface of the grip activator 460. The distal section 635 extends even farther radially inward to contact the implant and to rest against the hand 428, as described above.

With reference now to FIGS. 2, 30-48 and 50-51, the inserter 200 of this invention may be used to insert and, if required, deploy any implant chosen with the sound judgment of a person of skill in the art. The implant may be, for non-limiting examples, any of the implants described in commonly owned U.S. patent application Ser. No. 11/236,068, publication number US 2007/0073398, published on Mar. 29, 2007, titled SPINE SURGERY METHOD AND IMPLANT, which is incorporated herein by reference. While the embodiments discussed below are to implants having four outer posts, it should be understood that other post arrangements are also contemplated. In one embodiment, for example, more than four posts may be used. In another embodiment, less than four posts may be used. In yet another embodiment, one of the posts (or the only post or central support structure) is positioned substantially in the axial center of the implant. In this case it may be desirable to contact the central post for insertion purposes and/or for deployment purposes.

With continuing reference to FIGS. 2, 30-48 and 50-51, as noted above with regard to the rod or wire 520, in one embodiment a given implant may be deployed by exerting a compression force on some portion of the implant. Two specific wire deployed implants will now be described. In both cases, as shown by comparing FIG. 30 with FIG. 32 and by comparing FIG. 50 with FIG. 51, the implant 100 may deploy by rotating one portion of the implant with respect to the other to expand the effective surface area of the implant 100. Also in both cases, the implant is formed of upper limbs 104 and lower limbs 106 connected to each other with four posts 110.

Figure 32:
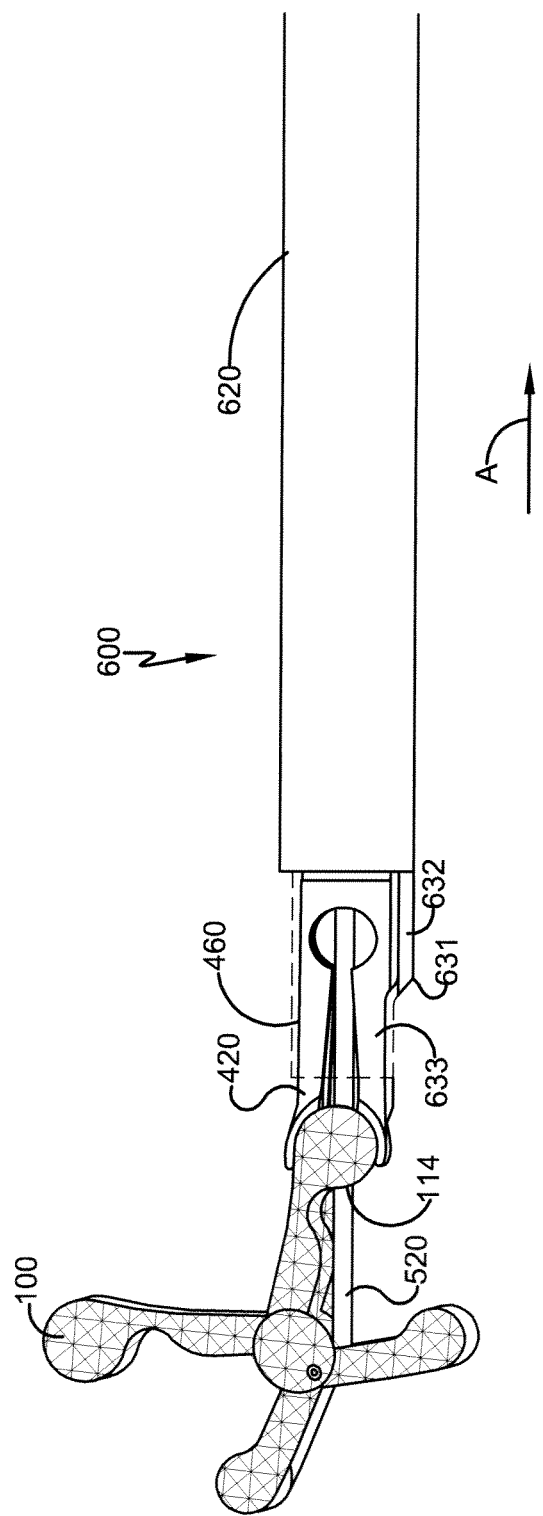
FIG. 32 is a close-up top view of the distal end of the inserter shown deploying an implant according to one embodiment.
Figure 33:
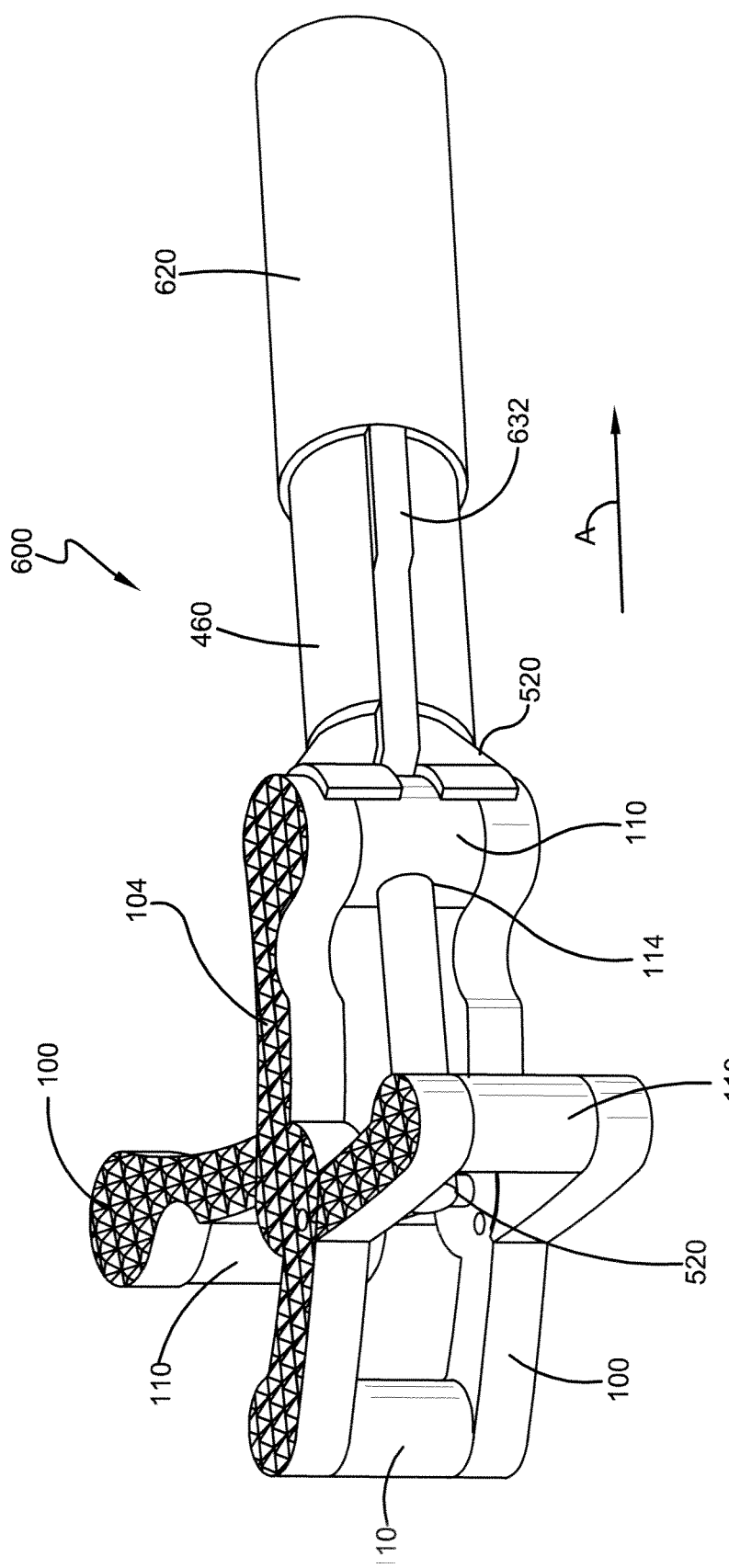
FIG. 33 is a close-up perspective view of the inserter and implant shown in FIG. 32.
Figure 34:
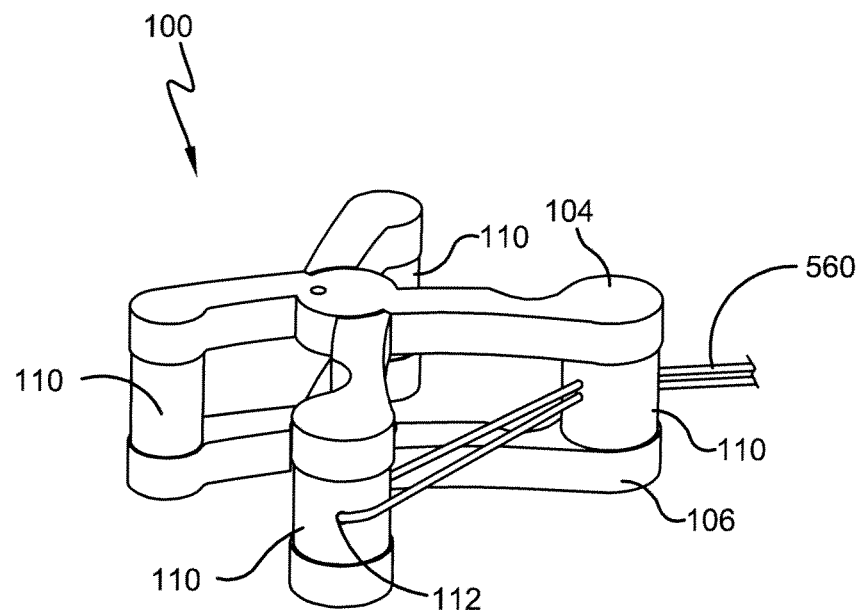
FIG. 34 is a perspective view of an implant in a deployed condition according to one embodiment of this invention.
Figure 35:
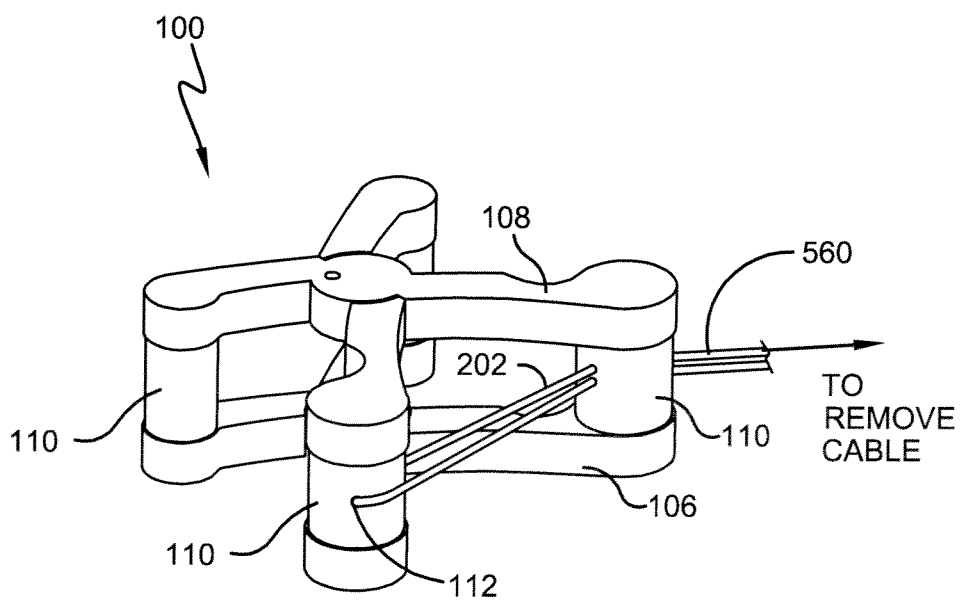
FIG. 35 is a perspective view of the implant shown in FIG. 34 but indicating how a cable may be removed.
Figure 36:
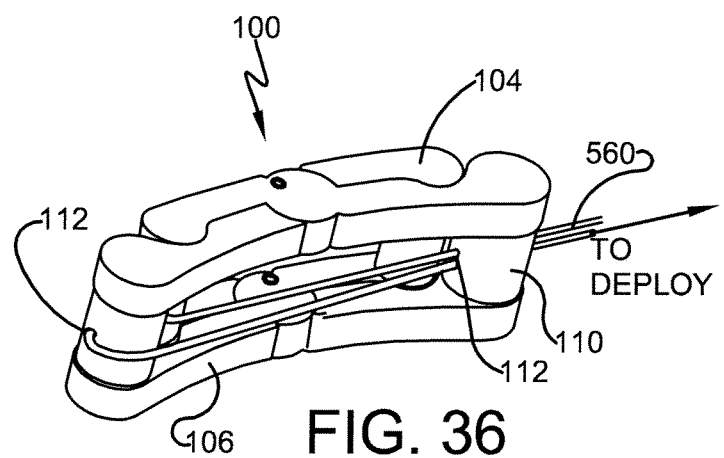
FIG. 36 is a perspective view of the implant shown in FIG. 34 but in a non-deployed condition.
Figure 37:
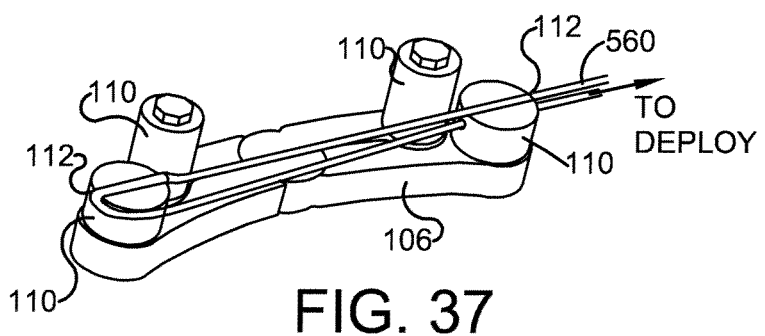
FIG. 37 is a perspective view of the implant similar to that shown in FIG. 36 but with the upper limbs removed for clarity.
Figure 38:
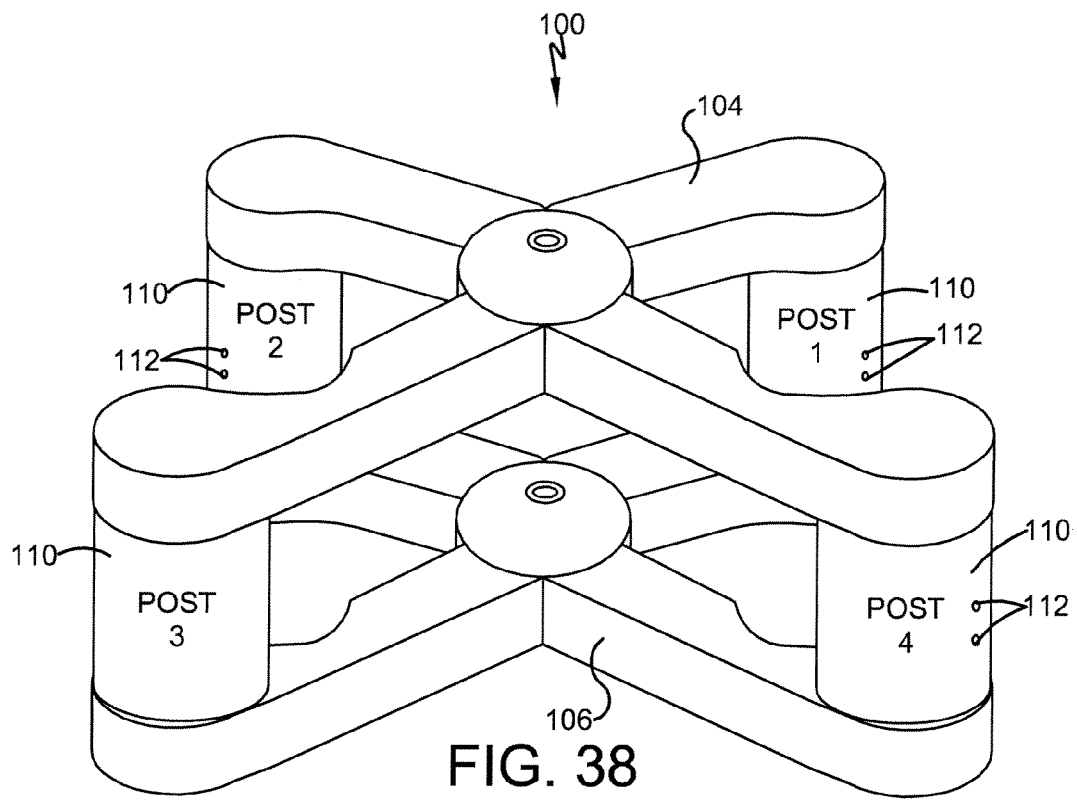
FIG. 38 is a perspective view of an implant in a deployed condition according to another embodiment of this invention.
Figure 39:
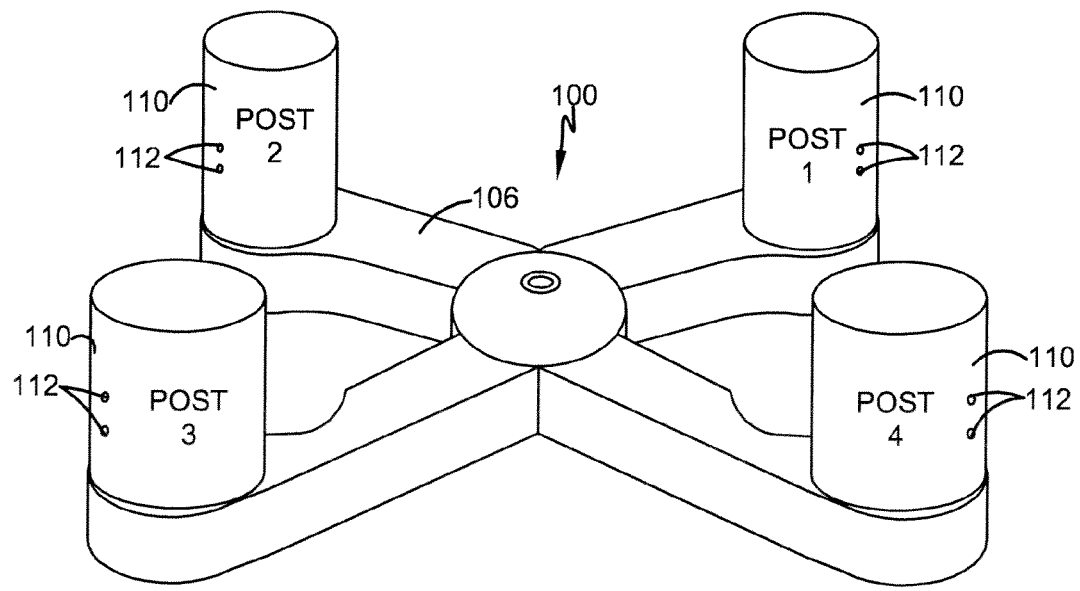
FIG. 39 is a perspective view of the implant shown in FIG. 38 but with the upper limbs removed for clarity.
Figure 40:
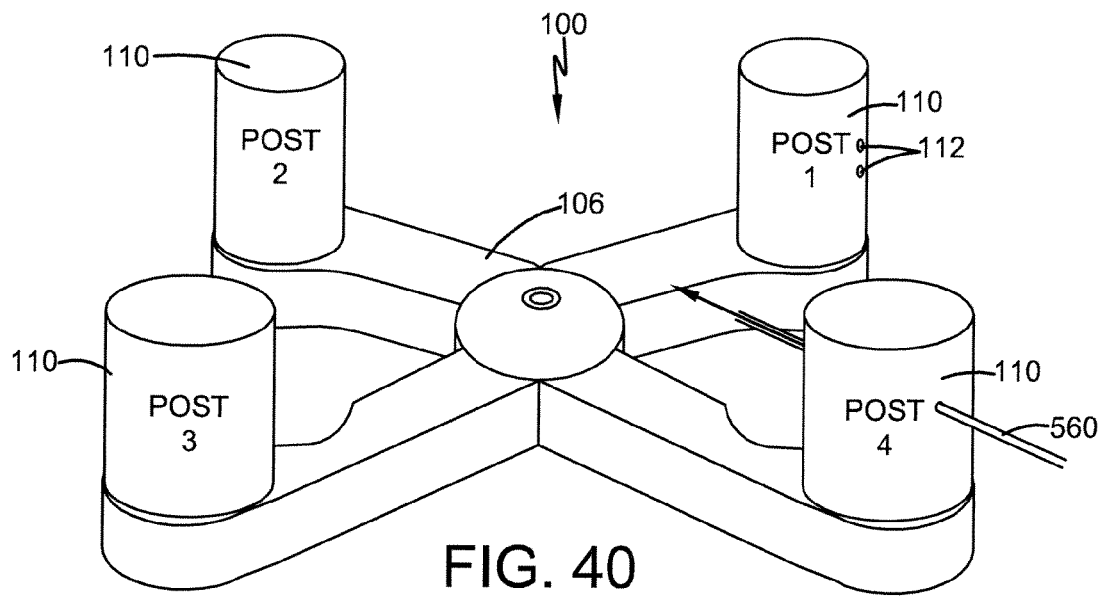
FIG. 40 is a perspective view of the implant shown in FIG. 39 but illustrating the cable being threaded through the upper hole in post 4.
Figure 41:
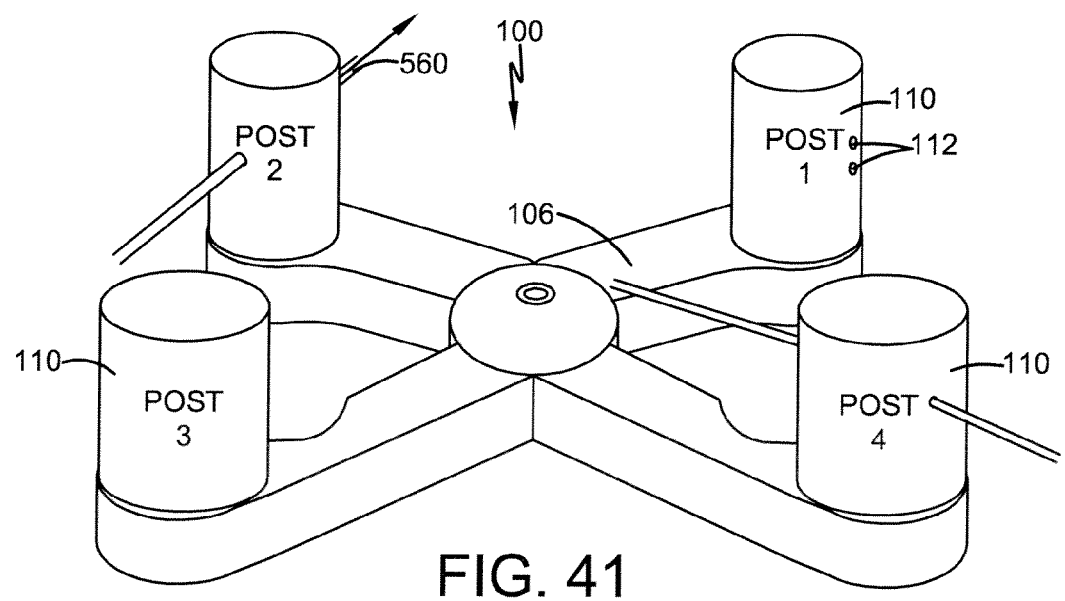
FIG. 41 is a perspective view of the implant shown in FIG. 40 but illustrating the cable being threaded through the upper hole in post 2.
Figure 42:
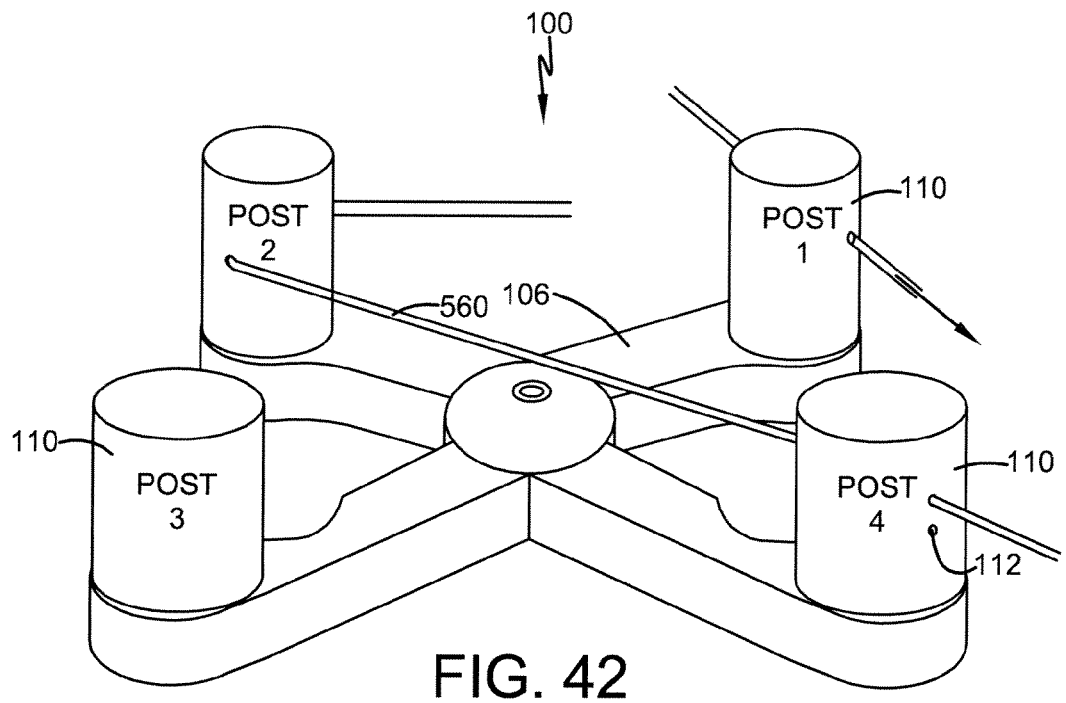
FIG. 42 is a perspective view of the implant shown in FIG. 41 but illustrating the cable being threaded through the upper hole in post 1
Figure 43:
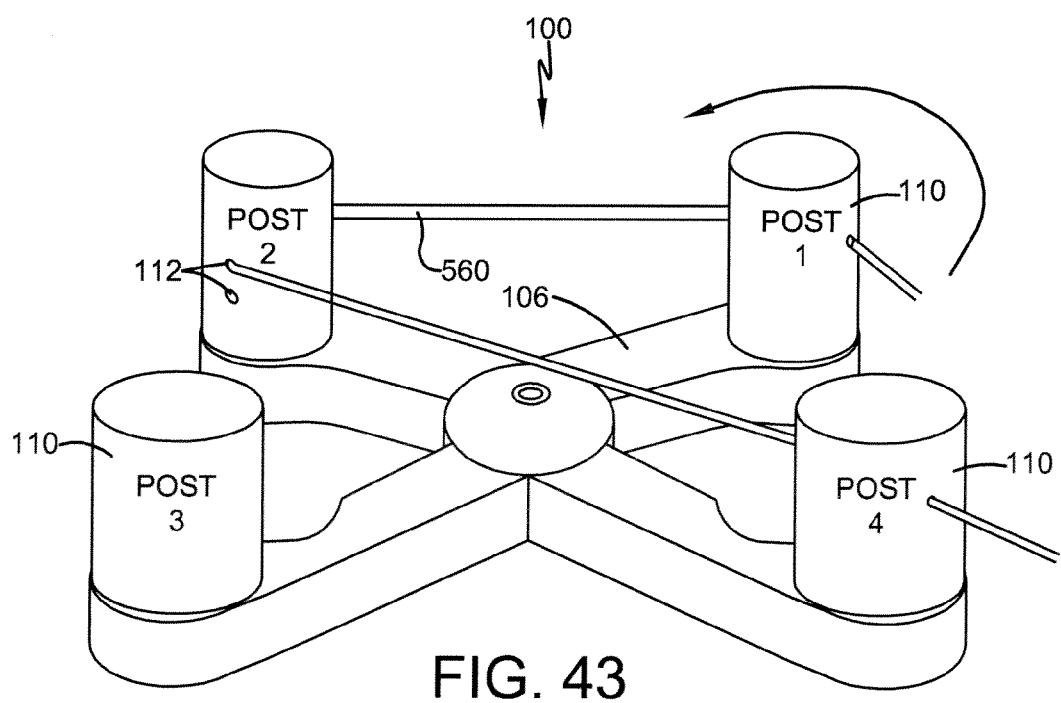
FIG. 43 is a perspective view of the implant shown in FIG. 42 but illustrating the cable being wrapped around post 1 in a counter-clockwise manner.
Figure 44:
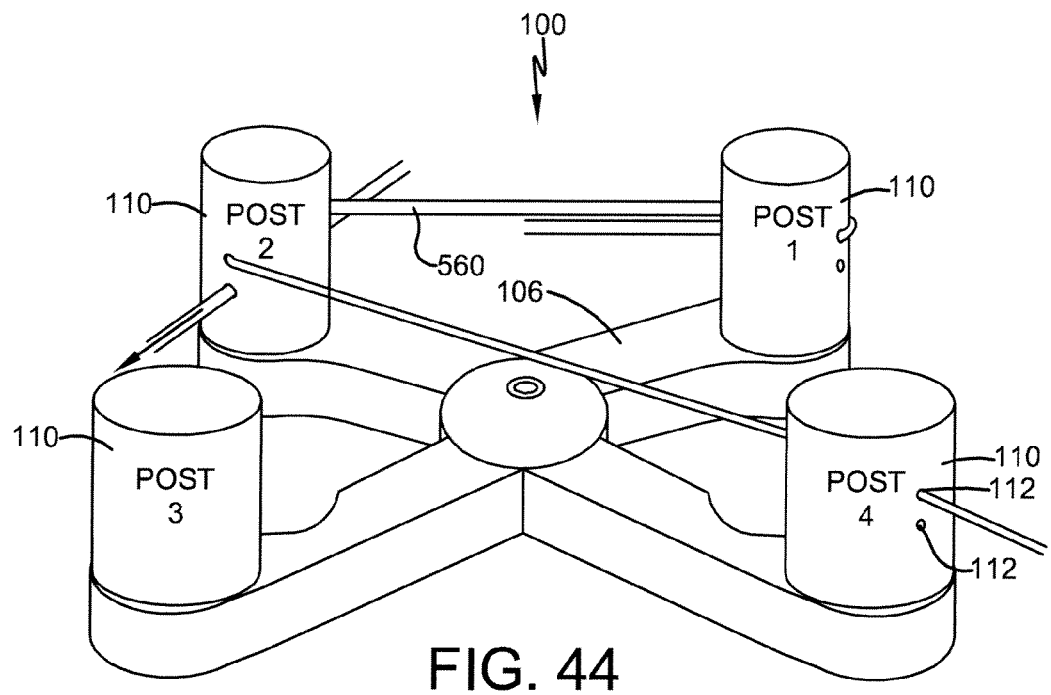
FIG. 44 is a perspective view of the implant shown in FIG. 43 but illustrating the cable being threaded through the lower hole in post 2.
Figure 45:
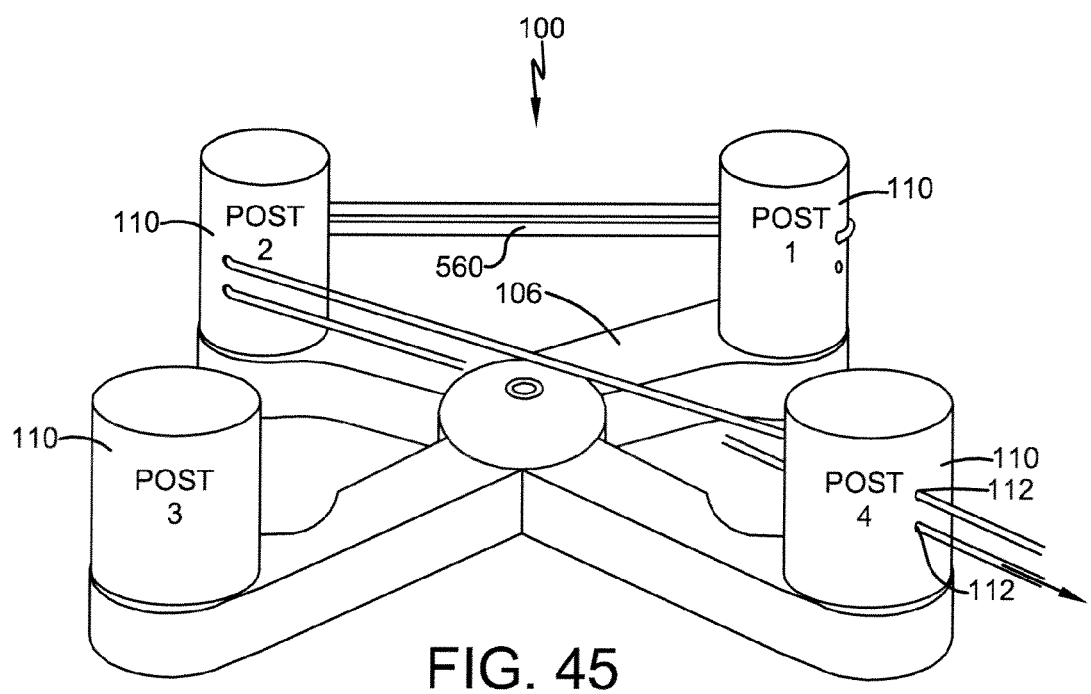
FIG. 45 is a perspective view of the implant shown in FIG. 44 but illustrating the cable being threaded through the lower hole in post 4.
Figure 46:
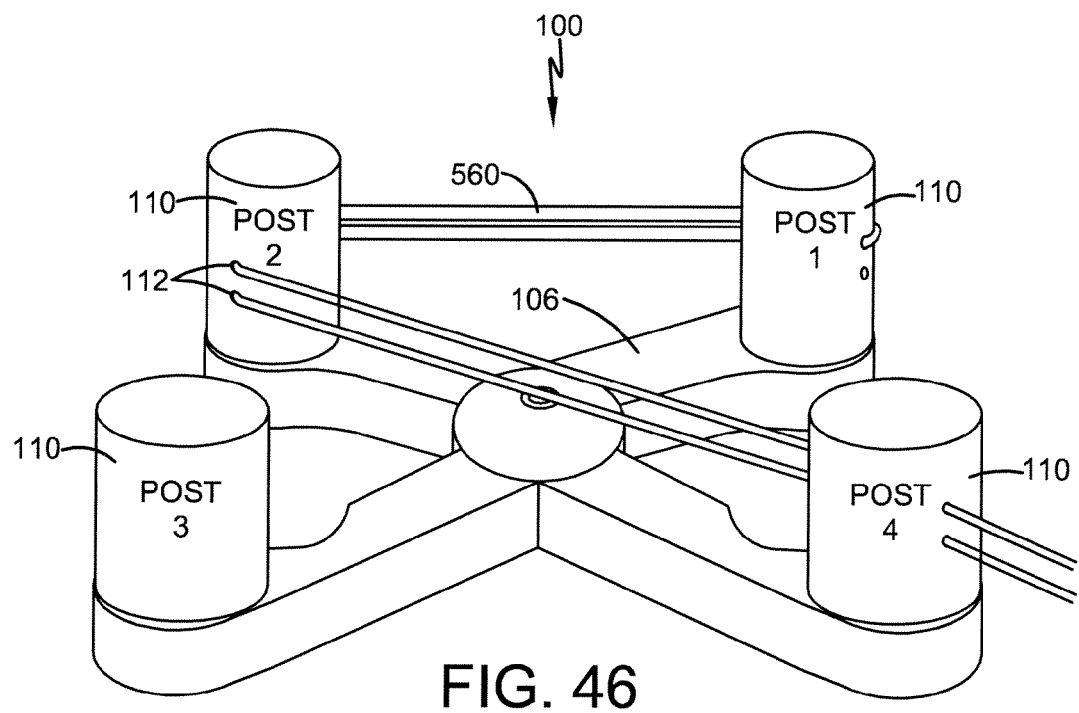
FIG. 46 is a perspective view of the implant shown in FIG. 45 but illustrating the cable threading completed.
Figure 47:
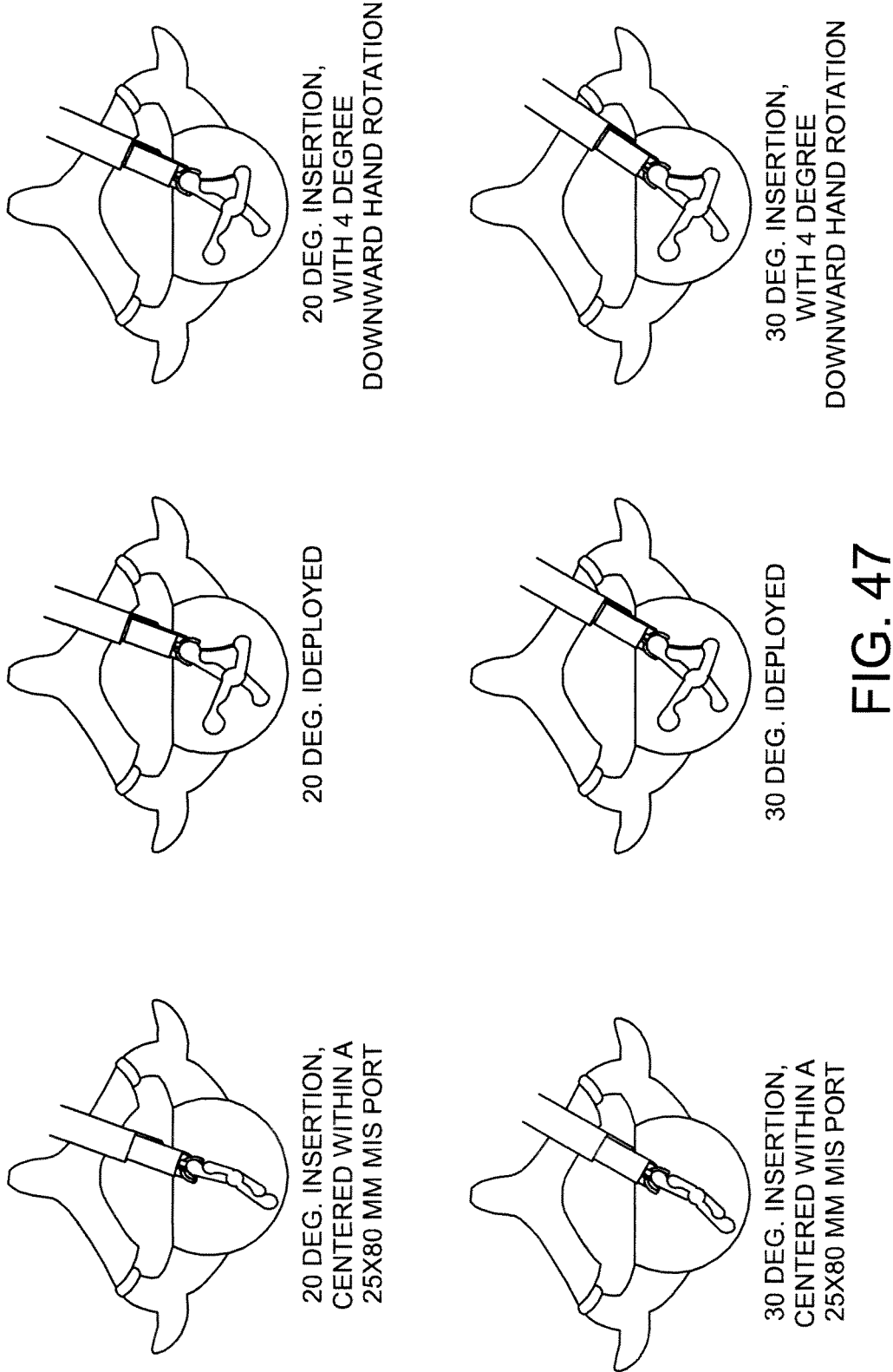
FIG. 47 shows various views of the insertion and deployment of the implant with a 20 degree insertion angle and with a 30 degree insertion angle.
Figure 49A:
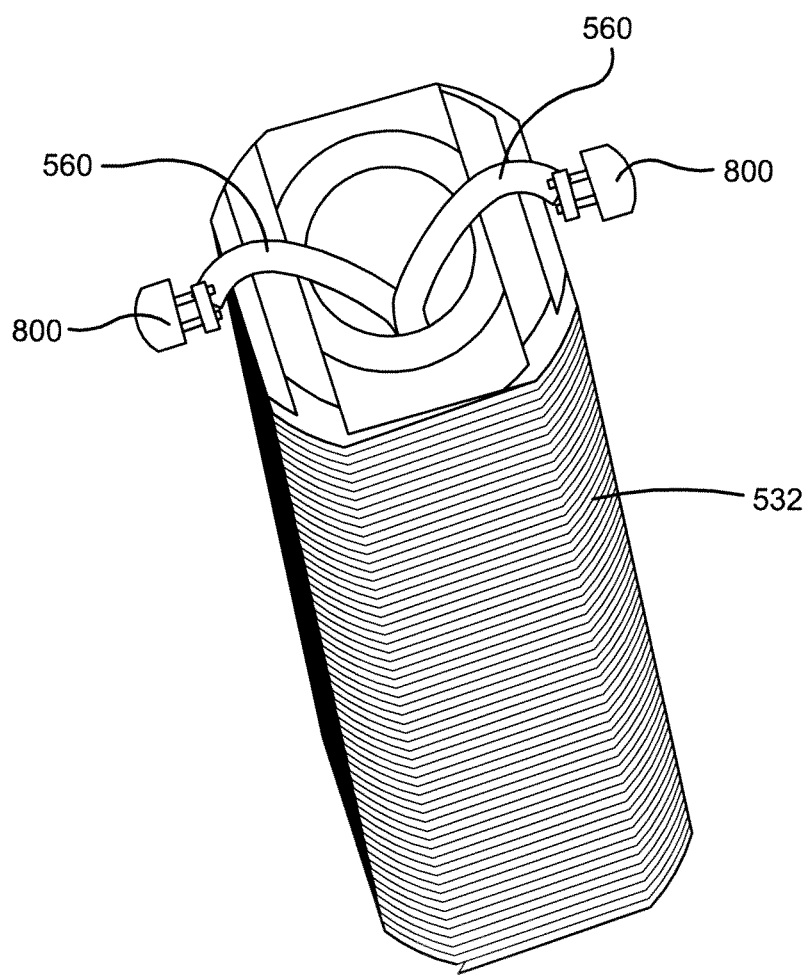
FIG. 49A is a perspective view of a screw showing how a cable may be attached using a set screw.
Figure 49B:
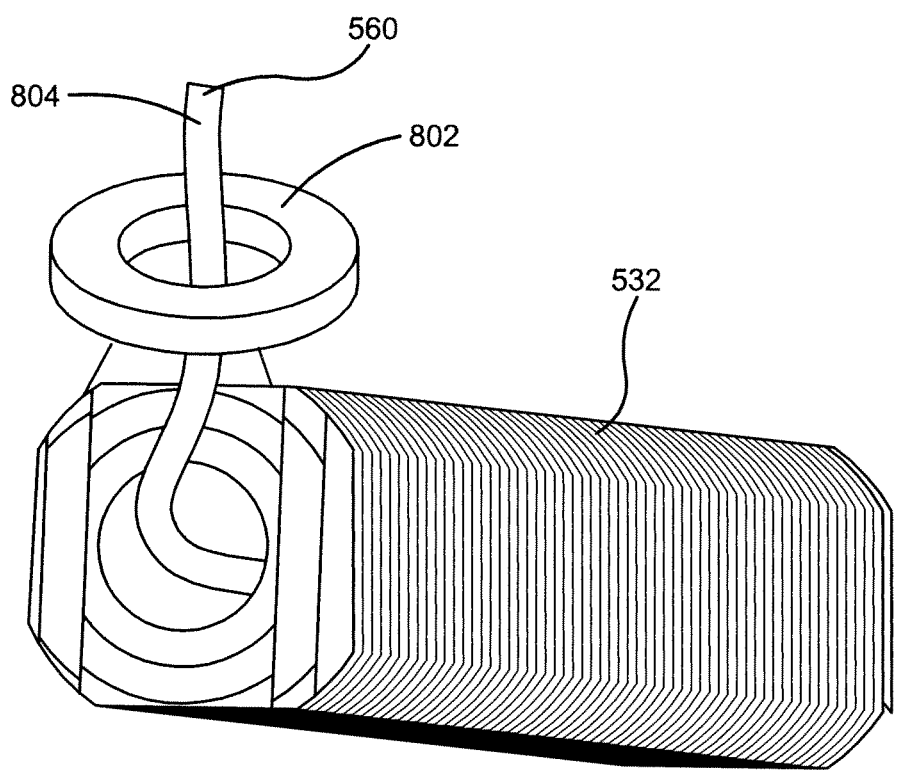
FIG. 49B is a perspective view of a screw showing how a cable may be attached using a collar.
Figure 49C:
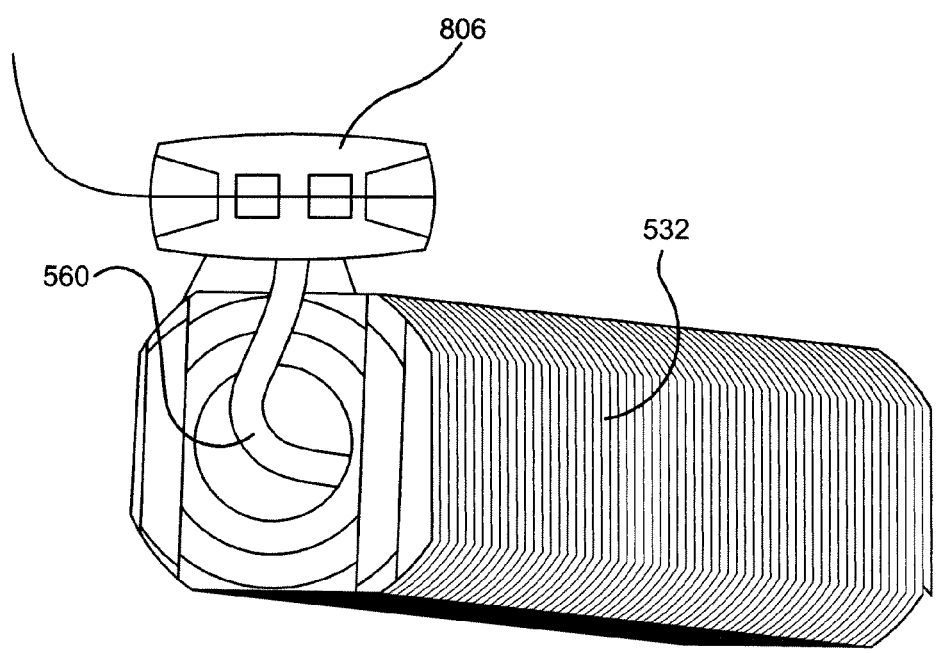
FIG. 49C is a perspective view of a screw showing how a cable may be attached using a reel member.

The first embodiment is shown in FIGS. 32-33. For this embodiment the wire 520 takes a linear path as it exits the inserter 200 and contacts the implant 100. In one specific embodiment, the post 110 gripped by the gripper 420 has a linear opening 114 that receives the wire 520 when it is extended out from the inserter 200. Continued extension of the wire 520 causes the distal end of the wire 520 to contact another implant surface, such as another post 110, to cause the implant 100 to deploy.

Figure 50:
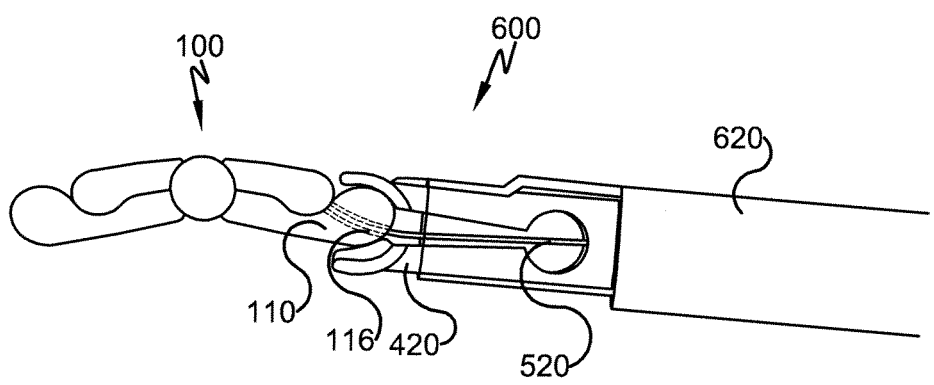
FIG. 50 is a close-up top view of the distal end of the inserter shown deploying an implant in the closed or non-deployed condition according to another embodiment.

The second embodiment is shown in FIGS. 50-51. For this embodiment the wire 520 takes a curvilinear path as it contacts the implant 100. In one specific embodiment, the post 110 gripped by the gripper 420 has a curvilinear opening 116 that receives the wire 520 when it is extended out from the inserter 200. Continued extension of the wire 520 causes the distal end of the wire 520 to contact another implant surface, such as another post 110, to cause the implant 100 to deploy. In a more specific embodiment, the portion of the implant 100 that contacts the distal end of the wire 520 has a divot 118 on its surface that matches the surface shape of the distal end of the wire 520. In this way, the distal end of the wire 520 is received in the divot 118 making it easier for the wire 520 to stay in contact with the implant surface as it moves through the curvilinear motion.

With reference now to FIGS. 34-46, as also noted above with regard to a cable 560, in another embodiment a given implant may be deployed by exerting a tension force on a cable to cause the implant to deploy. Two specific cable deployed implants will now be described. In both cases, as with the previous embodiments, the implant 100 may deploy by rotating one portion of the implant with respect to the other to expand the effective surface area of the implant 100. Also, the implant 100 is formed of upper limbs 104 and lower limbs 106 connected to each other with four posts 110. For the embodiment shown in FIGS. 34-37, only two of the posts 110 are used to deploy the implant 100. For the embodiment shown in FIGS. 38-46, three of the posts 110 are used to deploy the implant 100. In both cases the posts 110 required for deployment have post holes 112 that receive the cable 560 in any manner chosen with the sound judgment of a person of skill in the art.

With reference now to all the FIGURES but especially FIG. 2, the operation of the inserter 200 of this invention will now be described. First, the surgeon decides what type, style and size of implant to be inserted. The surgeon then assembles the appropriate inserter accordingly. It should be noted that the same handle mechanism 300 can be used with numerous implant gripping mechanisms and, if required, numerous implant deployment mechanisms and implant anti-deployment mechanisms. If a compression force member such as rigid wire 520 is to be used as the implant deployment mechanism 500, the inserter 200 can be assembled and the rigid wire 520 can be inserted and positioned into the handle opening 304, the connector opening 362, and the gripper opening 422. If a tension force member such as cable 560 is to be used as the implant deployment mechanism 500, the cable 560 can be attached to the implant (in the non-deployed condition) and then inserted through the gripper opening 422, the connector opening 362, and the handle opening 304. With the cap 580 removed, the cable 560 can then be connected to the implant deployment mechanism 500 in a manner consistent with the tension force activator 530 being used. The cap 580 can then be attached.

With continuing reference to all the FIGURES but especially FIGS. 1A, 1B and 47-48, with the inserter 200 of this invention the vetebral space 22 may be approached using universally accepted methods for anterolateral, posterior, or posterolateral (transforaminal) discectomy. Assuming a standard approach to the posterior/posterolateral annulus of the targeted disc, appropriate refraction of the neighboring neural structures is accomplished with universally available nerve root retractors. For a posterior/posterolateral approach this would include retraction of the dural sac towards the midline and retraction of the adjacent cephalad and caudad nerve roots, as would normally be done for routine discectomy. Upon isolating the annular surface of the targeted disc or targeted vertebra, variable needle sounds are placed in the vetebral space 22 with a range of radii of curvature. The range of these sounds would have been selected on the basis of pre-operative templating of available imaging studies, including plain radiographs, CT or MRI imaging. This preoperative templating provides a narrower range of radii for intraoperative confirmation, decreasing trial and error sounding. The objective of this intraoperative needle sound placement is to locate the center of the vetebral space 22. The placement of this sound would be confirmed via biplanar intraoperative fluoroscopic imaging.

Still referring to all the FIGURES but especially FIGS. 1A, 1B and 47-48, once the surgeon is satisfied with the centralization of the needle tipped sound, routine discectomy is carried out using universally accepted instruments. The vetebral space 22 is then initially distracted with short, straight interbody spacers, progressively sized until sufficient annular tension is achieved. Once this point is reached, longer, variable radii, curvilinear box chisels may be advanced into the vetebral space 22 to remove disc and/or vertebral material and cartilaginous endplate. Once a majority of intradiscal material is removed, an endplate cutter may be advanced to the entry point to make graduated cuts in the periphery of the endplate to remove the normal concave tapering of the bony endplate towards the periphery of the vertebrae. This process would insure true distraction of the vetebral space 22 from the center. A distractor is then placed within the vetebral space 22 and distraction to the selected level of annular tension is achieved. The degree of this distraction would be based on surgeon preference and/or the vetebral space 22 height of neighboring non-degenerative discs or vertebra. With this optimal distraction, further discectomy, or removal of disc material, may be accomplished. The distractor is then placed at the presumed center of the vetebral space 22 and centralized placement confirmed by intraoperative fluoroscopic imaging. Adjustments, if necessary, may be made in anterior-posterior and medial-lateral orientation until centralization of the distractor is confirmed. The distractor used may be of any type or style chosen with the sound judgment of a person of skill in the art. A non-limiting example is the distractor as described in commonly owned U.S. patent application Ser. No. 11/756,168, titled SPINE SURGERY METHOD AND INSTRUMENTATION, which is incorporated herein by reference.

Figure 18:
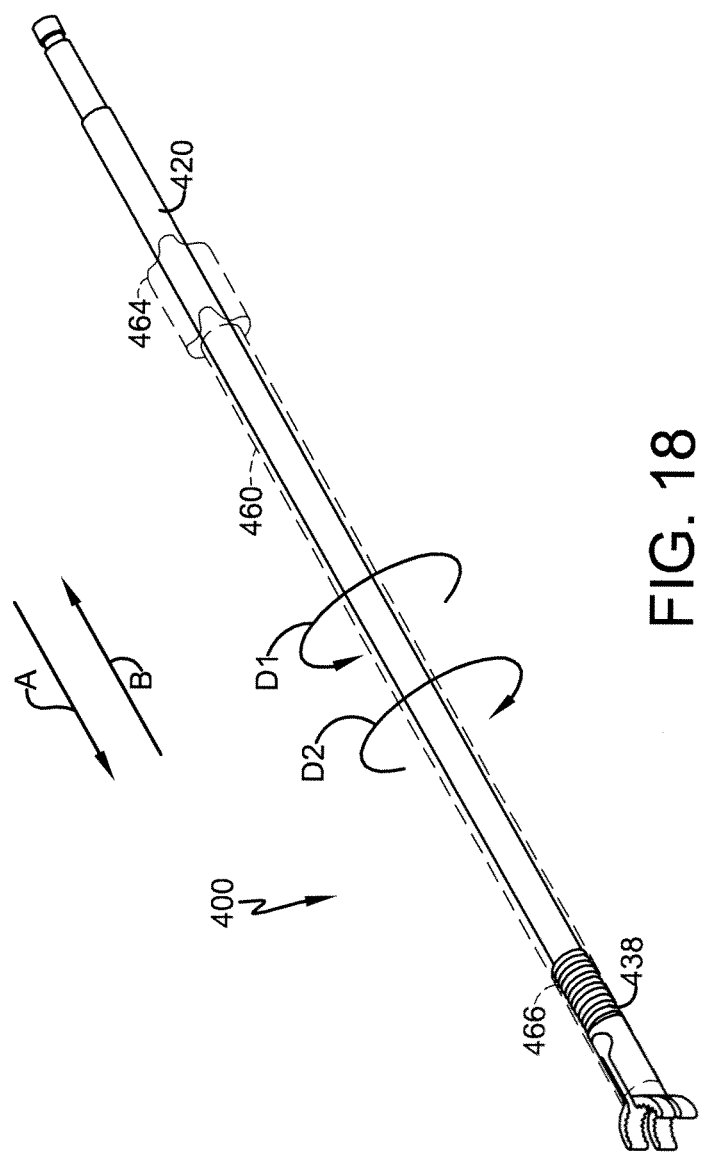
FIG. 18 is a perspective view of the gripper and grip activator similar to that shown in FIG. 17 but showing the grip activator as if transparent.

With reference now to all the FIGURES, the implant 100 is then affixed to or gripped by the inserter 200 with the implant gripping mechanism 400. In one embodiment, to activate the gripper 420 to grip the implant 100, the surgeon grips the textured region 464 of the grip activator 460 with one hand and, while holding the handle 302 with the other hand, rotates the grip activator 460 about its longitudinal axis in a first direction D1, as shown in FIG. 18. This causes the grip activator 460 to move longitudinally in the distal direction B with respect to the gripper 420 as the threaded region 466 of the grip activator 460 meshes with the threaded region of the gripper 420 in a known manner. As the grip activator 460 moves in distal direction B, it contacts the outer surfaces of the arms 426, 427, causing the arms 426, 427 as well as the hands 428, 429 to "squeeze" or move towards each other to thereby grip a portion, one of the posts 110 for example as shown in FIG. 30, of the implant 100. The surgeon can continue to rotate the grip activator 460 until the implant 100 is sufficiently gripped for surgery.

With continuing reference to all the FIGURES, the inserter 200 is then moved to insert the implant 100 within the vertebral space 22. If necessary, a surgical mallet or slap hammer may be used to transfer forces to the cap 580 to advance the implant 100 to the proper location. Biplanar fluoroscopic imaging may be used to confirm proper positioning of the implant 100. Adjustments, if necessary, can be made at this time by adjusting the amount of distraction and/or orientation of the distractor in the axial or frontal planes.

Still referring to all the FIGURES, if no deployment is required, the inserter 200 and distractor can be removed and bone grafting is completed by packing in the open profile of the implant 100. If deployment is required, the implant deployment mechanism 500 must be activated. However, if an implant anti-deployment mechanism 600 is used, it must first be adjusted by the surgeon to permit deployment. FIG. 30 shows the implant anti-deployment mechanism 600 positioned to prevent implant deployment. In one specific embodiment, the surgeon grips the textured region 654 of the nut 650 with one hand and, while holding the handle 302 with the other hand, rotates the nut 650 about its longitudinal axis in a first direction R1 as shown in FIG. 27. This causes the nut 650 to move longitudinally in the distal direction B with respect to the tube member 620 as the threaded region 558 of the nut 650 meshes with the threaded region of the tube member 620 in a known manner. As the nut 650 moves in distal direction B, it releases or "un-tightens" from the tube member 620. The surgeon can then let go of the nut 650 (its motion is limited by the extending surface 630) and grip instead the tube member 620 (at the extending surface 630, if desired) and move it in proximal direction A, as shown in FIGS. 32 and 33. As the tube member 620 moves in proximal direction A, the clip 632 moves out of contact with the implant 100 permitting deployment of the implant 100. FIGS. 31-32 show the implant anti-deployment mechanism 600 adjusted to permit implant deployment.

With continuing reference to all the FIGURES, after the implant anti-deployment mechanism 600 is adjusted to permit deployment (or, if no implant anti-deployment mechanism 600 is used), the implant deployment mechanism 500 can be activated. If a compression force member such as rigid wire 520 is used as the implant deployment mechanism 500, the wire 520 is extended out of the distal end of the gripper opening 422 where it contacts and deploys the implant 100 in a manner consistent with the particular compression force activator 700 that is used. If a tension force member such as cable 560 is used as the implant deployment mechanism 500, the cable 560 is tensioned to deploy the implant 100 in a manner consistent with the particular tension force activator 530 that is used.

Still referring to all the FIGURES, at this point, confirmation of satisfactory implant 100 alignment within the vetebral space 22 may be confirmed by intraoperative biplanar fluoroscopic imaging. Adjustments, if necessary, can be made at this time by changing the degree of distraction and medial-lateral and anterior-posterior translation of the implant 100 by impaction/retraction or rotation with the inserter 200 still in place. Once satisfactory implant 100 alignment is achieved, it must be released from the implant gripping mechanism 400. In one embodiment, to activate the gripper 420 to release the implant 100, the surgeon grips the textured region 464 of the grip activator 460 with one hand and, while holding the handle 302 with the other hand, rotates the grip activator 460 about its longitudinal axis in a second direction D2, as shown in FIG. 18. This causes the grip activator 460 to move longitudinally in the proximal direction A with respect to the gripper 420 as the threaded region 466 of the grip activator 460 meshes with the threaded region of the gripper 420 in a known manner. As the grip activator 460 moves in proximal direction A, it moves out of contact with the outer surfaces of the arms 426, 427, permitting the arms 426, 427 as well as the hands 428, 429 to move away from each other to thereby release the implant 100. The inserter 200 is then removed followed by the distractor. With the implant 100 now inserted, bone grafting is completed by packing in the open profile of the implant 100.

With continuing reference to all the FIGURES, all the implant embodiments may be formed of any material that is appropriate for insertion into an vetebral space, including, but not limited to metal, metal alloy, titanium, titanium alloy, ceramic, carbon-fiber, PEEK or any other osteobiologic or inert, biocompatible material. All the inserter embodiments may be formed of any biocompatible material suitable for surgical instruments.

With continuing reference to all the FIGURES, the lengths of the various inserter components may be varied depending on patent parameters (such as patient size) and whether the spinal surgery is done open or via MIS techniques. In one specific embodiment, connectors 360 of various lengths may be provided. In this case, the remaining components (handle 302, gripper 420, etc.) can be of the same length but be used with connectors 360 of different lengths in order to accommodate the specific patent and surgery methodology.

Numerous embodiments have been described, hereinabove. It will be apparent to those skilled in the art that the above methods and apparatuses may incorporate changes and modifications without departing from the general scope of this invention. It is intended to include all such modifications and alterations in so far as they come within the scope of the appended claims or the equivalents thereof.

I claim:

1. A surgical system for use with an associated intradiscal space comprising a first vertebral body having a first endplate and a second vertebral body adjacent the first vertebral body having a second endplate, the surgical system comprising:
   an implant comprising:
   (a) an opening;
   (b) a first portion comprising: first and second grip surfaces; an upper surface and a lower surface; and, first and second posts that connect the upper surface to the lower surface;
   (c) a second portion comprising: an upper surface and a lower surface; and, first and second posts that connect the upper surface to the lower surface;
   (d) wherein the upper and lower surfaces of the first portion and the upper and lower surfaces of the second portion define first and second contact surfaces adapted to contact the first and second endplates, respectively;
   (e) a first pivotal connection formed between the first portion and the second portion; and,
   (f) wherein the implant is deployable by pivoting the second portion with respect to the first portion at the first pivotal connection;
   a surgical inserter that inserts the implant into the associated vertebral space and deploys the implant within the associated vertebral space, the inserter comprising:
   (a) a handle;
   (b) an implant gripping mechanism comprising: a gripper having a first end attached to the handle and a second end having a pair of arms that can contact the first and second grip surfaces, respectively, to grip and release the first portion of the implant, the gripper also having an opening; wherein distal is defined as the linear direction towards the second end of the gripper and away from the first end of the gripper;
   (c) an implant deployment mechanism comprising:
      (1) a force member that comprises first and second portions; wherein at least a portion of the force member is received within the opening in the implant; and, wherein at least a portion of the force member is received within the opening in the gripper; and,
      (2) a force activator attached to the handle that applies a force to the first portion of the force member to move the force member through the opening in the implant and through the opening in the gripper to deploy the implant, while the second portion of the force member contacts the second portion of the implant and while the gripper grips only the first portion of the implant, by pivoting the second portion of the implant with respect to the first portion at the first pivotal connection; and,
   wherein the first pivotal connection is positioned distally with respect to the first and second grip surfaces of the first portion of the implant while the implant is deployed.

2. The surgical system of claim 1 wherein:
   the first pivotal connection is formed between the upper surface of the first portion of the implant and the upper surface of the second portion of the implant;
   the implant comprises a second pivotal connection formed between the lower surface of the first portion of the implant and the lower surface of the second portion of the implant;
   the implant is deployable by pivoting the second portion with respect to the first portion at the second pivotal connection; and,
   the second pivotal connection is positioned distally with respect to the first and second grip surfaces of the first portion of the implant while the implant is deployed.

3. The surgical system of claim 1 wherein:
   the force member is a compression force member; and,
   the force activator is a compression force activator that applies a compression force to the first portion of the compression force member to push the compression force member until the second portion of the compression contacts the second portion of the implant to cause the implant to pivot at the first pivotal connection to deploy the implant.

4. The surgical system of claim 1 wherein:
   the force member is a tension force member and the second portion of the tension force member is attached to the second portion of the implant; and,
   the force activator is a tension force activator that applies a tension force to the first portion of the compression force member to pull the tension force member to cause the implant to pivot at the first pivotal connection to deploy the implant.

5. The surgical system of claim 4 wherein the tension force activator comprises:
   a screw that is operatively connected to the handle and that has a threaded region;
   a tension knob having an opening that is at least partially defined by a threaded region that engages the threaded region of the screw;
   wherein the handle, the screw, and the tension knob each have an opening that receives the tension force member; and,
   wherein the tension knob is rotatable with respect to the screw to apply the tension force to the tension force member to deploy the implant.

6. The surgical system of claim 1 further comprising an anti-deployment mechanism comprising:
   a tube member having an opening that receives the gripper and the force member;
   a clip that extends from the tube member; and,
   wherein the anti-deployment mechanism is adjustable between: (1) a first position where the clip contacts the implant while the gripper grips the first portion of the implant to prevent the implant from deploying by preventing the second portion of the implant from pivoting with respect to the first portion; and, (2) a second position where the clip does not contact the implant while the gripper grips the first portion of the implant and the implant is deployable by permitting the second portion of the implant to pivot with respect to the first portion.

7. The surgical system of claim 6 wherein:
   the tube member has a threaded region;
   the anti-deployment mechanism further comprises a nut having a threaded region that meshes with the threaded region of the tube member; and,
   the nut is rotatable in: (1) a first direction with respect to the threaded region of the tube member to maintain the anti-deployment mechanism in the first position; and, (2) a second direction with respect to the threaded region of the tube member to permit the anti-deployment mechanism to be adjusted into the second position.

8. The surgical system of claim 1 wherein the opening in the implant is formed in one of the first and second posts of the first portion of the implant.

9. The surgical system of claim 1 wherein the first and second grip surfaces are formed on opposite sides of one of the first and second posts of the first portion of the implant.

10. The surgical system of claim 1 wherein the first pivotal connection is positioned laterally between: (a) the first and second posts of the first portion of the implant; and, (b) the first and second posts of the second portion of the implant.

11. A method for using a surgical system with an intradiscal space comprising a first vertebral body having a first endplate and a second vertebral body adjacent the first vertebral body having a second endplate, the method comprising the steps of:
   (A) providing an implant comprising: (a) an opening; (b) a first portion comprising: first and second grip surfaces; an upper surface and a lower surface; and, first and second posts that connect the upper surface to the lower surface; (c) a second portion comprising: an upper surface and a lower surface; and, first and second posts that connect the upper surface to the lower surface, (d) wherein the upper and lower surfaces of the first portion and the upper and lower surfaces of the second portion define first and second contact surfaces; (e) a first pivotal connection formed between the first portion and the second portion; and, (f) wherein the implant is deployable by pivoting the second portion with respect to the first portion at the first pivotal connection;
   (B) providing a surgical inserter comprising: (a) a handle; (b) an implant gripping mechanism comprising: a gripper having a first end attached to the handle, a second end having a pair of arms, and an opening; (c) an implant deployment mechanism comprising: (1) a force member that comprises first and second portions; and, (2) a force activator attached to the handle;
   (C) gripping the implant with the gripper by contacting the first and second grip surfaces of the implant with the pair of arms;
   (D) inserting the implant into the intradiscal space using the surgical inserter with the first and second contact surfaces of the implant facing the first and second endplates, respectively;
   (E) providing: at least a portion of the force member within the opening in the implant; and, at least a portion of the force member within the opening in the gripper;
   (F) deploying the implant within the intradiscal space using the implant deployment mechanism by applying a force to the first portion of the force member to move the force member through the opening in the implant and through the opening in the gripper, while the second portion of the force member contacts the second portion of the implant and while the gripper grips only the first portion of the implant, to pivot the second portion of the implant with respect to the first portion at the first pivotal connection;
   (G) removing the gripper from the implant by removing the pair of arms from the first and second grip surfaces of the implant;
   wherein distal is defined as the linear direction towards the second end of the gripper and away from the first end of the gripper; and,
      wherein during step (F) the first pivotal connection is positioned distally with respect to the first and second grip surfaces of the first portion of the implant.

12. The method of claim 11 wherein:
   step (B) comprises the steps of: providing the force member to be a compression force member; and, providing the force activator to be a compression force activator;
   step (F) comprises the step of: applying a compression force to the first portion of the compression force member to push the compression force member until the second portion of the compression contacts the second portion of the implant to cause the implant to pivot at the first pivotal connection.

13. The method of claim 11 wherein:
   step (B) comprises the steps of: providing the force member to be a tension force member; and, providing the force activator to be a tension force activator;
   prior to step (D) the method comprises the step of: attaching the second portion of the tension force member to the second portion of the implant; and,
   step (F) comprises the step of: applying a tension force to the first portion of the tension force member to pull the tension force member to cause the implant to pivot at the first pivotal connection.

14. The method of claim 13 wherein:
   step (B) comprises the steps of: providing the tension force activator to comprise: a screw that is operatively connected to the handle and that has a threaded region; a tension knob having an opening that is at least partially defined by a threaded region that engages the threaded region of the screw; and, providing the handle, the screw, and the tension knob each with an opening that receives the tension force member; and,
   step (F) comprises the step of: rotating the tension knob with respect to the screw to apply the tension force to the first portion of the tension force member.

15. The method of claim 11 wherein:
   the method further comprises the step of: providing an anti-deployment mechanism comprising: (a) a tube member having an opening that receives the gripper and the force member; and, (b) a clip that extends from the tube member;
   prior to step (D) the method comprises the step of: adjusting the anti-deployment mechanism into a first position where the clip contacts the implant while the gripper grips the first portion of the implant to prevent the implant from deploying by preventing the second portion of the implant from pivoting with respect to the first portion; and,
   after step (D) but before step (F) the method comprises the step of: adjusting the antideployment mechanism into a second position where the clip does not contact the implant while the gripper grips the first portion of the implant and the implant is deployable by permitting the second portion of the implant to pivot with respect to the first portion.

16. The method of claim 15 wherein:
   the anti-deployment mechanism tube member has a threaded region;
   the anti-deployment mechanism further comprises a nut having a threaded region that meshes with the threaded region of the tube member;
   the step of adjusting the anti-deployment mechanism into the first position comprises the step of: rotating the nut in a first direction with respect to the threaded region of the tube member; and,
   the step of adjusting the anti-deployment mechanism into the second position comprises the step of: rotating the nut in a second direction with respect to the threaded region of the tube member.

17. The method of claim 11 wherein:
   step (A) comprises the steps of: providing the first pivotal connection to be formed between the upper surface of the first portion of the implant and the upper surface of the second portion of the implant; and, providing the implant with a second pivotal connection formed between the lower surface of the first portion of the implant and the lower surface of the second portion of the implant;

step (F) comprises the step of deploying the implant by pivoting the second portion of the implant with respect to the first portion at the second pivotal connection; and, wherein during step (F) the second pivotal connection is positioned distally with respect to the first and second grip surfaces of the first portion of the implant.

18. The method of claim 11 wherein:

during step (D) the first portion of the implant is parallel or nearly parallel to the second portion of the implant; and, after step (F) the first portion of the implant is perpendicular to or nearly perpendicular to the second portion of the implant.

19. The method of claim 11 wherein:

step (B) comprises the step of: providing the implant gripping mechanism with a grip activator having an opening that threadingly receives the gripper;

step (C) comprises the step of: rotating the grip activator in a first direction with respect to the gripper to cause the arms to move toward each other to grip the implant; and, step (G) comprises the step of: rotating the grip activator in a second direction with respect to the gripper to cause the arms to move away from each other to release the implant.

20. The method of claim 11 wherein step (B) comprises the steps of:

providing the surgical inserter with a connector having first and second ends;

attaching the first end of the connector to the handle; and, attaching the second end of the connector to the implant gripping mechanism.

* * * * *